United States Patent
Zhang et al.

(10) Patent No.: US 10,517,870 B2
(45) Date of Patent: Dec. 31, 2019

(54) ARYL SUBSTITUTED BICYCLE HETEROARYL COMPOUNDS

(71) Applicant: Bristol-Myers Squibb Company, Princeton, NJ (US)

(72) Inventors: Xiaojun Zhang, Furlong, PA (US); Xiaofan Zheng, Cheshire, CT (US); Louis S. Chupak, Old Saybrook, CT (US)

(73) Assignee: Bristol-Myers Squibb Company, Princeton, NJ (US)

( * ) Notice: Subject to any disclaimer, the term of this patent is extended or adjusted under 35 U.S.C. 154(b) by 0 days.

(21) Appl. No.: 15/747,218

(22) PCT Filed: Jul. 28, 2016

(86) PCT No.: PCT/US2016/044388
§ 371 (c)(1),
(2) Date: Jan. 24, 2018

(87) PCT Pub. No.: WO2017/019828
PCT Pub. Date: Feb. 2, 2017

(65) Prior Publication Data
US 2018/0214445 A1 Aug. 2, 2018

Related U.S. Application Data

(60) Provisional application No. 62/198,706, filed on Jul. 30, 2015.

(51) Int. Cl.
| | |
|---|---|
| A61K 31/498 | (2006.01) |
| C07D 241/44 | (2006.01) |
| A61P 7/02 | (2006.01) |
| A61P 9/10 | (2006.01) |
| A61P 31/20 | (2006.01) |

(52) U.S. Cl.
CPC ............ *A61K 31/498* (2013.01); *A61P 7/02* (2018.01); *A61P 9/10* (2018.01); *A61P 31/20* (2018.01); *C07D 241/44* (2013.01)

(58) Field of Classification Search
CPC ..................... C07D 241/44; C07D 241/42
See application file for complete search history.

(56) References Cited

U.S. PATENT DOCUMENTS

| | | | | |
|---|---|---|---|---|
| 5,110,347 | A | 5/1992 | Selby | |
| 7,501,416 | B2 * | 3/2009 | Kim ..................... | C07D 241/42 514/249 |
| 8,138,347 | B2 * | 3/2012 | Knight ................. | C07D 285/24 544/105 |
| 8,487,103 | B2 * | 7/2013 | de Vicente Fidalgo ...................... | C07D 213/69 546/152 |
| 8,618,151 | B2 * | 12/2013 | Li ........................ | C07D 403/14 514/394 |
| 8,653,268 | B2 * | 2/2014 | Mulvihill ............. | C07D 471/04 544/350 |
| 8,685,991 | B2 * | 4/2014 | Wagner ................ | C07D 239/22 514/274 |
| 8,785,433 | B2 * | 7/2014 | Knight ................. | C07D 285/24 514/223.2 |
| 9,340,528 | B2 * | 5/2016 | Bader .................. | C07D 401/04 |
| 9,370,508 | B2 * | 6/2016 | Garcia-Echeverria ...................... | A61K 31/4745 |
| 9,662,311 | B2 * | 5/2017 | Liu ...................... | C07D 405/14 |
| 9,776,981 | B2 * | 10/2017 | Lavoie ................ | C07D 401/14 |
| 10,220,035 | B2 * | 3/2019 | Nagarathnam ...... | A61K 31/519 |

(Continued)

FOREIGN PATENT DOCUMENTS

| | | |
|---|---|---|
| CN | 102532932 A | 7/2012 |
| EP | 0 052 016 A1 | 5/1982 |

(Continued)

OTHER PUBLICATIONS

C. Lindsley et al., 2 ACS Chemical Neuroscience, 471-482 (2011).*
A. Sheaffer et al. PLOS ONE (2016) (Year: 2016).*
C.S. Demmer et al., ACS Chemical Neuroscience (2017) (Year: 2017).*
Ding, Wei-Lu et al., "Molecular Engineering of Indoline-Based D-A-π-A Organic Sensitizers toward High Efficiency Performance from First-Principles Calculations", The Journal of Physical Chemistry, vol. 117, pp. 17382-98 (2013).
Lindsley, C. W. et al., "(3-Cyano-5-fluorophenyl)biaryl Negative Allosteric Modulators of mGlu₅: Discovery of a New Tool Compound with Activity in the OSS Mouse Model of Addiction", ACS Chemical Neuroscience, vol. 2, pp. 471-482 (2011).
Martin, Christian et al., "O.Chlorobenzonitrile reacts with carbanions from methylpyrazine in liquid ammonia, affording selectively arylmetylpyrazine derivatives" Tetrahedron Letters, vol. 30(6), pp. 935-936 (1989).

(Continued)

*Primary Examiner* — Alexander R Pagano
(74) *Attorney, Agent, or Firm* — Mary K. VanAtten

(57) ABSTRACT

Disclosed is a compound of Formula (I) or a stereoisomer, tautomer, pharmaceutically acceptable salt, solvate or prodrug thereof, wherein one $R_3$ is H and the other $R_3$ is an aryl group substituted with zero to 3 $R_{3a}$; and $R_1$, $R_2$, and $R_{3a}$ are defined herein. Also disclosed are methods of using such compounds as PAR4 inhibitors for the inhibition or prevention of platelet aggregation, and the treatment of a thromboembolic disorder or the primary prophylaxis of a thromboembolic disorder. Also disclosed are methods of using such compounds for the treatment of human papillomavirus. Additionally, pharmaceutical compositions comprising at least one compound of Formula (I) are disclosed.

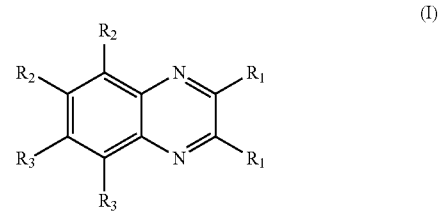

4 Claims, 1 Drawing Sheet

(56) References Cited

U.S. PATENT DOCUMENTS

| | | | | |
|---|---|---|---|---|
| 2006/0211698 A1* | 9/2006 | Botyanszki | ........ | C07D 209/08 514/249 |
| 2009/0081165 A1* | 3/2009 | Schmitz | ........ | C07D 401/04 424/85.7 |
| 2010/0234386 A1* | 9/2010 | Chaudhari | ........ | C07D 401/04 514/249 |
| 2012/0053148 A1* | 3/2012 | Cai | ........ | A61K 45/06 514/82 |
| 2015/0182490 A1* | 7/2015 | Brown | ........ | A61K 31/047 514/475 |

FOREIGN PATENT DOCUMENTS

| | | | |
|---|---|---|---|
| EP | 0 534 443 A1 | 3/1993 | |
| EP | 2 514 749 A1 | 10/2012 | |
| WO | WO1992/09578 A1 | 6/1992 | |
| WO | WO1998/20007 A1 | 5/1998 | |
| WO | WO1999/50254 A1 | 10/1999 | |
| WO | WO2008/148867 A2 | 12/2008 | |
| WO | WO-2009021083 A1 * | 2/2009 | ........ C07D 401/14 |
| WO | WO2009/141386 A1 | 11/2009 | |
| WO | WO2010/052448 A2 | 5/2010 | |
| WO | WO2010/115719 A1 | 10/2010 | |
| WO | WO2011/026579 A1 | 3/2011 | |
| WO | WO-2011026579 A1 * | 3/2011 | ........ C07D 401/04 |
| WO | WO2011/060526 A1 | 5/2011 | |
| WO | WO2011/156610 A2 | 12/2011 | |
| WO | WO2012/071414 A2 | 5/2012 | |
| WO | WO2014/095775 A1 | 6/2014 | |

OTHER PUBLICATIONS

Pei, Kai et al., "Dye-Sensitized Solar Cells Based on Quinoxaline Dyes: Effect of π-Linker on Absorption, Energy Levels, and Photovoltaic Performances", The Journal of Physical Chemistry, vol. 118, pp. 16552-16561 (2014).

Porter, John et al., "Discovery of a novel series of quinoxalines as inhibitors of c-Met Kinase", Bioorganic & Medicinal Chemistry Letters, vol. 19, pp. 397-400 (2009).

Sheaffer, Amy et al., "A Small Molecule Inhibitor Selectively Induces Apoptosis in Cells Transformed by High Risk Human Papilloma Viruses", PLOS One, vol. 11(6) pp. 1-18 (2016).

* cited by examiner

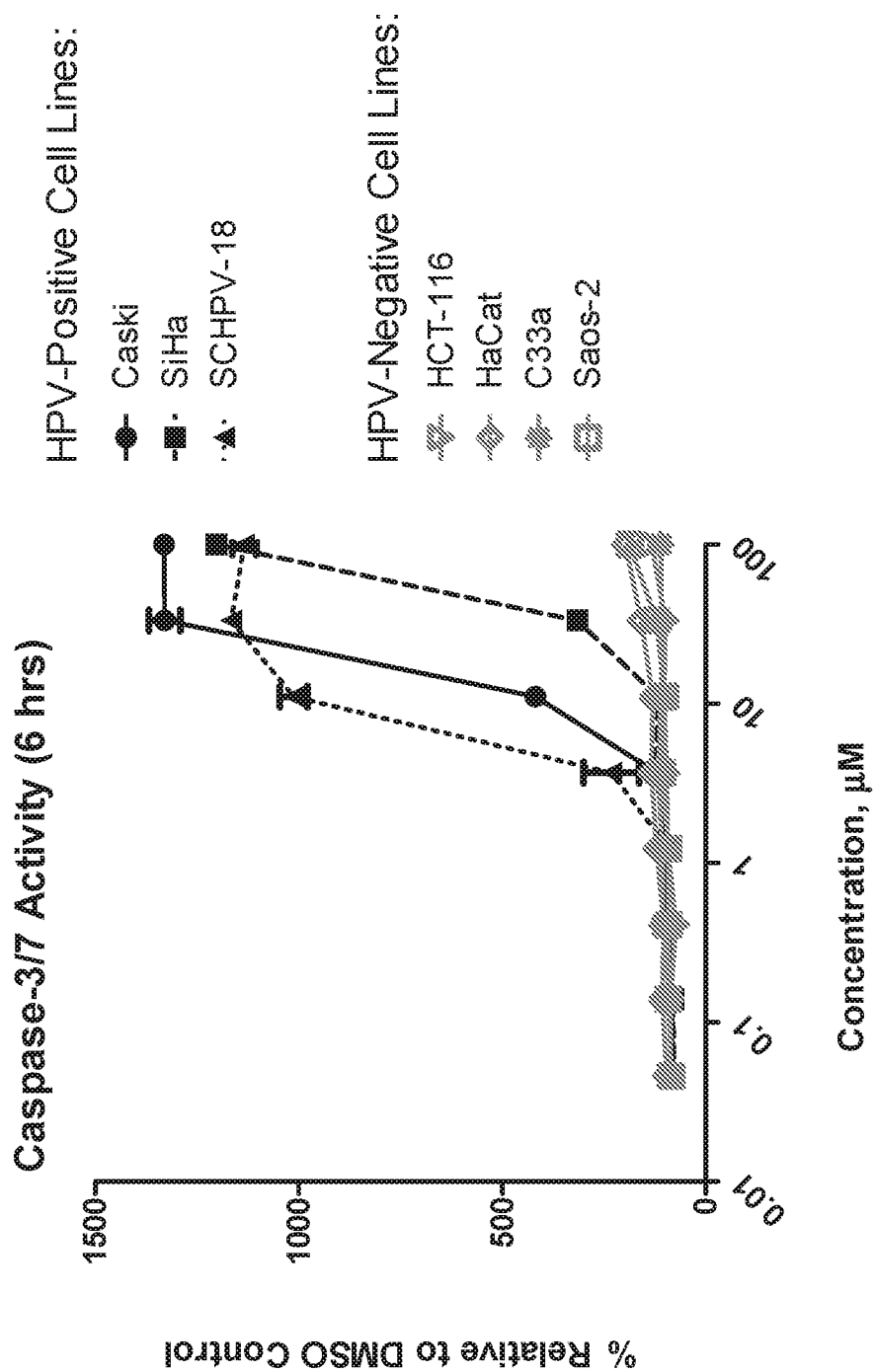

ARYL SUBSTITUTED BICYCLE HETEROARYL COMPOUNDS

The present invention generally relates to aryl substituted heteroaryl compounds useful in the treatment of disease. Provided herein are aryl substituted heteroaryl compounds, compositions comprising such compounds, and methods of their use. The invention further pertains to pharmaceutical compositions containing at least one compound according to the invention that are useful in preventing or treating diseases including thromboembolic disorders and human Papilloma virus (HPV) neoplasia and cancer.

Thromboembolic diseases remain the leading cause of death in developed countries despite the availability of anticoagulants such as warfarin (COUMADIN®), heparin, low molecular weight heparins (LMWH), synthetic pentasaccharides, and antiplatelet agents such as aspirin and clopidogrel (PLAVIX®).

Current anti-platelet therapies have limitations including increased risk of bleeding as well as partial efficacy (relative cardiovascular risk reduction in the 20 to 30% range). Thus, discovering and developing safe and efficacious oral or parenteral antithrombotics for the prevention and treatment of a wide range of thromboembolic disorders remains an important goal.

Alpha-thrombin is the most potent known activator of platelet aggregation and degranulation. Activation of platelets is causally involved in atherothrombotic vascular occlusions. Thrombin activates platelets by cleaving G-protein coupled receptors termed protease activated receptors (PARs). PARs provide their own cryptic ligand present in the N-terminal extracellular domain that is unmasked by proteolytic cleavage, with subsequent intramolecular binding to the receptor to induce signaling (tethered ligand mechanism; Coughlin, S. R., *Nature*, 407:258-264 (2000)). Synthetic peptides that mimic the sequence of the newly formed N-terminus upon proteolytic activation can induce signaling independent of receptor cleavage. Platelets are a key player in atherothrombotic events. Human platelets express at least two thrombin receptors, commonly referred to as PAR1 and PAR4. Inhibitors of PAR1 have been investigated extensively, and several compounds, including vorapaxar and atopaxar have advanced into late stage clinical trials. Recently, in the TRACER phase III trial in ACS patients, vorapaxar did not significantly reduce cardiovascular events, but significantly increased the risk of major bleeding (Tricoci, P. et al., *N. Eng. J. Med.* 366(1):20-33 (2012). Thus, there remains a need to discover new antiplatelet agents with increased efficacy and reduced bleeding side effects.

There are several early reports of preclinical studies of PAR4 inhibitors. Lee. F-Y. et al., "Synthesis of 1-Benzyl-3-(5'-hydroxymethyl-2'-furyl)indazole Analogues as Novel Antiplatelet Agents", *J. Med. Chem.*, 44(22):3746-3749 (2001) discloses in the abstract that the compound

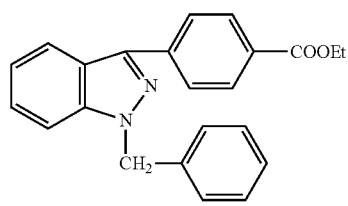

"was found to be a selective and potent inhibitor or protease-activated receptor type 4 (PAR4)-dependent platelet activation." Compound 58 is also referred to as YD-3 in Wu, C-C. et al., "Selective Inhibition of Protease-activated Receptor 4-dependent Platelet Activation by YD-3 ", *Thromb. Haemost.*, 87:1026-1033 (2002). Also, see Chen. H. S. et al., "Synthesis and platelet activity", *J. Bioorg. Med. Chem.*, 16:1262-1278 (2008).

EPI 166785 A1 and EP0667345 disclose various pyrazole derivatives which are useful as inhibitors of platelet aggregation.

The PCT publications WO 2013/163279, WO 2013/163244, and WO 2013/163241 disclose various PAR4 antagonists that are useful as inhibitors of platelet aggregation.

There still remains a need for compounds useful as inhibitors of platelet aggregation.

Applicants have found potent compounds that have activity as PAR4 inhibitors. These compounds are provided to be useful as pharmaceuticals with desirable stability, bioavailability, therapeutic index, and toxicity values that are important to their drugability.

Cervical cancer is the second leading cause of cancer deaths in women ages 15-44 worldwide with greater than 260,000 new cervical cancer deaths occurring annually.

Cervical cancer has been linked to the presence of transforming or high risk types of human Papilloma viruses (HPVs)(Bruni L., Barrionuevo-Rosas L., Serran B., Brotons M., Cosano R., Munoz J., Bosch F. X., de Sanjose S., Castellsague X. ICO Information Centre on HPV and Cancer (HPV Information Centre). *Human Papillomavirus and Related Diseases in World*. Summary Report 2014-04-08. [Data Accessed 2014-05-27]), (Bosch F X, Munoz N, de sanjose S, et al. *Int J Cancer* 1992; 52:750-758), (Munoz N, Bosch F X, de Sanjose S, et al. *Int J Cancer* 1992; 52:743-749). More than 70% of cervical cancers are associated with the high risk genotypes HPV-16 and HPV-18, with less prevalent genotypes, including HPV-31, -33, -45, and -58 together accounting for nearly all the remaining cases (Bruni L., Barrionuevo-Rosas L., Serran B., Brotons M., Cosano R., Munoz J., Bosch F. X., de Sanjose S., Castellsague X. ICO Information Centre on HPV and Cancer (HPV Information Centre). *Human Papillomavirus and Related Diseases in World*. Summary Report 2014-04-08. [Data Accessed 2014-05-27]). Integration of the HPV genome into the host cell genome coincides with an up-regulation in expression of two viral oncogenes, E6 and E7, required for cellular transformation and for ongoing replication of HPV transformed cells (Munger, K. Phelps, W. C., Bubb, V., Howley, P. M., Schlegel, R. *J. Virol.* 1989; 63:4417-4421), (Magaldi, T. G., Almstead, L. L., Bellone, S. Prevatt, E. G., Santin, A. D., DiMaio, D. *Virology* 2012; 422:114-124).

Treatment of HPV neoplasias and cancers represents a large unmet medical need. The marketed vaccines Cervarix™ and Gardasil™ have proven effective in preventing new cases of HPV infection, and hold promise for reduction in the rates of cervical cancer in the future (reviewed in Darus, C. J. Mueller, J. J., *Clin. Obstet. Gynecol.* 2013; 56:10-16). However, these vaccines are not effective as therapeutics for the treatment of cervical cancer. Additionally, poor uptake of the vaccines in some markets, such as the US, means that high risk HPV infections, and resulting cervical cancers, will continue to be a concern. Small molecule inhibitors of the HPV E1/E2 protein complex have been identified, but most are highly HPV type specific and target low risk HPV types (Wang, Y., Coulombe, T., Cameron, D. R., et al *J. Biol. Chem.* 2004; 279:6976-6985)

(White, P. W., Faucher, A. M., Massariol, M. J., et al. *Antimicrob. Agents Chemother.* 2005; 49: 4834-4842). Although the HPV E1 and E2 proteins are important for initial replication of the HPV genome, these gene products are no longer required to maintain cellular transformation after integration, and therefore these potential treatments would not be useful in later stages of neoplasia (Munger, K., Phelps, W. C., Bubb, V., Howley, P. M., Schlegel, R. *J. Virol.* 1989; 63:4417-4421). When high grade HPV neoplasias are identified in the cervix, current standard of care involves surgical excision of the lesion, known as a loop electrosurgical excision procedure (LEEP) (Massad, L. S., Einstein, M. H., Huh, W. K., et al. J. Low Genit. Tract Dis. 2013; 17:S1-S27). The LEEP procedure is invasive and is not without an increased risk of unwanted side effects including hemorrhage, infection, and potential weakening of the cervix which may affect a woman's ability to carry future pregnancies to term (Samson S L, Bentley J R, Fahey T J, McKay D J, Gill G H. *Obstet Gynecol* 2005; 105:325-332). Incomplete excision can also result in recurrence of the neoplasia.

Increasing evidence also strongly links HPV with cancers of the anus, vulva, vagina, and penis (Bruni L., Barrionuevo-Rosas L., Serran B., Brotons M., Cosano R., Munoz J., Bosch F. X., de Sanjose S., Castellsague X. ICO Information Centre on HPV and Cancer (HPV Information Centre). *Human Papillomavirus and Related Diseases in World.* Summary Report 2014-04-08. [Data Accessed2014-05-27]). Although less prevalent than cervical cancer, their association with HPV suggests these cancers might also be treatable by therapeutics that target HPV-related cervical cancer.

There are currently no marketed small molecule inhibitors specific for HPV. Identification of an inhibitor that could selectively kill HPV-transformed cells would therefore be of great benefit in the treatment of HPV-related cancers. Desired in the art are compounds having anti-proliferative activity selective for cells transformed by human Papilloma virus (HPV), a virus strongly associated with a number of different cancers.

BRIEF DESCRIPTION OF THE DRAWINGS

The invention is illustrated by reference to the accompanying drawings described below.

FIG. 1 shows the activity of Example 15 in the Caspase-3/7 assay. Example 15 inhibited the proliferation of cell lines transformed by HPV-16 (Caski cells or SiHa cells) or by HPV-18 (Hela cells or SCHPV-18 cells) compared to HPV-negative cell lines (Saos-2, C33a, HaCat, or C33a).

SUMMARY OF THE INVENTION

It has been found that aryl substituted heteroaryl compounds in accordance with the present invention are PAR4 antagonists which inhibit platelet aggregation in gamma-thrombin induced platelet aggregation assays. Accordingly, the present invention provides aryl substituted heteroaryl compounds which are PAR4 antagonists and are useful as selective inhibitors of platelet aggregation, including stereoisomers, tautomers, pharmaceutically acceptable salts, solvates, or prodrugs thereof.

It has also been found that certain aryl substituted heteroaryl compounds in accordance with the present invention are selective inhibitors of the replication of HPV-transformed cells. Accordingly, the present invention provides aryl substituted heteroaryl compounds which have anti-proliferative activity for cells transformed by HPV, including stereoisomers, tautomers, pharmaceutically acceptable salts, solvates, or prodrugs thereof.

The present invention also provides processes and intermediates for making the compounds of the present invention or stereoisomers, tautomers, pharmaceutically acceptable salts, solvates, or prodrugs thereof.

The present invention also provides pharmaceutical compositions comprising a pharmaceutically acceptable carrier and at least one of the compounds of the present invention or stereoisomers, tautomers, pharmaceutically acceptable salts, solvates, or prodrugs thereof.

The present invention also provides a method for the treatment or prophylaxis of thromboembolic disorders comprising administering to a patient in need of such treatment or prophylaxis a therapeutically effective amount of at least one of the compounds of the present invention or stereoisomers, tautomers, pharmaceutically acceptable salts, solvates, or prodrugs thereof.

The present invention also provides a method for the treatment of human papillomavirus comprising administering to a patient in need of such treatment a therapeutically effective amount of at least one of the compounds of the present invention or stereoisomers, tautomers, pharmaceutically acceptable salts, solvates, or prodrugs thereof.

The present invention also provides the compounds of the present invention or stereoisomers, tautomers, pharmaceutically acceptable salts, solvates, or prodrugs thereof, for use in therapy.

The present invention also provides the use of the compounds of the present invention or stereoisomers, tautomers, pharmaceutically acceptable salts, solvates, or prodrugs thereof, for the manufacture of a medicament for the treatment or prophylaxis of a thromboembolic disorder.

The present invention also provides the use of the compounds of the present invention or stereoisomers, tautomers, pharmaceutically acceptable salts, solvates, or prodrugs thereof, for the manufacture of a medicament for the treatment of the human papillomavirus.

Other features and advantages of the invention will be apparent from the following detailed description and claims.

DETAILED DESCRIPTION

The first aspect of the present invention provides at least one compound of Formula (I):

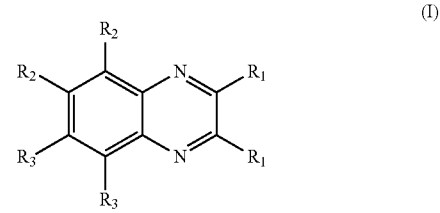

or a stereoisomer, tautomer, pharmaceutically acceptable salt, solvate or prodrug thereof, wherein:
one $R_1$ is H and the other $R_1$ is F, Cl, —OH, $C_{1-4}$ alkyl, $C_{1-4}$ fluoroalkyl, $C_{2-4}$ alkenyl, $C_{2-4}$ alkynyl, $C_{3-7}$ cycloalkyl, $C_{3-7}$ fluorocycloalkyl, $C_{1-3}$ alkoxy, $C_{1-3}$ fluoroalkoxy, $C_{2-4}$ hydroxyalkoxy, $C_{3-6}$ cycloalkoxy, ($C_{1-3}$ alkoxy)-($C_{1-3}$ alkylene), ($C_{1-3}$ alkoxy)-($C_{1-3}$ fluoroalkylene), ($C_{1-3}$ deuteroalkoxy)-($C_{1-3}$ deuteroalkylene), ($C_{1-3}$ fluoroalkoxy)-($C_{1-3}$ alkylene), —(CH$_2$)$_{1-3}$O(phenyl), —(CH$_2$)$_{1-3}$NR$_a$R$_a$, —C(O)O(C$_{1-6}$ alkyl), —C(O)NR$_a$R$_a$, —C(O)NR$_b$R$_b$, —NH$_2$, —NH(C$_{1-6}$ alkyl), —N(C$_{1-6}$ alkyl)$_2$, azetidin-1-yl, pyrrolidin-1-yl, furanyl, pyranyl, piperidin-1-yl, morpholin-4-yl, piperazin-1-yl, —S(O)$_2$(C$_{1-3}$ alkyl), —S(O)$_2$NR$_a$R$_a$, or C$_{1-3}$ alkylthio;

one R$_2$ is H and the other R$_2$ is H, F, Cl, Br, —OH. —CN, C$_{1-4}$ alkyl, C$_{1-4}$ fluoroalkyl, C$_{1-4}$ hydroxyalkyl, C$_{1-3}$ aminoalkyl, C$_{2-4}$ alkenyl, C$_{2-4}$ alkynyl, C$_{3-7}$ cycloalkyl, C$_{3-7}$ fluorocycloalkyl, C$_{1-6}$ alkoxy, C$_{1-3}$ fluoroalkoxy, C$_{1-3}$ alkylthio, (C$_{1-3}$ alkoxy)-(C$_{1-3}$ alkylene), (C$_{1-3}$ fluoroalkoxy)-(C$_{1-3}$ alkylene), —C(O)NH$_2$, —C(O)NH(C$_{1-6}$ alkyl), —C(O)N (C$_{1-6}$ alkyl)$_2$, —C(O)NR$_b$R$_b$, —C(O)O(C$_{1-6}$ alkyl), —CH (OH)(C$_{3-6}$ cycloalkyl), —CH(OH)(phenyl), —S(O)$_2$(C$_{1-3}$ alkyl), —S(O)$_2$NR$_a$R$_a$, or a cyclic group selected from phenyl, 5- to 6-membered heteroaryl, and 5- to 7-membered heterocycle, wherein said cyclic group is substituted with zero to 5 substituents independently selected from F, Cl, C$_{1-3}$ alkoxy, and —CN;

one R$_3$ is H and the other R$_3$ is an aryl group substituted with zero to 3 R$_{3a}$; R$_{3a}$, at each occurrence, is independently: (i) H, F, Cl, Br, —CN, —OH, C$_{1-3}$ alkyl, C$_{1-3}$ fluoroalkyl, C$_{1-6}$ hydroxyalkyl, C$_{1-6}$ alkoxy, C$_{1-3}$ fluoroalkoxy, C$_{3-6}$ cycloalkyl, C$_{3-6}$ fluorocycloalkyl, 3- to 6-membered heterocyclyl, —CH(OH)(C$_{3-6}$ cycloalkyl), —CH(OH)(aryl), —CH(OH)(heteroaryl), (C$_{1-3}$ alkoxy)-(C$_{1-3}$ alkylene), —(CH$_2$)$_{1-3}$NR$_a$R$_a$, —(CH$_2$)$_{1-3}$NHS(O)$_2$(aryl), —O(CH$_2$)$_{1-3}$(aryl), —O(CH$_2$)$_{1-3}$(thiazolyl), —O(C$_{1-6}$ hydroxyalkyl), (C$_{1-3}$ alkoxy)-(C$_{1-6}$ alkoxy), —O(CH$_2$)$_{1-4}$O(aryl), —O(CH$_2$)$_{1-4}$O(CH$_2$)$_{1-3}$(aryl), —O(CH$_2$)$_{1-4}$NR$_a$R$_a$, —O(CH$_2$)$_{1-4}$NHS(O)$_2$(C$_{1-3}$ alkyl), —O(CH$_2$)$_{1-4}$NHS(O)$_2$ (aryl), —O(CH$_2$)$_{1-4}$C(O)OH, —O(CH$_2$)$_{1-4}$C(O)O(C$_{1-6}$ alkyl), —O(CH$_2$)$_{1-4}$C(O)NR$_a$(CH$_2$)$_{0-3}$(aryl), —O(CH$_2$)$_{1-4}$C (O)(morpholinyl), —O(CH$_2$)$_{1-4}$OC(O)O(C$_{1-3}$ alkyl), —O(CH$_2$)$_{1-3}$CHR$_a$OC(O)NR$_a$(CH$_2$)$_{1-4}$C(O)NR$_a$R$_a$, —O(CH$_2$)$_{1-4}$OC(O)NR$_a$(heteroaryl), —O(imidazolyl substituted with aryl), —C(O)OH, —C(O)O(C$_{1-6}$ alkyl), —NR$_a$C(O)(furanyl), —NR$_a$C(O)(pyranyl), —NR$_a$C(O)O (C$_{1-6}$ alkyl), —NR$_a$C(O)O(CH$_2$)$_{1-4}$(aryl), —O(CH$_2$)$_{1-4}$ NR$_a$C(O)O(C$_{1-6}$ alkyl), —O(CH$_2$)$_{1-4}$NR$_a$C(O)O(CH$_2$)$_{1-4}$ (pyranyl), —O(CH$_2$)$_{1-4}$NR$_a$C(O)O(CH$_2$)$_{1-4}$(aryl), or —O(CH$_2$)$_{1-4}$NR$_a$C(O)O(CH$_2$)$_{1-4}$(furanyl), wherein each of said aryl or heteroaryl is substituted with zero to 5 substituents independently selected from F, Cl, —CN, C$_{1-3}$ alkyl, C$_{1-3}$ fluoroalkyl, C$_{1-4}$ hydroxyalkyl, C$_{1-3}$ alkoxy, —OCF$_3$, —OCHF$_2$, —NH$_2$, —NH(C$_{1-6}$ alkyl), —N(C$_{1-6}$ alkyl)$_2$, C$_{1-3}$ hydroxyalkoxy, —CONR$_c$R$_c$, and —S(O)$_2$NR$_c$R$_c$;

(ii) —O(CH$_2$)$_{1-4}$NR$_a$S(O)$_2$R$_w$, wherein R$_w$ is aryl or heteroaryl substituted with zero to 2 substituents independently selected from F, Cl, —CN, C$_{1-3}$ alkyl, C$_{1-3}$ alkoxy, —OCF$_3$, —OCHF$_2$, and C$_{1-3}$ fluoroalkyl; or (iii) —O(CH$_2$)$_{1-4}$OC(O)NR$_a$R$_x$, —OCH(R$_d$)(CH$_2$)$_{1-3}$OC (O)NR$_a$R$_x$, —O(CH$_2$)$_{1-3}$CH(R$_d$)OC(O)NR$_a$R$_x$, or —OCH(R$_d$)CH(R$_d$) (CH$_2$)$_{0-2}$OC(O)NR$_a$R$_x$, wherein R$_x$ is selected from H, C$_{1-4}$ alkyl, C$_{1-4}$ fluoroalkyl, aryl, heteroaryl, and —CH$_2$(heteroaryl), each aryl and heteroaryl substituted with zero to 2 substituents independently selected from F, Cl, —CN, C$_{1-3}$alkyl, C$_{1-3}$ fluoroalkyl, C$_{1-6}$ hydroxyalkyl, C$_{1-6}$ hydroxyalkoxy, C$_{1-3}$ alkoxy, —C(O)O(C$_{1-3}$ alkyl), —C(O) NH$_2$, —C(O)NH(C$_{1-6}$ alkyl), —C(O)N(C$_{1-6}$ alkyl)$_2$, —C(O) NR$_a$(C$_{1-6}$ hydroxyalkyl), —C(O)NR$_a$R$_a$, —C(O)NR$_b$R$_b$, —S(O)$_2$NR$_a$R$_a$, and methyl triazolyl;

R$_a$, at each occurrence, is independently H or —CH$_3$;
two R$_b$ along with the nitrogen atom to which they are attached form a 4- to 7-membered heterocyclo ring;

R$_c$, at each occurrence, is independently C$_{1-3}$ alkyl or C$_{1-3}$ hydroxyalkyl or two R$_c$ along with the nitrogen atom to which they are attached form a monocyclic or a bicyclic heterocyclyl; and R$_d$, at each occurrence, is independently C$_{1-4}$ alkyl, fluoroalkyl, C$_{1-6}$ hydroxyalkyl, (C$_{1-3}$ alkoxy)-(C$_{1-3}$ alkylene), (C$_{1-2}$ fluoroalkyl)-O—(C$_{1-2}$ alkylene), (C$_{3-6}$ cycloalkyl)-(C$_{0-2}$ alkylene), aryl(C$_{1-2}$ alkylene), heteroaryl(C$_{1-2}$ alkylene), aryl-O—(C$_{1-2}$ alkylene), or heteroaryl-O—(C$_{1-2}$ alkylene);

with the proviso that the compound is not:

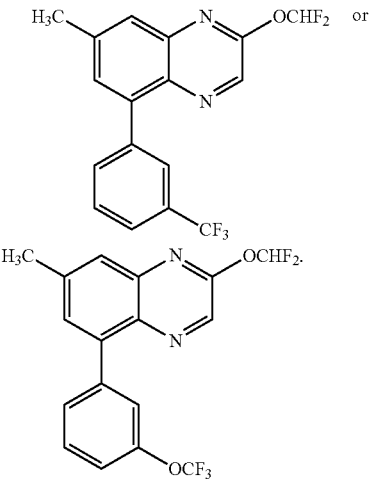

The second aspect of the present invention provides a pharmaceutical composition comprising a pharmaceutically acceptable carrier and a compound of Formula (I):

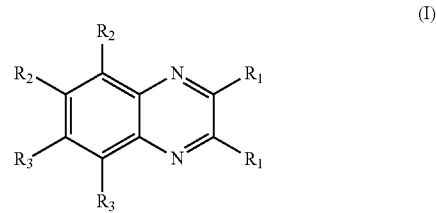

or a stereoisomer, tautomer, pharmaceutically acceptable salt, solvate or prodrug thereof, wherein:

one R$_1$ is H and the other R$_1$ is H is F, Cl, —OH, C$_{1-4}$ alkyl, C$_{1-4}$ fluoroalkyl, C$_{2-4}$ alkenyl, C$_{2-4}$ alkynyl, C$_{3-7}$ cycloalkyl, C$_{3-7}$ fluorocycloalkyl, C$_{1-3}$ alkoxy, C$_{1-3}$ fluoroalkoxy, C$_{2-4}$ hydroxyalkoxy, C$_{3-6}$ cycloalkoxy, (C$_{1-3}$ alkoxy)-(C$_{1-3}$ alkylene), (C$_{1-3}$ alkoxy)-(C$_{1-3}$ fluoroalkylene), (C$_{1-3}$ deuteroalkoxy)-(C$_{1-3}$ deuteroalkylene), (C$_{1-3}$ fluoroalkoxy)-(C$_{1-3}$ alkylene), —(CH$_2$)$_{1-3}$O(phenyl), —(CH$_2$)$_{1-3}$ NR$_a$R$_a$, —C(O)O(C$_{1-6}$ alkyl), —C(O)NR$_a$R$_a$, —C(O) NR$_b$R$_b$, —NH$_2$, —NH(C$_{1-6}$ alkyl), —N(C$_{1-6}$ alkyl)$_2$, azetidin-1-yl, pyrrolidin-1-yl, furanyl, pyranyl, piperidin-1-yl, morpholin-4-yl, piperazin-1-yl, —S(O)$_2$(C$_{1-3}$ alkyl), —S(O)$_2$ NR$_a$R$_a$, or C$_{1-3}$ alkylthio;

one R$_2$ is H and the other R$_2$ is H, F, Cl, Br, —OH, —CN, C$_{1-4}$ alkyl, C$_{1-4}$ fluoroalkyl, C$_{1-4}$ hydroxyalkyl, C$_{1-3}$ aminoalkyl, C$_{2-4}$ alkenyl, C$_{2-4}$ alkynyl, C$_{3-7}$ cycloalkyl, C$_{3-7}$ fluorocycloalkyl, C$_{1-6}$ alkoxy, C$_{1-3}$ fluoroalkoxy, C$_{1-3}$ alkylthio, (C$_{1-3}$ alkoxy)-(C$_{1-3}$ alkylene), (C$_{1-3}$ fluoroalkoxy)-(C$_{1-3}$ alkylene), —C(O)NH$_2$, —C(O)NH(C$_{1-6}$ alkyl), —C(O)N (C$_{1-6}$ alkyl)$_2$, —C(O)NR$_b$R$_b$, —C(O)O(C$_{1-6}$ alkyl), —CH(OH)(C$_{3-6}$ cycloalkyl), —CH(OH)(phenyl), —S(O)$_2$(C$_{1-3}$ alkyl), —S(O)$_2$NR$_a$R$_a$, or a cyclic group selected from phenyl, 5- to 6-membered heteroaryl, and 5- to 7-membered heterocycle, wherein said cyclic group is substituted with zero to 5 substituents independently selected from F, Cl, C$_{1-3}$ alkoxy, and —CN:

one R$_3$ is H and the other R$_3$ is an aryl group substituted with zero to 3 R$_{3a}$;

R$_{3a}$, at each occurrence, is independently:
(i) H, F, Cl, Br, —CN, —OH, C$_{1-3}$ alkyl, C$_{1-3}$ fluoroalkyl, C$_{1-6}$ hydroxyalkyl, C$_{1-6}$ alkoxy, C$_{1-3}$ fluoroalkoxy, C$_{3-6}$ cycloalkyl, C$_{3-6}$ fluorocycloalkyl, 3- to 6-membered heterocyclyl, —CH(OH)(C$_{3-6}$ cycloalkyl), —CH(OH)(aryl), —CH(OH)(heteroaryl), (C$_{1-3}$ alkoxy)-(C$_{1-3}$ alkylene), —(CH$_2$)$_{1-3}$NR$_a$R$_a$, —(CH$_2$)$_{1-3}$NHS(O)$_2$(aryl), —O(CH$_2$)$_{1-3}$(aryl), —O(CH$_2$)$_{1-3}$(thiazolyl), —O(C$_{1-6}$ hydroxyalkyl), (C$_{1-3}$ alkoxy)-(C$_{1-6}$ alkoxy), —O(CH$_2$)$_{1-4}$O(aryl), —O(CH$_2$)$_{1-4}$O(CH$_2$)$_{1-3}$(aryl), —O(CH$_2$)$_{1-4}$NR$_a$R$_a$, —O(CH$_2$)$_{1-4}$NHS(O)$_2$(C$_{1-3}$ alkyl), —O(CH$_2$)$_{1-4}$NHS(O)$_2$(aryl), —O(CH$_2$)$_{1-4}$C(O)OH, —O(CH$_2$)$_{1-4}$C(O)O(C$_{1-6}$ alkyl), —O(CH$_2$)$_{1-4}$C(O)NR$_a$(CH$_2$)$_{0-3}$(aryl), —O(CH$_2$)$_{1-4}$C(O)(morpholinyl), —O(CH$_2$)$_{1-4}$OC(O)O(C$_{1-3}$ alkyl), —O(CH$_2$)$_{1-3}$CHR$_a$OC(O)NR$_a$CH$_2$)$_{1-4}$C(O)NR$_a$R$_a$, —O(CH$_2$)$_{1-4}$OC(O)NR$_a$(heteroaryl), —O(imidazolyl substituted with aryl), —C(O)OH, —C(O)O(C$_{1-6}$ alkyl), —NR$_a$C(O)(furanyl), —NR$_a$C(O)(pyranyl), —NR$_a$C(O)O(C$_{1-6}$ alkyl), —NR$_a$C(O)O(CH$_2$)$_{1-4}$(aryl), —O(CH$_2$)$_{1-4}$NR$_a$C(O)O(C$_{1-6}$ alkyl), —O(CH$_2$)$_{1-4}$NR$_a$C(O)O(CH$_2$)$_{1-4}$(pyranyl), —O(CH$_2$)$_{1-4}$NR$_a$C(O)O(CH$_2$)$_{1-4}$(aryl), or —O(CH$_2$)$_{1-4}$NR$_a$C(O)O(CH$_2$)$_{0-4}$(furanyl), wherein each of said aryl or heteroaryl is substituted with zero to 5 substituents independently selected from F, Cl, —CN, C$_{1-3}$ alkyl, C$_{1-3}$ fluoroalkyl, C$_{1-4}$ hydroxyalkyl, C$_{1-3}$ alkoxy, —OCF$_3$, —OCHF$_2$, —NH$_2$, —NH(C$_{1-6}$ alkyl), —N(C$_{1-6}$ alkyl)$_2$, C$_{1-3}$ hydroxyalkoxy, —CONR$_c$R$_c$, and —S(O)$_2$NR$_c$R$_c$;

(ii) —O(CH$_2$)$_{1-4}$NR$_a$S(O)$_2$R$_w$, wherein R$_w$ is aryl or heteroaryl substituted with zero to 2 substituents independently selected from F, Cl, —CN, C$_{1-3}$ alkyl, C$_{1-3}$ alkoxy, —OCF$_3$, —OCHF$_2$, and C$_{1-3}$ fluoroalkyl; or (iii) —O(CH$_2$)$_{1-4}$OC(O)NR$_a$R$_x$, —OCH(R$_d$)(CH$_2$)$_{1-3}$OC(O)NR$_a$R$_x$, —O(CH$_2$)$_{1-3}$CH(R$_d$)OC(O)NR$_a$R$_x$, or —OCH(R$_d$)CH(R$_d$)(CH$_2$)$_{0-2}$OC(O)NR$_a$R$_x$, wherein R$_x$ is selected from H, C$_{1-4}$ alkyl, C$_{1-4}$ fluoroalkyl, aryl, heteroaryl, and —CH$_2$(heteroaryl), each aryl and heteroaryl substituted with zero to 2 substituents independently selected from F, Cl, —CN, C$_{1-3}$ alkyl, C$_{1-3}$ fluoroalkyl, C$_{1-6}$ hydroxyalkyl, C$_{1-6}$ hydroxyalkoxy, C$_{1-3}$ alkoxy, —C(O)O(C$_{1-3}$ alkyl), —C(O)NH$_2$, —C(O)NH(C$_{1-6}$ alkyl), —C(O)N(C$_{1-6}$ alkyl)$_2$, —C(O)NR$_a$(C$_{1-6}$ hydroxyalkyl), —C(O)NR$_a$R$_a$, —C(O)NR$_b$R$_b$, —S(O)$_2$ NR$_a$R$_a$, and methyl triazolyl;

R$_a$, at each occurrence, is independently H or —CH$_3$;

two R$_b$ along with the nitrogen atom to which they are attached form a 4- to 7-membered heterocyclo ring:

R$_c$, at each occurrence, is independently C$_{1-3}$ alkyl or C$_{1-3}$ hydroxyalkyl or two Re along with the nitrogen atom to which they are attached form a monocyclic or a bicyclic heterocyclyl; and R$_d$, at each occurrence, is independently C$_{1-6}$ alkyl, fluoroalkyl, C$_{1-6}$ hydroxyalkyl, (C$_{1-3}$ alkoxy)-(C$_{1-3}$ alkylene), (C$_{1-2}$ fluoroalkyl)-O—(C$_{1-2}$ alkylene), (C$_{3-6}$ cycloalkyl)-(C$_{0-2}$ alkylene), aryl(C$_{1-2}$ alkylene), heteroaryl(C$_{1-2}$ alkylene), aryl-O—(C$_{1-2}$ alkylene), or heteroaryl-O—(C$_{1-2}$ alkylene).

The third aspect of the present invention provides a method for the treatment of a thromboembolic disorder or the primary prophylaxis of a thromboembolic disorder, comprising the steps of administering to a patient in need thereof a therapeutically effective amount of a compound of Formula (I):

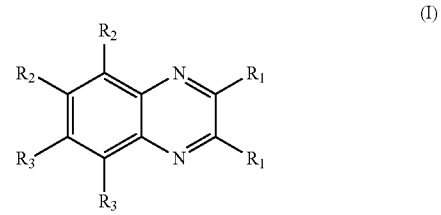

or a pharmaceutically acceptable salt thereof, wherein:
one R$_1$ is H and the other R$_1$ is F, Cl, —OH, C$_{1-4}$ alkyl, C$_{1-4}$ fluoroalkyl, C$_{2-4}$ alkenyl, C$_{2-4}$ alkynyl, C$_{3-7}$ cycloalkyl, C$_{3-7}$ fluorocycloalkyl, C$_{1-3}$ alkoxy, C$_{1-3}$ fluoroalkoxy, C$_{2-4}$ hydroxyalkoxy, C$_{3-6}$ cycloalkoxy, (C$_{1-3}$ alkoxy)-(C$_{1-3}$ alkylene), (C$_{1-3}$ alkoxy)-(C$_{1-3}$ fluoroalkylene), (C$_{1-3}$ deuteroalkoxy)-(C$_{1-3}$ deuteroalkylene), (C$_{1-3}$ fluoroalkoxy)-(C$_{1-3}$ alkylene), —(CH$_2$)$_{1-3}$O(phenyl), —(CH$_2$)$_{1-3}$NR$_a$R$_a$, —C(O)O(C$_{1-6}$ alkyl), —C(O)NR$_a$R$_a$, —C(O)NR$_b$R$_b$, —NH$_2$, —NH(C$_{1-6}$ alkyl), —N(C$_{1-6}$ alkyl)$_2$, azetidin-1-yl, pyrrolidin-1-yl, furanyl, pyranyl, piperidin-1-yl, morpholin-4-yl, piperazin-1-yl, —S(O)$_2$(C$_{1-3}$ alkyl), —S(O)$_2$NR$_a$R$_a$, or C$_{1-3}$ alkylthio;

one R$_2$ is H and the other R$_2$ is H, F, Cl, Br, —OH, —CN, C$_{1-4}$ alkyl, C$_{1-4}$ fluoroalkyl, C$_{1-4}$ hydroxyalkyl, C$_{1-3}$ aminoalkyl, C$_{2-4}$ alkenyl, C$_{2-4}$ alkynyl, C$_{3-7}$ cycloalkyl, C$_{3-7}$ fluorocycloalkyl, C$_{1-6}$ alkoxy, C$_{1-3}$ fluoroalkoxy, C$_{1-3}$ alkylthio, (C$_{1-3}$ alkoxy)-(C$_{1-3}$ alkylene), (C$_{1-3}$ fluoroalkoxy)-(C$_{1-3}$ alkylene), —C(O)NH$_2$, —C(O)NH(C$_{1-6}$ alkyl), —C(O)N(C$_{1-6}$ alkyl)$_2$, —C(O)NR$_b$R$_b$, —C(O)O(C$_{1-6}$ alkyl), —CH(OH)(C$_{3-6}$ cycloalkyl), —CH(OH)phenyl), —S(O)$_2$(C$_{1-3}$ alkyl), —S(O)$_2$NR$_a$R$_a$, or a cyclic group selected from phenyl, 5- to 6-membered heteroaryl, and 5- to 7-membered heterocycle, wherein said cyclic group is substituted with zero to 5 substituents independently selected from F, Cl, C$_{1-3}$ alkoxy, and —CN;

one R$_3$ is H and the other R$_3$ is an aryl group substituted with zero to 3 R$_{3a}$;

R$_{3a}$, at each occurrence, is independently:
(i) H, F, Cl, Br, —CN, —OH, C$_{1-3}$ alkyl, C$_{1-3}$ fluoroalkyl, C$_{1-6}$ hydroxyalkyl, C$_{1-6}$ alkoxy, C$_{1-3}$ fluoroalkoxy, C$_{3-6}$ cycloalkyl, C$_{3-6}$ fluorocycloalkyl, 3- to 6-membered heterocyclyl, —CH(OH)(C$_{3-6}$ cycloalkyl), —CH(OH)(aryl), —CH(OH)(heteroaryl), (C$_{1-3}$ alkoxy)-(C$_{1-3}$ alkylene), —(CH$_2$)$_{1-3}$NR$_a$R$_a$, —(CH$_2$)$_{1-3}$NHS(O)$_2$(aryl), —O(CH$_2$)$_{1-3}$(aryl), —O(CH$_2$)$_{1-3}$(thiazolyl), —O(C$_{1-6}$ hydroxyalkyl), (C$_{1-3}$ alkoxy)-(C$_{1-6}$ alkoxy), —O(CH$_2$)$_{1-4}$O(aryl), —O(CH$_2$)$_{1-4}$O(CH$_2$)$_{1-3}$(aryl), —O(CH$_2$)$_{1-4}$NR$_a$R$_a$, —O(CH$_2$)$_{1-4}$NHS(O)$_2$(C$_{1-3}$ alkyl), —O(CH$_2$)$_{1-4}$NHS(O)$_2$(aryl), —O(CH$_2$)$_{1-4}$C(O)OH, —O(CH$_2$)$_{1-4}$C(O)O(C$_{1-6}$ alkyl), —O(CH$_2$)$_{1-4}$C(O)NR$_a$(CH$_2$)$_{0-3}$(aryl), —O(CH$_2$)$_{1-4}$C(O)(morpholinyl), —O(CH$_2$)$_{1-4}$OC(O)O(C$_{1-3}$ alkyl), —O(CH$_2$)$_{1-3}$CHR$_a$OC(O)NR$_a$(CH$_2$)$_{1-4}$C(O)NR$_a$R$_a$, —O(CH$_2$)$_{1-4}$OC(O)NR$_a$(heteroaryl), —O(imidazolyl substituted with aryl), —C(O)OH, —C(O)O(C$_{1-4}$ alkyl), —NR$_a$C(O)(furanyl), —NR$_a$C(O)(pyranyl), —NR$_a$C(O)O(C$_{1-6}$ alkyl), —NR$_a$C(O)O(CH$_2$)$_{1-4}$(aryl), —O(CH$_2$)$_{1-4}$NR$_a$C(O)O(C$_{1-6}$ alkyl), —O(CH$_2$)$_{1-4}$NR$_a$C(O)O(CH$_2$)$_{0-4}$(pyranyl), —O(CH$_2$)$_{1-4}$NR$_a$C(O)O(CH$_2$)$_{1-4}$(aryl), or —O(CH$_2$)$_{1-4}$NR$_a$C(O)O(CH$_2$)$_{1-4}$(furanyl), wherein each of said aryl or heteroaryl is substituted with zero to 5 substituents independently selected from F, Cl, —CN, $C_{1-3}$ alkyl, $C_{1-3}$ fluoroalkyl, $C_{1-4}$ hydroxyalkyl, $C_{1-3}$ alkoxy, —OCF$_3$, —OCHF$_2$, —NH$_2$, —NH($C_{1-6}$ alkyl), —N($C_{1-6}$ alkyl)$_2$, $C_{1-3}$ hydroxyalkoxy, —CONR$_c$R$_c$, and —S(O)$_2$NR$_c$R$_c$;

(ii) —O(CH$_2$)$_{1-4}$NR$_a$S(O)$_2$R$_w$, wherein R$_w$ is aryl or heteroaryl substituted with zero to 2 substituents independently selected from F, Cl, —CN, $C_{1-3}$ alkyl, $C_{1-3}$ alkoxy, —OCF$_3$, —OCHF$_2$, and $C_{1-3}$ fluoroalkyl; or (iii) —O(CH$_2$)$_{1-4}$OC(O)NR$_a$R$_x$, —OCH(R$_d$)(CH$_2$)$_{1-3}$OC(O)NR$_a$R$_x$, —O(CH$_2$)$_{1-3}$CH(R$_d$)OC(O)NR$_a$R$_x$, or —OCH(R$_d$)CH(R$_d$)(CH$_2$)$_{0-2}$OC(O)NR$_a$R$_x$, wherein R$_x$ is selected from H, $C_{1-4}$ alkyl, $C_{1-4}$ fluoroalkyl, aryl, heteroaryl, and —CH$_2$(heteroaryl), each substituted with zero to 2 substituents independently selected from F, Cl, —CN, $C_{1-3}$ alkyl, $C_{1-3}$ fluoroalkyl, $C_{1-6}$ hydroxyalkyl, $C_{1-6}$ hydroxyalkoxy, $C_{1-3}$ alkoxy, —C(O)O($C_{1-3}$ alkyl), —C(O)NH$_2$, —C(O)NH($C_{1-6}$ alkyl), —C(O)N($C_{1-6}$ alkyl)$_2$, —C(O)NR$_a$($C_{1-6}$ hydroxyalkyl), —C(O)NR$_a$R$_a$, —C(O)NR$_b$R$_b$, —S(O)$_2$NR$_a$R$_a$, and methyl triazolyl;

R$_a$, at each occurrence, is independently H or —CH$_3$;

two R$_b$ along with the nitrogen atom to which they are attached form a 4- to 7-membered heterocyclo ring;

R$_c$, at each occurrence, is independently $C_{1-3}$ alkyl or $C_{1-3}$ hydroxyalkyl or two R$_c$ along with the nitrogen atom to which they are attached form a monocyclic or a bicyclic heterocyclyl; and R$_d$, at each occurrence, is independently $C_{1-6}$ alkyl, fluoroalkyl, $C_{1-6}$ hydroxyalkyl, ($C_{1-3}$ alkoxy)-($C_{1-3}$ alkylene), ($C_{1-2}$ fluoroalkyl)-O—($C_{1-2}$ alkylene), ($C_{3-6}$ cycloalkyl)-($C_{0-2}$ alkylene), aryl($C_{1-2}$ alkylene), heteroaryl($C_{1-2}$ alkylene), aryl-O—($C_{1-2}$ alkylene), or heteroaryl-O—($C_{1-2}$ alkylene);

wherein the thromboembolic disorder is selected from the group consisting of arterial cardiovascular thromboembolic disorders, venous cardiovascular thromboembolic disorders, and thromboembolic disorders in the chambers of the heart or in the peripheral circulation.

The fourth aspect of the present invention provides a method of inhibiting or preventing platelet aggregation, comprising the step of administering to a subject in need thereof a therapeutically effective amount of a compound of Formula (I):

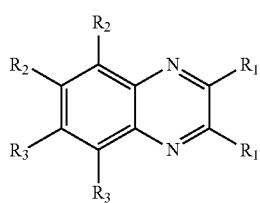

(I)

or a pharmaceutically acceptable salt thereof, wherein:

one R$_1$ is H and the other R$_1$ is F, Cl, —OH, $C_{1-4}$ alkyl, $C_{1-4}$ fluoroalkyl, $C_{2-4}$ alkenyl, $C_{2-4}$ alkynyl, $C_{3-7}$ cycloalkyl, $C_{3-7}$ fluorocycloalkyl, $C_{1-3}$ alkoxy, $C_{1-3}$ fluoroalkoxy, $C_{2-4}$ hydroxyalkoxy, $C_{1-6}$ cycloalkoxy, ($C_{1-3}$ alkoxy)-($C_{1-3}$ alkylene), ($C_{1-3}$ alkoxy)-($C_{1-3}$ fluoroalkylene), ($C_{1-3}$ deuteroalkoxy)-($C_{1-3}$ deuteroalkylene), ($C_{1-3}$ fluoroalkoxy)-($C_{1-3}$ alkylene), —(CH$_2$)$_{1-3}$O(phenyl), —(CH$_2$)$_{1-3}$NR$_a$R$_a$, —C(O)O($C_{1-6}$ alkyl), —C(O)NR$_a$R$_a$, —C(O)NR$_b$R$_b$, —NH$_2$, —NH($C_{1-6}$ alkyl), —N($C_{1-6}$ alkyl)$_2$, azetidin-1-yl, pyrrolidin-1-yl, furanyl, pyranyl, piperidin-1-yl, morpholin-4-yl, piperazin-1-yl, —S(O)$_2$($C_{1-3}$ alkyl), —S(O)$_2$NR$_a$R$_a$, or $C_{1-3}$ alkylthio;

one R$_2$ is H and the other R$_2$ is H, F, Cl, Br, —OH, —CN, $C_{1-4}$ alkyl, $C_{1-4}$ fluoroalkyl, $C_{1-4}$ hydroxyalkyl, $C_{1-3}$ aminoalkyl, $C_{2-4}$ alkenyl, $C_{2-4}$ alkynyl, $C_{3-7}$ cycloalkyl, $C_{3-7}$ fluorocycloalkyl, $C_{1-6}$ alkoxy, $C_{1-3}$ fluoroalkoxy, $C_{1-3}$ alkylthio, ($C_{1-3}$ alkoxy)-($C_{1-3}$ alkylene), ($C_{1-3}$ fluoroalkoxy)-($C_{1-3}$ alkylene), —C(O)NH$_2$, —C(O)NH($C_{1-6}$ alkyl), —C(O)N($C_{1-6}$ alkyl)$_2$, —C(O)NR$_b$R$_b$, —C(O)O($C_{1-6}$ alkyl), —CH(OH)($C_{3-6}$ cycloalkyl), —CH(OH)phenyl), —S(O)$_2$($C_{1-3}$ alkyl), —S(O)$_2$NR$_a$R$_a$, or a cyclic group selected from phenyl, 5- to 6-membered heteroaryl, and 5- to 7-membered heterocycle, wherein said cyclic group is substituted with zero to 5 substituents independently selected from F, Cl, $C_{1-3}$ alkoxy, and —CN;

one R$_3$ is H and the other R$_3$ is an aryl group substituted with zero to 3 R$_{3a}$;

R$_{3a}$, at each occurrence, is independently:

(i) H, F, Cl, Br, —CN, —OH, $C_{1-3}$ alkyl, $C_{1-3}$ fluoroalkyl, $C_{1-6}$ hydroxyalkyl, $C_{1-6}$ alkoxy, $C_{1-3}$ fluoroalkoxy, $C_{3-6}$ cycloalkyl, $C_{1-6}$ fluorocycloalkyl, 3- to 6-membered heterocyclyl, —CH(OH)($C_{1-6}$ cycloalkyl), —CH(OH)(aryl), —CH(OH)(heteroaryl), ($C_{1-3}$ alkoxy)-($C_{1-3}$ alkylene), —(CH$_2$)$_{1-3}$NR$_a$R$_a$, —(CH$_2$)$_{1-3}$NHS(O)$_2$(aryl), —O(CH$_2$)$_{1-3}$(aryl), —O(CH$_2$)$_{1-3}$(thiazolyl), —O($C_{1-6}$ hydroxyalkyl), ($C_{1-3}$ alkoxy)-($C_{1-6}$ alkoxy), —O(CH$_2$)$_{1-4}$O(aryl), —O(CH$_2$)$_{1-4}$O(CH$_2$)$_{1-3}$(aryl), —O(CH$_2$)$_{1-4}$NR$_a$R$_a$, —O(CH$_2$)$_{1-4}$NHS(O)$_2$($C_{1-3}$ alkyl), —O(CH$_2$)$_{1-4}$NHS(O)$_2$(aryl), —O(CH$_2$)$_{1-4}$C(O)OH, —O(CH$_2$)$_{1-4}$C(O)O($C_{1-6}$ alkyl), —O(CH$_2$)$_{1-4}$C(O)NR$_a$(CH$_2$)$_{0-3}$(aryl), —O(CH$_2$)$_{1-4}$C(O)(morpholinyl), —O(CH$_2$)$_{1-4}$OC(O)O($C_{1-3}$ alkyl), —O(CH$_2$)$_{1-3}$CHR$_d$OC(O)NR$_a$(CH$_2$)$_{1-4}$C(O)NR$_a$R$_a$, —O(CH$_2$)$_{1-4}$OC(O)NR$_a$(heteroaryl), —O(imidazolyl substituted with aryl), —C(O)OH, —C(O)O($C_{1-6}$ alkyl), —NR$_a$C(O)(furanyl), —NR$_a$C(O)(pyranyl), —NR$_a$C(O)O($C_{1-6}$ alkyl), —NR$_a$C(O)O(CH$_2$)$_{1-4}$(aryl), —O(CH$_2$)$_{1-4}$NR$_a$C(O)O($C_{1-6}$ alkyl), —O(CH$_2$)$_{1-4}$NR$_c$(O)O(CH$_2$)$_{1-4}$(pyranyl), —O(CH$_2$)$_{1-4}$NR$_a$C(O)O(CH$_2$)$_{0-4}$(aryl), or —O(CH$_2$)$_{1-4}$NR$_a$C(O)O(CH$_2$)$_{0-4}$(furanyl), wherein each of said aryl or heteroaryl is substituted with zero to 5 substituents independently selected from F, Cl, —CN, $C_{1-3}$ alkyl, $C_{1-3}$ fluoroalkyl, $C_{1-4}$ hydroxyalkyl, $C_{1-3}$ alkoxy, —OCF$_3$, —OCHF$_2$, —NH$_2$, —NH($C_{1-6}$ alkyl), —N($C_{1-6}$ alkyl)$_2$, $C_{1-3}$ hydroxyalkoxy, —CONR$_c$R$_c$, and —S(O)$_2$NR$_c$R$_c$;

(ii) —O(CH$_2$)$_{1-4}$NR$_a$S(O)$_2$R$_w$, wherein R$_w$ is aryl or heteroaryl substituted with zero to 2 substituents independently selected from F, Cl, —CN, $C_{1-3}$ alkyl, $C_{1-3}$ alkoxy, —OCF$_3$, —OCHF$_2$, and $C_{1-3}$ fluoroalkyl; or (iii) —O(CH$_2$)$_{1-4}$OC(O)NR$_a$R$_x$, —OCH(R$_d$)(CH$_2$)$_{1-3}$C(O)NR$_a$R$_x$, —O(CH$_2$)$_{1-3}$CH(R$_d$)OC(O)NR$_a$R$_x$, or —OCH(R$_d$)CH(R$_d$)(CH$_2$)$_{0-2}$C(O)NR$_a$R$_x$, wherein R$_x$ is selected from H, $C_{1-4}$ alkyl, $C_{1-4}$ fluoroalkyl, aryl, heteroaryl, and —CH$_2$(heteroaryl), each substituted with zero to 2 substituents independently selected from F, Cl, —CN, $C_{1-3}$ alkyl, $C_{1-3}$ fluoroalkyl, $C_{1-6}$ hydroxyalkyl, $C_{1-6}$ hydroxyalkoxy, $C_{1-3}$ alkoxy, —C(O)O($C_{1-3}$ alkyl), —C(O)NH$_2$, —C(O)NH($C_{1-6}$ alkyl), —C(O)N($C_{1-6}$ alkyl)$_2$, —C(O)NR$_a$($C_{1-6}$ hydroxyalkyl), —C(O)NR$_a$R$_a$, —C(O)NR$_b$R$_b$, —S(O)$_2$NR$_a$R$_a$, and methyl triazolyl;

R$_a$, at each occurrence, is independently H or —CH$_3$;

two R$_b$ along with the nitrogen atom to which they are attached form a 4- to 7-membered heterocyclo ring;

R$_c$, at each occurrence, is independently C$_{1-3}$ alkyl or C$_{1-3}$ hydroxyalkyl or two R along with the nitrogen atom to which they are attached form a monocyclic or a bicyclic heterocyclyl; and R$_d$, at each occurrence, is independently C$_{1-6}$ alkyl, fluoroalkyl, C$_{1-6}$ hydroxyalkyl, (C$_{1-3}$ alkoxy)-(C$_{1-3}$ alkylene), (C$_{1-2}$ fluoroalkyl)-O—(C$_{1-2}$ alkylene), (C$_{3-6}$ cycloalkyl)-(C$_{0-2}$ alkylene), aryl(C$_{1-2}$ alkylene), heteroaryl(C$_{1-2}$ alkylene), aryl-O—(C$_{1-2}$ alkylene), or heteroaryl-O—(C$_{1-2}$ alkylene).

The fifth aspect of the present invention provides a method for the treatment of human papillomavirus, comprising the steps of administering to a patient in need thereof a therapeutically effective amount of a compound of Formula (I):

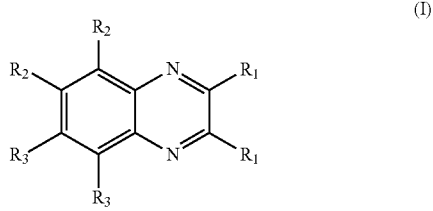

(I)

or a pharmaceutically acceptable salt thereof, wherein:

R$_1$ is F, Cl, —OH, C$_{1-4}$ alkyl, C$_{1-4}$ fluoroalkyl, C$_{2-4}$ alkenyl, C$_{2-4}$ alkynyl, C$_{3-7}$ cycloalkyl, C$_{3-7}$ fluorocycloalkyl, C$_{1-3}$ alkoxy, C$_{1-3}$ fluoroalkoxy, C$_{2-4}$ hydroxyalkoxy, C$_{3-6}$ cycloalkoxy, (C$_{1-3}$ alkoxy)-(C$_{1-3}$ alkylene), (C$_{1-3}$ alkoxy)-(C$_{1-3}$ fluoroalkylene), (C$_{1-3}$ deuteroalkoxy)-(C$_{1-3}$ deuteroalkylene), (C$_{1-3}$ fluoroalkoxy)-(C$_{1-3}$ alkylene), —(CH$_2$)$_{1-3}$O(phenyl), —(CH$_2$)$_{1-3}$NR$_a$R$_a$, —C(O)O(C$_{1-6}$ alkyl), —C(O)NR$_a$R$_a$, —C(O)NR$_b$R$_b$, —NH$_2$, —NH(C$_{1-6}$ alkyl), —N(C$_{1-6}$ alkyl)$_2$, azetidin-1-yl, pyrrolidin-1-yl, furanyl, pyranyl, piperidin-1-yl, morpholin-4-yl, piperazin-1-yl, —S(O)$_2$(C$_{1-3}$ alkyl), —S(O)$_2$NR$_a$R$_a$, or C$_{1-3}$ alkylthio;

R$_2$, at each occurrence, is independently H, F, Cl, Br, —OH, —CN, C$_{1-4}$ alkyl, C$_{1-4}$ fluoroalkyl, C$_{1-4}$ hydroxyalkyl, C$_{1-3}$ aminoalkyl, C$_{2-4}$ alkenyl, C$_{2-4}$ alkynyl, C$_{3-7}$ cycloalkyl, C$_{3-7}$ fluorocycloalkyl, C$_{1-6}$ alkoxy, C$_{1-3}$ fluoroalkoxy, C$_{1-3}$ alkylthio, (C$_{1-3}$ alkoxy)-(C$_{1-3}$ alkylene), (C$_{1-3}$ fluoroalkoxy)-(C$_{1-3}$ alkylene), —C(O)NH$_2$, —C(O)NH(C$_{1-6}$ alkyl), —C(O)N(C$_{1-6}$ alkyl)$_2$, —C(O)NR$_b$R$_b$, —C(O)O(C$_{1-6}$ alkyl), —CH(OH)(C$_{3-6}$ cycloalkyl), —CH(OH)(phenyl), —S(O)$_2$(C$_{1-3}$ alkyl), —S(O)$_2$NR$_a$R$_a$, or a cyclic group selected from phenyl, 5- to 6-membered heteroaryl, and 5- to 7-membered heterocycle, wherein said cyclic group is substituted with zero to 5 substituents independently selected from F, Cl, C$_{1-3}$ alkoxy, and —CN:

R$_3$ is an aryl group substituted with zero to 3 R$_{3a}$;

R$_{3a}$, at each occurrence, is independently:
(i) H, F, Cl, Br, —CN, —OH, C$_{1-3}$ alkyl, C$_{1-3}$ fluoroalkyl, C$_{1-6}$ hydroxyalkyl, C$_{1-6}$ alkoxy, C$_{1-3}$ fluoroalkoxy, C$_{3-6}$ cycloalkyl, C$_{3-6}$ fluorocycloalkyl, 3- to 6-membered heterocyclyl, —CH(OH)(C$_{3-6}$ cycloalkyl), —CH(OH)(aryl), —CH(OH)(heteroaryl), (C$_{1-3}$ alkoxy)-(C$_{1-3}$ alkylene), —(CH$_2$)$_{1-3}$NR$_a$R$_a$, —(CH$_2$)$_{1-3}$NHS(O)$_2$(aryl), —O(CH$_2$)$_{1-3}$(aryl), —O(CH$_2$)$_{1-3}$(thiazolyl), —O(C$_{1-6}$ hydroxyalkyl), (C$_{1-3}$ alkoxy)-(C$_{1-6}$ alkoxy), —O(CH$_2$)$_{1-4}$O(aryl), —O(CH$_2$)$_{1-4}$O(CH$_2$)$_{1-3}$(aryl), —O(CH$_2$)$_{1-4}$NR$_a$R$_a$, —O(CH$_2$)$_{1-4}$NHS(O)$_2$(C$_{1-3}$ alkyl), —O(CH$_2$)$_{1-4}$NHS(O)$_2$(aryl), —O(CH$_2$)$_{1-4}$C(O)OH, —O(CH$_2$)$_{1-4}$C(O)O(C$_{1-6}$ alkyl), —O(CH$_2$)$_{1-4}$C(O)NR$_a$(CH$_2$)$_{0-3}$(aryl), —O(CH$_2$)$_{1-4}$C(O)(morpholinyl), —O(CH$_2$)$_{1-4}$OC(O)O(C$_{1-3}$ alkyl), —O(CH$_2$)$_{1-3}$CHR$_a$OC(O)NR$_a$(CH$_2$)$_{1-4}$C(O)NR$_a$R$_a$, —O(CH$_2$)$_{1-4}$OC(O)NR$_a$(heteroaryl), —O(imidazolyl substituted with aryl), —C(O)OH, —C(O)O(C$_{1-6}$ alkyl), —NR$_a$C(O)(furanyl), —NR$_a$C(O)(pyranyl), —NR$_a$C(O)O(C$_{1-6}$ alkyl), —NR$_a$C(O)O(CH$_2$)$_{1-4}$(aryl), —O(CH$_2$)$_{1-4}$NR$_a$C(O)O(C$_{1-6}$ alkyl), —O(CH$_2$)$_{1-4}$NR$_a$C(O)O(CH$_2$)$_{1-4}$(pyranyl), —O(CH$_2$)$_{1-4}$NR$_a$C(O)O(CH$_2$)$_{0-4}$(aryl), or —O(CH$_2$)$_{1-4}$NR$_a$C(O)O(CH$_2$)$_{1-4}$(furanyl), wherein each of said aryl or heteroaryl is substituted with zero to 5 substituents independently selected from F, Cl, —CN, C$_{1-3}$ alkyl, C$_{1-3}$ fluoroalkyl, C$_{1-4}$ hydroxyalkyl, C$_{1-3}$ alkoxy, —OCF$_3$, —OCHF$_2$, —NH$_2$, —NH(C$_{1-6}$ alkyl), —N(C$_{1-6}$ alkyl)$_2$, C$_{1-3}$ hydroxyalkoxy, —CONR$_c$R$_c$, and —S(O)$_2$NR$_c$R$_c$;
(ii) —O(CH$_2$)$_{1-4}$NR$_a$S(O)$_2$R$_w$, wherein R$_w$ is aryl or heteroaryl substituted with zero to 2 substituents independently selected from F, Cl, —CN, C$_{1-3}$ alkyl, C$_{1-3}$ alkoxy, —OCF$_3$, —OCHF$_2$, and C$_{1-3}$ fluoroalkyl; or
(iii) —O(CH$_2$)$_{1-4}$OC(O)NR$_a$R$_x$, —OCH(R$_d$)(CH$_2$)$_{1-3}$OC(O)NR$_a$R$_x$, —O(CH$_2$)$_{1-3}$CH(R$_d$)OC(O)NR$_a$R$_x$, or —OCH(R$_d$)CH(R$_d$) (CH$_2$)$_{0-2}$OC(O)NR$_a$R$_x$, wherein R$_x$ is selected from H, C$_{1-4}$ alkyl, C$_{1-4}$ fluoroalkyl, aryl, pyrrolyl, pyrazolyl, thiazolyl, heteroaryl, pyridazinyl, pyrimidinyl, oxadiazolyl, thiadiazolyl, indolyl, pyrrolo[2,3-b]pyridinyl, benzo[d]oxazol-2 (3H)-onyl, and —CH$_2$(heteroaryl), each substituted with zero to 2 substituents independently selected from F, Cl, —CN. C$_{1-3}$ alkyl, C$_{1-3}$ fluoroalkyl, C$_{1-6}$ hydroxyalkyl, C$_{1-6}$ hydroxyalkoxy, C$_{1-3}$ alkoxy, —C(O)O(C$_{1-3}$ alkyl). —C(O)NH$_2$, —C(O)NH(C$_{1-6}$ alkyl), —C(O)N(C$_{1-6}$ alkyl)$_2$, —C(O)NR$_a$(C$_{1-6}$ hydroxyalkyl), —C(O)NR$_a$R$_a$, —C(O)NR$_b$R$_b$, —S(O)$_2$NR$_a$R$_a$, and methyl triazolyl;

R$_a$, at each occurrence, is independently H or —CH$_3$;

two R$_b$ along with the nitrogen atom to which they are attached form a 4- to 7-membered heterocyclo ring:

R$_c$, at each occurrence, is independently C$_{1-3}$ alkyl or C$_{1-3}$ hydroxyalkyl or two R$_c$ along with the nitrogen atom to which they are attached form a monocyclic or a bicyclic heterocyclyl; and R$_d$, at each occurrence, is independently C$_{1-6}$ alkyl, fluoroalkyl, C$_{1-6}$ hydroxyalkyl, (C$_{1-3}$ alkoxy)-(C$_{1-3}$ alkylene), (C$_{1-2}$ fluoroalkyl)-O—(C$_{1-2}$ alkylene), (C$_{3-6}$ cycloalkyl)-(C$_{0-2}$ alkylene), aryl(C$_{1-2}$ alkylene), heteroaryl(C$_{1-2}$ alkylene), aryl-O—(C$_{1-2}$ alkylene), or heteroaryl-O—(C$_{1-2}$ alkylene).

One embodiment provides a compound of Formula (I) or a salt thereof, having a structure of Formula (II) to (IV):

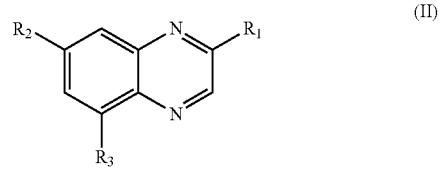

(II)

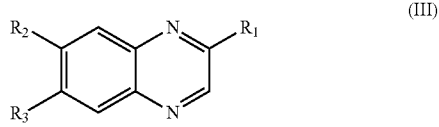

(III)

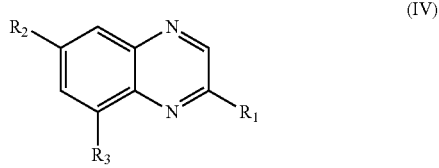

(IV)

or a salt thereof, wherein: $R_1$ is —OCH$_3$, —OCHF$_2$, or —CH$_2$OCH$_3$; $R_2$ is H, F, Cl, Br, —OH, —CN, $C_{1-3}$ alkyl, $C_{1-3}$ fluoroalkyl, $C_{1-3}$ hydroxyalkyl, $C_{2-4}$alkenyl, $C_{2-4}$alkynyl, or —C(O)O(C$_{1-6}$ alkyl); $R_3$ is phenyl or naphthalenyl substituted with zero to 2 $R_{3a}$; and $R_{3a}$, at each occurrence, is independently F, Cl, Br, $C_{1-3}$ alkyl, $C_{1-3}$ fluoroalkyl, $C_{1-3}$ alkoxy, or $C_{1-3}$ fluoroalkoxy, with the proviso that the compound is not:

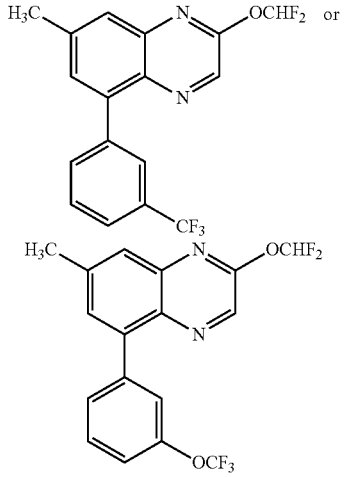

Included in this embodiment are compounds in which $R_1$ is —OCHF$_2$; $R_2$ is Cl, Br, —CN, —CH$_3$, —CF$_3$, —CH=CH$_2$, —C≡CH, or —C(O)OCH$_3$; $R_3$ is phenyl or naphthalenyl substituted with 1 or 2 $R_{3a}$; and $R_{3a}$, at each occurrence, is independently F, Cl, Br, —CH$_3$, —CF$_3$, —OCH$_3$, or —OCF$_3$. Also included in this embodiment are compounds in which $R_3$ is phenyl.

One embodiment provides a compound of Formula (I) or a salt thereof, having a structure of Formula (II) to (IV) wherein: $R_1$ is —OCH$_3$, —OCHF$_2$, or —CH$_2$OCH$_3$; $R_2$ is H, F, Cl, Br, —OH, —CN, $C_{1-3}$ fluoroalkyl, $C_{1-3}$ hydroxyalkyl, $C_{2-4}$ alkenyl, $C_{2-4}$ alkynyl, or —C(O)O(C$_{1-6}$ alkyl); $R_3$ is phenyl or naphthalenyl substituted with zero to 2 $R_{3a}$; and $R_{3a}$, at each occurrence, is independently F, Cl, Br, $C_{1-3}$ alkyl, $C_{1-3}$ fluoroalkyl, $C_{1-3}$ alkoxy, or $C_{1-3}$ fluoroalkoxy. Included in this embodiment are compounds in which $R_1$ is —OCHF$_2$; $R_2$ is Cl, Br, —CN, —CF$_3$, —CH=CH$_2$, —C≡CH, or —C(O)OCH$_3$; $R_3$ is phenyl or naphthalenyl substituted with 1 or 2 $R_{3a}$; and $R_{3a}$, at each occurrence, is independently F, Cl, Br, —CH$_3$, —CF$_3$, —OCH$_3$, or —OCF$_3$. Also included in this embodiment are compounds in which $R_3$ is phenyl.

One embodiment provides a compound of Formula (I) or a salt thereof, wherein $R_3$ is phenyl substituted with 1 to 2 $R_{3a}$; and $R_1$, $R_2$, and $R_{3a}$ are defined in the first aspect. Included in this embodiment are compounds in which $R_{3a}$, at each occurrence, is independently F, Cl, Br, $C_{1-3}$ alkyl, $C_{1-3}$ fluoroalkyl, $C_{1-3}$ alkoxy, or $C_{1-3}$ fluoroalkoxy. Also included are compounds in which $R_{3a}$, at each occurrence, is independently F, Cl, Br, —CH$_3$, —CF$_3$. —OCH$_3$, or —OCF$_3$.

One embodiment provides a compound of Formula (I) or a salt thereof, wherein $R_3$ is naphthalenyl substituted with 1 to 2 $R_{3a}$; and $R_1$. $R_2$, and $R_{3a}$ are defined in the first aspect. Included in this embodiment are compounds in which $R_{3a}$, at each occurrence, is independently F, Cl, Br, $C_{1-3}$ alkyl, $C_{1-3}$ fluoroalkyl, $C_{1-3}$ alkoxy, or $C_{1-3}$ fluoroalkoxy. Also included are compounds in which $R_{3a}$, at each occurrence, is independently F, Cl, Br, —CH$_3$, —CF$_3$, —OCH$_3$, or —OCF$_3$.

One embodiment provides a compound of Formula (I) or a salt thereof, wherein $R_{3a}$, at each occurrence, is independently:

(i) H, F, Cl, Br, —CN, —OH, $C_{1-3}$ alkyl, $C_{1-3}$ fluoroalkyl, $C_{1-6}$ hydroxyalkyl, $C_{1-6}$ alkoxy, $C_{1-3}$ fluoroalkoxy, $C_{3-6}$ cycloalkyl, $C_{3-6}$ fluorocycloalkyl, 3- to 6-membered heterocyclyl, —CH(OH)(C$_{3-6}$ cycloalkyl), —CH(OH)(aryl), —CH(OH)heteroaryl), ($C_{1-3}$ alkoxy)-($C_{1-3}$ alkylene), —(CH$_2$)$_{1-3}$NR$_a$R$_a$, —(CH$_2$)$_{1-3}$NHS(O)$_2$(aryl), —O(CH$_2$)$_{1-3}$(aryl), —O(CH$_2$)$_{1-3}$(thiazolyl), —O(C$_{1-6}$ hydroxyalkyl), ($C_{1-3}$ alkoxy)-($C_{1-6}$ alkoxy), —O(CH$_2$)$_{1-4}$O(aryl), —O(CH$_2$)$_{1-4}$O(CH$_2$)$_{1-3}$(aryl), —O(CH$_2$)$_{1-4}$NR$_a$R$_a$, —O(CH$_2$)$_{1-4}$NHS(O)$_2$(C$_{1-3}$ alkyl), —O(CH$_2$)$_{1-4}$NHS(O)$_2$(aryl), —O(CH$_2$)$_{1-4}$C(O)OH, —O(CH$_2$)$_{1-4}$C(O)O(C$_{1-6}$ alkyl), —O(CH$_2$)$_{1-4}$C(O)NR$_a$(CH$_2$)$_{0-3}$(aryl), —O(CH$_2$)$_{1-4}$C(O)(morpholinyl), —O(CH$_2$)$_{1-4}$OC(O)O(C$_{1-3}$ alkyl), —O(CH$_2$)$_{1-3}$CHR$_a$OC(O)NR$_a$(CH$_2$)$_{1-4}$C(O)NR$_a$R$_a$, —O(CH$_2$)$_{1-4}$OC(O)NR$_a$(heteroaryl), —O(imidazolyl substituted with aryl), —C(O)OH. —C(O)O(C$_{1-6}$ alkyl), —NR$_a$C(O)(furanyl), —NR$_a$C(O)(pyranyl), —NR$_c$(O)O(C$_{1-6}$ alkyl), —NR$_a$C(O)O(CH$_2$)$_{1-4}$(aryl), —O(CH$_2$)$_{1-4}$NR$_a$C(O)O(C$_{1-6}$ alkyl), —O(CH$_2$)$_{1-4}$NR$_a$C(O)O(CH$_2$)$_{1-4}$(pyranyl), —O(CH$_2$)$_{1-4}$NR$_a$C(O)O(CH$_2$)$_{1-4}$(aryl), or —O(CH$_2$)$_{1-4}$NR$_a$C(O)O(CH$_2$)$_{1-4}$(furanyl), wherein each of said aryl or heteroaryl is substituted with zero to 5 substituents independently selected from F, Cl, —CN, $C_{1-3}$ alkyl, $C_{1-3}$ fluoroalkyl, $C_{1-4}$ hydroxyalkyl, $C_{1-3}$ alkoxy, —OCF$_3$, —OCHF$_2$, —NH$_2$, —NH(C$_{1-6}$ alkyl), —N(C$_{1-4}$ alkyl)$_2$, $C_{1-3}$ hydroxyalkoxy, —CONR$_c$R$_c$, and —S(O)$_2$NR$_c$R$_c$;

(ii) —O(CH$_2$)$_{1-4}$NR$_a$S(O)$_2$R$_w$, wherein R$_w$ is aryl or heteroaryl substituted with zero to 2 substituents independently selected from F, Cl, —CN, $C_{1-3}$ alkyl, $C_{1-3}$ alkoxy, —OCF$_3$, —OCHF$_2$, and $C_{1-3}$ fluoroalkyl; or (iii) —O(CH$_2$)$_{1-4}$OC(O)NR$_a$R$_x$, —OCH(R$_d$)(CH$_2$)$_{1-3}$OC(O)NR$_a$R$_x$,
—O(CH$_2$)$_{1-3}$CH(R$_d$)OC(O)NR$_a$R$_x$, or —OCH(R$_d$)CH(R$_d$)(CH$_2$)$_{0-2}$OC(O)NR$_a$R$_x$, wherein R$_x$ is selected from H, $C_{1-4}$ alkyl, $C_{1-4}$ fluoroalkyl, phenyl, pyrrolyl, pyrazolyl, thiazolyl, pyridazinyl, pyrimidinyl, oxadiazolyl, thiadiazolyl, indolyl, pyrrolo[2,3-b]pyridinyl, benzo[d]oxazol-2(3H)-onyl, and —CH$_2$(heteroaryl), each phenyl, pyrrolyl, pyrazolyl, thiazolyl, pyridazinyl, pyrimidinyl, oxadiazolyl, thiadiazolyl, indolyl, pyrrolo[2,3-b]pyridinyl, benzo[d]oxazol-2(3H)-onyl, and heteroaryl substituted with zero to 2 substituents independently selected from F, —Cl, —CN, $C_{1-3}$ alkyl, $C_{1-3}$ fluoroalkyl, $C_{1-6}$ hydroxyalkyl, $C_{1-6}$ hydroxyalkoxy, $C_{1-3}$ alkoxy, —C(O)O(C$_{1-3}$ alkyl), —C(O)NH$_2$, —C(O)NH(C$_{1-6}$ alkyl), —C(O)N(C$_{1-6}$ alkyl)$_2$, —C(O)NR$_a$(C$_{1-6}$ hydroxyalkyl), —C(O)NR$_a$R$_a$, —C(O)NR$_b$R$_b$, —S(O)$_2$NR$_a$R$_a$, and methyl triazolyl.

One embodiment provides a compound of Formula (II) or a salt thereof, wherein: $R_1$ is —OCH$_3$, —OCHF$_2$, or —CH$_2$OCH$_3$; $R_2$ is H, F, Cl, Br, —OH, —CN, $C_{1-3}$ alkyl, $C_{1-3}$ fluoroalkyl, $C_{1-3}$ hydroxyalkyl, $C_{2-4}$ alkenyl, $C_{2-4}$ alkynyl, or —C(O)O(C$_{1-6}$ alkyl); $R_3$ is phenyl or naphthalenyl substituted with zero to 2 $R_{3a}$; and $R_{3a}$, at each occurrence, is independently F, Cl, Br, $C_{1-3}$ alkyl, $C_{1-3}$ fluoroalkyl, $C_{1-3}$ alkoxy, or $C_{1-3}$ fluoroalkoxy, with the proviso that the compound is not:

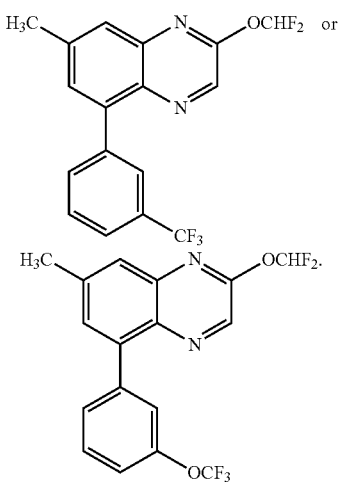

Included in this embodiment are compounds in which $R_1$ is —OCHF$_2$; $R_2$ is Cl, Br, —CN, —CH$_3$, —CF$_3$, —CH═CH$_2$, —C≡CH, or —C(O)OCH$_3$; $R_3$ is phenyl or naphthalenyl substituted with 1 or 2 $R_{3a}$; and $R_{3a}$, at each occurrence, is independently F, Cl, Br, —CH, —CF$_3$, —OCH$_3$, or —OCF$_3$. Also included in this embodiment are compounds in which $R_3$ is phenyl.

One embodiment provides a pharmaceutical composition comprising a pharmaceutically acceptable carrier and a compound of Formula (I) selected from:

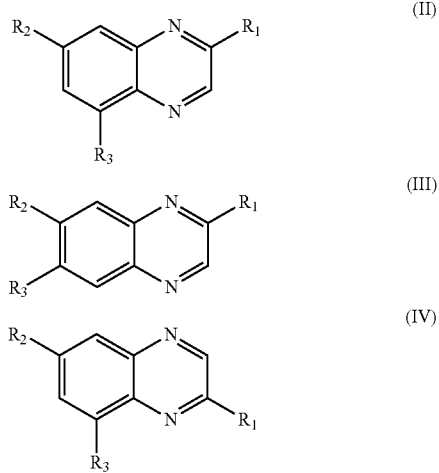

or a pharmaceutically acceptable salt thereof, wherein: $R_1$ is —OCH$_3$, —OCHF$_2$, or —CH$_2$OCH$_3$; $R_2$ is H, F, Cl, Br, —OH, —CN, $C_{1-3}$ alkyl, $C_{1-3}$ fluoroalkyl, $C_{1-3}$ hydroxyalkyl, $C_{2-4}$ alkenyl, $C_{2-4}$ alkynyl, or —C(O)O($C_{1-6}$ alkyl); $R_3$ is phenyl or naphthalenyl substituted with zero to 2 $R_{3a}$; and $R_{3a}$, at each occurrence, is independently F, Cl, Br, $C_{1-3}$ alkyl, $C_{1-3}$ fluoroalkyl, $C_{1-3}$ alkoxy, or $C_{1-3}$ fluoroalkoxy. Included in this embodiment are compounds in which $R_1$ is —OCHF$_2$; $R_2$ is Cl, Br, —CN, —CH$_3$, —CF$_3$, —CH═CH$_2$, —C≡CH, or —C(O)OCH$_3$; $R_3$ is phenyl or naphthalenyl substituted with 1 or 2 $R_{3a}$; and $R_{3a}$, at each occurrence, is independently F, Cl, Br, —CH$_3$, —CF$_3$, —OCH$_3$, or —OCF$_3$. Also included in this embodiment are compounds in which $R_3$ is phenyl.

One embodiment provides a pharmaceutical composition comprising a pharmaceutically acceptable carrier and a compound of Formula (II) or a pharmaceutically acceptable salt thereof, wherein: $R_1$ is —OCH$_3$, —OCHF$_2$, or —CH$_2$OCH$_3$; $R_2$ is H, F, Cl, Br, —OH, —CN, $C_{1-3}$ alkyl, $C_{1-3}$ fluoroalkyl, $C_{1-3}$ hydroxyalkyl, $C_{2-4}$ alkenyl, $C_{2-4}$ alkynyl, or —C(O)O($C_{1-6}$ alkyl); $R_3$ is phenyl or naphthalenyl substituted with zero to 2 $R_{3a}$; and $R_{3a}$, at each occurrence, is independently F, Cl, Br, $C_{1-3}$ alkyl, $C_{1-3}$ fluoroalkyl, $C_{1-3}$ alkoxy, or $C_{1-3}$ fluoroalkoxy. Included in this embodiment are compounds in which $R_1$ is —OCHF$_2$; $R_2$ is Cl, Br, —CN, —CH$_3$, —CF$_3$, —CH═CH$_2$, —C≡CH, or —C(O)OCH$_3$; $R_3$ is phenyl or naphthalenyl substituted with 1 or 2 $R_{3a}$; and $R_{3a}$, at each occurrence, is independently F, Cl, Br, —CH, —CF$_3$, —OCH$_3$, or —OCF$_3$. Also included in this embodiment are compounds in which $R_3$ is phenyl.

One embodiment provides a compound of Formula (I) selected from 3-(difluoromethoxy)-8-(4-methoxyphenyl)quinoxaline-6-carbonitrile (1); 7-chloro-2-(difluoromethoxy)-5-(4-methoxyphenyl)quinoxaline (2); 2-(difluoromethoxy)-5-(4-methoxyphenyl)-7-vinylquinoxaline (3); methyl 3-(difluoromethoxy)-8-(4-methoxyphenyl)quinoxaline-6-carboxylate (4); 2-(difluoromethoxy)-7-ethynyl-5-(4-methoxyphenyl)quinoxaline (5); 2-(difluoromethoxy)-5-(4-methoxyphenyl)-7-methylquinoxaline (6); 2-(difluoromethoxy)-6-(4-methoxyphenyl)-7-(trifluoromethyl) quinoxaline (7); 2-(difluoromethoxy)-5-(4-methoxyphenyl)-7-(trifluoromethyl) quinoxaline (8); 2-(difluoromethoxy)-5-(4-methoxy-3-(trifluoromethyl)phenyl)-7-(trifluoromethyl)quinoxaline (9); 2-(difluoromethoxy)-5-(3-methoxyphenyl)-7-(trifluoromethyl)quinoxaline (10); 2-(difluoromethoxy)-5-(6-methoxynaphthalen-2-yl)-7-(trifluoromethyl)quinoxaline (11); 2-(difluoromethoxy)-5-(3-fluoro-4-methoxyphenyl)-7-(trifluoromethyl)quinoxaline (12); 2-(difluoromethoxy)-5-(3-methoxy-5-(trifluoromethyl) phenyl)-7-(trifluoromethyl) quinoxaline (13); 2-(difluoromethoxy)-8-(4-methoxyphenyl)-6-(rifluoromethyl) quinoxaline (14); 5-(3-bromo-4-methoxyphenyl)-2-(difluoromethoxy)-7-(trifluoromethyl)quinoxaline (15); 2-(difluoromethoxy)-5-(4-methoxy-3-(trifluoromethyl)phenyl)-7-methylquinoxaline (16); 2-(difluoromethoxy)-5-(4-fluoro-3-(trifluoromethyl)phenyl)-7-methylquinoxaline (17); 5-(3-chlorophenyl)-2-(difluoromethoxy)-7-methylquinoxaline (18); 2-(difluoromethoxy)-5-(3-fluoro-5-methoxyphenyl)-7-methylquinoxaline (21); 2-(difluoromethoxy)-5-(3,4-difluorophenyl)-7-methylquinoxaline (22), 5-(2,4-dichlorophenyl)-2-(difluoromethoxy)-7-methylquinoxaline (23); 5-(3,4-dichlorophenyl)-2-(difluoromethoxy)-7-methylquinoxaline (24); 2-(difluoromethoxy)-7-methyl-5-(3-(trifluoromethyl)phenyl) quinoxaline (25); 2-(difluoromethoxy)-7-methyl-5-(3-(trifluoromethoxy)phenyl) quinoxaline (26); and 7-bromo-2-(difluoromethoxy)-5-(4-methoxyphenyl)quinoxaline (27).

One embodiment provides a pharmaceutical composition comprising a pharmaceutically acceptable carrier and a compound of Formula (I) selected from: 3-(difluoromethoxy)-8-(4-methoxyphenyl)quinoxaline-6-carbonitrile (1); 7-chloro-2-(difluoromethoxy)-5-(4-methoxyphenyl)quinoxaline (2); 2-(difluoromethoxy)-5-(4-methoxyphenyl)-7-vinylquinoxaline (3); methyl 3-(difluoromethoxy)-8-(4-methoxyphenyl)quinoxaline-6-carboxylate (4); 2-(difluoromethoxy)-7-ethynyl-5-(4-methoxyphenyl)quinoxaline (5); 2-(difluoromethoxy)-5-(4-methoxyphenyl)-7-methylquinoxaline (6); 2-(difluoromethoxy)-6-(4-methoxyphenyl)-7-(trifluoromethyl) quinoxaline (7); 2-(difluoromethoxy)-5-(4-methoxyphenyl)-7-(trifluoromethyl) quinoxaline (8); 2-(difluoromethoxy)-5-(4-methoxy-3-(trifluoromethyl) phenyl)-7-(trifluoromethyl) quinoxaline (9); 2-(difluoromethoxy)-5-(3-methoxyphenyl)-7-(trifluoromethyl)quinoxaline (10); 2-(difluoromethoxy)-5-(6-methoxynaphthalen-2-yl)-7-(trifluoromethyl)quinoxaline (11); 2-(difluoromethoxy)-5-(3-fluoro-4-methoxyphenyl)-7-(trifluoromethyl)quinoxaline (12); 2-(difluoromethoxy)-5-(3-methoxy-5-(trifluoromethyl) phenyl)-7-(trifluoromethyl) quinoxaline (13); 2-(difluoromethoxy)-8-(4-methoxyphenyl)-6-(trifluoromethyl) quinoxaline (14); 5-(3-bromo-4-methoxyphenyl)-2-(difluoromethoxy)-7-(trifluoromethyl)quinoxaline (15); 2-(difluoromethoxy)-5-(4-methoxy-3-(trifluoromethyl)phenyl)-7-methylquinoxaline (16); 2-(difluoromethoxy)-5-(4-fluoro-3-(trifluoromethyl)phenyl)-7-methylquinoxaline (17); 5-(3-chlorophenyl)-2-(difluoromethoxy)-7-methylquinoxaline (18); 2-(difluoromethoxy)-7-methyl-5-(4-(trifluoromethyl)phenyl)quinoxaline (19); 2-(difluoromethoxy)-7-methyl-5-(4-(trifluoromethoxy)phenyl)quinoxaline (20); 2-(difluoromethoxy)-5-(3-fluoro-5-methoxyphenyl)-7-methylquinoxaline (21); 2-(difluoromethoxy)-5-(3,4-difluorophenyl)-7-methylquinoxaline (22); 5-(2,4-dichlorophenyl)-2-(difluoromethoxy)-7-methylquinoxaline (23); 5-(3,4-dichlorophenyl)-2-(difluoromethoxy)-7-methylquinoxaline (24); 2-(difluoromethoxy)-7-methyl-5-(3-(trifluoromethyl) phenyl) quinoxaline (25); 2-(difluoromethoxy)-7-methyl-5-3-(trifluoromethoxy)phenyl) quinoxaline (26); and 7-bromo-2-(difluoromethoxy)-5-(4-methoxyphenyl)quinoxaline (27).

The present invention may be embodied in other specific forms without departing from the spirit or essential attributes thereof. This invention encompasses all combinations of the aspects and/or embodiments of the invention noted herein. It is understood that any and all embodiments of the present invention may be taken in conjunction with any other embodiment or embodiments to describe additional embodiments. It is also to be understood that each individual element of the embodiments is meant to be combined with any and all other elements from any embodiment to describe an additional embodiment.

DEFINITIONS

The features and advantages of the invention may be more readily understood by those of ordinary skill in the art upon reading the following detailed description. It is to be appreciated that certain features of the invention that are, for clarity reasons, described above and below in the context of separate embodiments, may also be combined to form a single embodiment. Conversely, various features of the invention that are, for brevity reasons, described in the context of a single embodiment, may also be combined so as to form sub-combinations thereof. Embodiments identified herein as exemplary or preferred are intended to be illustrative and not limiting.

Unless specifically stated otherwise herein, references made in the singular may also include the plural. For example, "a" and "an" may refer to either one, or one or more.

As used herein, the phase "compounds" refers to at least one compound. For example, a compound of Formula (I) includes a compound of Formula (I) and two or more compounds of Formula (I).

Unless otherwise indicated, any heteroatom with unsatisfied valences is assumed to have hydrogen atoms sufficient to satisfy the valences.

The definitions set forth herein take precedence over definitions set forth in any patent, patent application, and/or patent application publication incorporated herein by reference.

Listed below are definitions of various terms used to describe the present invention. These definitions apply to the terms as they are used throughout the specification (unless they are otherwise limited in specific instances) either individually or as part of a larger group.

Throughout the specification, groups and substituents thereof may be chosen by one skilled in the field to provide stable moieties and compounds.

The terms "halo" and "halogen," as used herein, refer to F, Cl, Br, and I.

The term "cyano" refers to the group —CN.

The term "amino" refers to the group —NH$_2$.

The term "alkyl" as used herein, refers to both branched and straight-chain saturated aliphatic hydrocarbon groups containing, for example, from 1 to 12 carbon atoms, from 1 to 6 carbon atoms, and from 1 to 4 carbon atoms. Examples of alkyl groups include, but are not limited to, methyl (Me), ethyl (Et), propyl (e.g., n-propyl and i-propyl), butyl (e.g., n-butyl, i-butyl, sec-butyl, and t-butyl), and pentyl (e.g., n-pentyl, isopentyl, neopentyl), n-hexyl, 2-methylpentyl, 2-ethylbutyl, 3-methylpentyl, and 4-methylpentyl. When numbers appear in a subscript after the symbol "C", the subscript defines with more specificity the number of carbon atoms that a particular group may contain. For example, "$C_{1-4}$ alkyl" denotes straight and branched chain alkyl groups with one to four carbon atoms.

The term "fluoroalkyl" as used herein is intended to include both branched and straight-chain saturated aliphatic hydrocarbon groups substituted with one or more fluorine atoms. For example, "$C_{1-4}$ fluoroalkyl" is intended to include $C_1$, $C_2$, $C_3$, and $C_4$ alkyl groups substituted with one or more fluorine atoms. Representative examples of fluoroalkyl groups include, but are not limited to, —CF$_3$ and —CH$_2$CF$_3$.

The term "aminoalkyl" as used herein is intended to include both branched and straight-chain saturated aliphatic hydrocarbon groups substituted with one or more amino groups. For example, "$C_{1-4}$ aminoalkyl" is intended to include $C_1$, $C_2$, $C_3$, and $C_4$ alkyl groups substituted with one or more amino groups. Representative examples of aminoalkyl groups include, but are not limited to, —CH$_2$NH$_2$, —CH$_2$CH$_2$NH$_2$, and —CH$_2$CH(NH$_2$)CH$_3$.

The term "hydroxyalkyl" includes both branched and straight-chain saturated alkyl groups substituted with one or more hydroxyl groups. For example, "hydroxyalkyl" includes —CH$_2$OH, —CH$_2$CH$_2$OH, and $C_{1-4}$ hydroxyalkyl.

The term "hydroxy-deuteroalkyl" includes both branched and straight-chain saturated alkyl groups substituted with one or more hydroxyl groups and one or more deuterium atoms. Representative examples of hydroxy-deuteroalkyl groups include, but are not limited to, —CD$_2$OH and —CH(CD$_3$)$_2$OH.

The term "hydroxy-fluoroalkyl" includes both branched and straight-chain saturated alkyl groups substituted with one or more hydroxyl groups and one or more fluorine atoms. Representative examples of hydroxy-fluoroalkyl groups include, but are not limited to, —CF$_2$OH and —CF$_2$CH$_2$OH.

As used herein. "alkylene" refers to a bivalent alkyl radical having the general formula —(CH$_2$)$_n$—, where n is 1 to 10. Non-limiting examples include methylene, dimethylene, trimethylene, tetramethylene, pentamethylene, and hexamethylene. For example, "$C_{1-6}$ alkylene" denotes straight and branched chain alkylene groups with one to six carbon atoms. Further, for example, "$C_{0-4}$ alkylene" denotes a bond and straight and branched chain alkylene groups with one to four carbon atoms.

As used herein, "deuteroalkylene" refers to an alkylene group in which one or more hydrogen atoms have been replaced with deuterium atoms. For example, ("$C_{1-6}$ deuteroalkylene" denotes straight and branched chain deuteroalkylene groups with one to six carbon atoms.

As used herein, "fluoroalkylene" refers to an alkylene group substituted with one or more fluorine atoms. For example, "$C_{1-6}$ fluoroalkylene" denotes straight and branched chain fluoroalkylene groups with one to six carbon atoms.

The term "alkenyl" refers to a straight or branched chain hydrocarbon radical containing from 2 to 12 carbon atoms and at least one carbon-carbon double bond. Exemplary such groups include ethenyl or allyl. For example, "$C_{2-6}$ alkenyl" denotes straight and branched chain alkenyl groups with two to six carbon atoms.

The term "alkynyl" refers to a straight or branched chain hydrocarbon radical containing from 2 to 12 carbon atoms and at least one carbon to carbon triple bond. Exemplary such groups include ethynyl. For example, "$C_{2-6}$ alkynyl" denotes straight and branched chain alkynyl groups with two to six carbon atoms.

The term "cycloalkyl," as used herein, refers to a group derived from a non-aromatic monocyclic or polycyclic hydrocarbon molecule by removal of one hydrogen atom from a saturated ring carbon atom. Representative examples of cycloalkyl groups include, but are not limited to, cyclopropyl, cyclopentyl, and cyclohexyl. When numbers appear in a subscript after the symbol "C", the subscript defines with more specificity the number of carbon atoms that a particular cycloalkyl group may contain. For example, "$C_{3-6}$ cycloalkyl" denotes cycloalkyl groups with three to six carbon atoms.

The term "fluorocycloalkyl" refers to a cycloalkyl group in which one or more hydrogen atoms are replaced by fluoro group(s).

The term "cycloalkylalkylene" refers to a cycloalkyl group attached through an alkylene group to the parent molecular moiety. For example, "($C_{3-6}$ cycloalkyl)-($C_{0-2}$ alkylene)" denotes a $C_{3-6}$ cycloalkyl group attached through a bond or a $C_{1-2}$ alkylene to the parent molecular moiety.

The term "alkoxy," as used herein, refers to an alkyl group attached to the parent molecular moiety through an oxygen atom, for example, methoxy group (—OCH$_3$). For example, "$C_{1-3}$ alkoxy" denotes alkoxy groups with one to three carbon atoms.

The terms "fluoroalkoxy" and "—O(fluoroalkyl)" represent a fluoroalkyl group as defined above attached through an oxygen linkage (—O—). For example, "$C_{1-4}$ fluoroalkoxy" is intended to include $C_1$, $C_2$, $C_3$, and $C_4$ fluoroalkoxy groups.

The term "hydroxyalkoxy" represent a hydroxyalkyl group as defined above attached through an oxygen linkage (—O—). For example, "$C_{1-4}$ hydroxyalkoxy" is intended to include $C_1$, $C_2$, $C_3$, and $C_4$ hydroxyalkoxy groups.

The term "cycloalkoxy," as used herein, refers to a cycloalkyl group attached to the parent molecular moiety through an oxygen atom, for example, cyclopropoxy group (—O(cyclopropyl)).

The term "alkoxyalkoxy" as used herein, refers to an alkoxy group attached through an alkoxy group to the parent molecular moiety. For example, "($C_{1-3}$ alkoxy)-($C_{1-6}$ alkoxy)" denotes a $C_{1-3}$ alkoxy group attached through a $C_{1-6}$ alkoxy group to the parent molecular moiety.

The term "alkoxyalkylene" as used herein, refers to an alkoxy group attached through an alkylene group to the parent molecular moiety. For example, "($C_{1-3}$ alkoxy)-($C_{1-3}$ alkylene)" denotes a $C_{1-3}$ alkoxy group attached through a $C_{1-3}$ alkylene to the parent molecular moiety.

The term "fluoroalkoxyalkylene" as used herein, refers to a fluoroalkoxy group attached through an alkylene group. For example, "($C_{1-2}$ fluoroalkoxy)-($C_{1-2}$ alkylene)" denotes a $C_{1-2}$ fluoroalkoxy group attached through a $C_{1-2}$ alkylene to the parent molecular moiety.

The term "alkoxy-fluoroalkylene" as used herein, refers to an alkoxy group attached through a fluoroalkylene group to the parent molecular moiety. For example, "($C_{1-3}$ alkoxy)-($C_{1-3}$ fluoroalkylene)" denotes a $C_{1-3}$ alkoxy group attached through a $C_{1-3}$ fluoroalkylene to the parent molecular moiety.

The term "deuteroalkoxy-deuteroalkylene" as used herein, refers to a deuteroalkoxy group attached through a deuteroalkylene group to the parent molecular moiety. For example, "($C_{1-3}$ deuteroalkoxy)-($C_{1-3}$ deuteroalkylene)" denotes a $C_{1-3}$ deuteroalkoxy group attached through a $C_{1-3}$ deuteroalkylene to the parent molecular moiety.

The term "alkylthio," as used herein, refers to an alkyl group attached to the parent molecular moiety through a sulfur atom, for example, methylthio group (—SCH$_3$). For example, "$C_{1-3}$ alkylthio" denotes alkylthio groups with one to three carbon atoms.

The term "aryl," as used herein, refers to a group of atoms derived from a molecule containing aromatic ring(s) by removing one hydrogen that is bonded to the aromatic ring(s). Representative examples of aryl groups include, but are not limited to, phenyl, naphthyl, indanyl, indenyl, and 1,2,3,4-tetrahydronaphth-5-yl.

The term "benzyl," as used herein, refers to a methyl group in which one of the hydrogen atoms is replaced by a phenyl group.

The term "aryloxy," as used herein, refers to an aryl group attached through an oxygen group.

The term "phenoxy," as used herein, refers to a phenyl group attached through an oxygen group (—O-phenyl).

The term "heteroatom" refers to oxygen (O), sulfur (S), and nitrogen (N).

The term "heterocyclo" or "heterocyclyl" may be used interchangeably and refer to non-aromatic 3- to 7-membered monocyclic groups and 6- to 11-membered bicyclic groups, in which at least one of the rings has at least one heteroatom (O, S or N), said heteroatom containing ring preferably having 1 to 3 heteroatoms independently selected from O, S, and/or N. Each ring of such a group containing a heteroatom can contain one or two oxygen or sulfur atoms and/or from one to four nitrogen atoms provided that the total number of heteroatoms in each ring is four or less, and further provided that the ring contains at least one carbon atom. The nitrogen and sulfur atoms may optionally be oxidized and the nitrogen atoms may optionally be quaternized. The fused rings completing the bicyclic group may contain only carbon atoms and may be saturated, partially saturated, or unsaturated. The heterocyclo group may be attached at any available nitrogen or carbon atom. The heterocyclo ring may be unsubstituted or may contain one or more substituents as valence allows.

Exemplary monocyclic heterocyclyl groups include oxetanyl, azetidinyl, pyrrolidinyl, imidazolinyl, oxazolidinyl, isoxazolinyl, thiazolidinyl, isothiazolidinyl, tetrahydrofuranyl, piperidinyl, piperazinyl, 2-oxopiperazinyl, 2-oxopiperidinyl, 2-oxopyrrolodinyl, 2-oxoazepinyl, azepinyl, 4-piperidonyl, tetrahydropyranyl, morpholinyl, thiamorpholinyl, thiamorpholinyl sulfoxide, thiamorpholinyl sulfone, 1,3-dioxolane, and tetrahydro-1,1-dioxothienyl. Exemplary bicyclic heterocyclo groups include quinuclidinyl.

The term "heteroaryl" refers to substituted and unsubstituted aromatic 5- or 6-membered monocyclic groups and 9- or 10-membered bicyclic groups which have at least one heteroatom (O, S or N) in at least one of the rings, said heteroatom-containing ring preferably having 1, 2, or 3 heteroatoms independently selected from O, S, and/or N. Each ring of the heteroaryl group containing a heteroatom can contain one or two oxygen or sulfur atoms and/or from one to four nitrogen atoms provided that the total number of heteroatoms in each ring is four or less and each ring has at least one carbon atom. The fused rings completing the bicyclic group may contain only carbon atoms and may be saturated, partially saturated, or unsaturated. The nitrogen and sulfur atoms may optionally be oxidized and the nitrogen atoms may optionally be quaternized. Heteroaryl groups which are bicyclic or tricyclic must include at least one fully aromatic ring but the other fused ring or rings may be aromatic or non-aromatic. The heteroaryl group may be attached at any available nitrogen or carbon atom of any ring. The heteroaryl ring system may be unsubstituted or may contain one or more substituents.

Exemplary monocyclic heteroaryl groups include pyrrolyl, pyrazolyl, pyrazolinyl, imidazolyl, oxazolyl, isoxazolyl, thiazolyl, thiadiazolyl, isothiazolyl, furanyl, thiophenyl, oxadiazolyl, pyridinyl, pyrazinyl, pyrimidinyl, pyridazinyl, and triazinyl.

Exemplary bicyclic heteroaryl groups include indolyl, benzothiazolyl, benzodioxolyl, benzoxazolyl, benzothienyl, quinolinyl, tetrahydroisoquinolinyl, isoquinolinyl, benzimidazolyl, benzopyranyl, indolizinyl, benzofuranyl, chromonyl, coumarinyl, benzopyranyl, cinnolinyl, quinoxalinyl, indazolyl, pyrrolopyridinyl, furopyridinyl, dihydroisoindolyl, and tetrahydroquinolinyl.

The term "heteroaryloxy," as used herein, refers to a heteroaryl group attached through an oxygen group to the parent molecular moiety.

The term "arylalkylene" refers to an aryl group attached through an alkylene group to the parent molecular moiety. For example, "aryl($C_{1-2}$ alkylene)" refers to an aryl group attached through a $C_{1-2}$ alkylene to the parent molecular moiety.

The term "heteroarylalkylene" refers to a heteroaryl group attached through an alkylene group to the parent molecular moiety. For example, "heteroaryl($C_{1-2}$ alkylene)" refers to a heteroaryl group attached through a $C_{1-2}$ alkylene to the parent molecular moiety.

The term "aryloxyalkylene" refers to an aryloxy group attached through an alkylene group to the parent molecular moiety. For example, "aryloxy-($C_{1-2}$ alkylene)" refers to an aryloxy group attached through a $C_{1-2}$ alkylene to the parent molecular moiety.

The term "heteroaryloxyalkylene" refers to a heteroaryloxy group attached through an alkylene group to the parent molecular moiety. For example, "heteroaryloxy-($C_{1-2}$ alkylene)" refers to a heteroaryloxy group attached through a $C_{1-2}$ alkylene to the parent molecular moiety.

The compounds of the present invention can be provided as amorphous solids or crystalline solids. Lyophilization can be employed to provide the compounds as amorphous solids.

It should further be understood that solvates (e.g., hydrates) of the Compounds of Formula (I) are also within the scope of the present invention. The term "solvate" means a physical association of a compound of Formula (I) with one or more solvent molecules, whether organic or inorganic. This physical association includes hydrogen bonding. In certain instances the solvate will be capable of isolation, for example when one or more solvent molecules are incorporated in the crystal lattice of the crystalline solid. "Solvate" encompasses both solution-phase and isolable solvates. Exemplary solvates include hydrates, ethanolates, methanolates, isopropanolates, acetonitrile solvates, and ethyl acetate solvates. Methods of solvation are known in the art.

In addition, compounds of Formula (I), subsequent to their preparation, can be isolated and purified to obtain a composition containing an amount by weight equal to or greater than 99% of a compound of Formula (I) ("substantially pure"), which is then used or formulated as described herein. Such "substantially pure" compounds of Formula (I) are also contemplated herein as part of the present invention.

"Stable compound" and "stable structure" are meant to indicate a compound that is sufficiently robust to survive isolation to a useful degree of purity from a reaction mixture, and formulation into an efficacious therapeutic agent. The present invention is intended to embody stable compounds.

The compounds of the present invention are intended to include all isotopes of atoms occurring in the present compounds. Isotopes include those atoms having the same atomic number but different mass numbers. By way of general example and without limitation, isotopes of hydrogen include deuterium (D) and tritium (T). Isotopes of carbon include $^{13}C$ and $^{14}C$. Isotopically-labeled compounds of the invention can generally be prepared by conventional techniques known to those skilled in the art or by processes analogous to those described herein, using an appropriate isotopically-labeled reagent in place of the non-labeled reagent otherwise employed. For example, methyl (—$CH_3$) also includes deuterated methyl groups such as —$CD_3$.

BIOLOGY

The term "PAR4 antagonist" denotes an inhibitor of platelet aggregation which binds PAR4 and inhibits PAR4 cleavage and/or signaling. Typically, PAR4 activity is reduced in a dose dependent manner by at least 10%, 20%, 30%, 40%, 50%, 60%, 70%, 80%, 90%, or 100% compared to such activity in a control cell. The control cell is a cell that has not been treated with the compound. PAR4 activity is determined by any standard method in the art, including those described herein (for example calcium mobilization in PAR4 expressing cells, platelet aggregation, platelet activation assays measuring e.g., calcium mobilization, p-selectin or CD40L release, or thrombosis and hemostasis models). The term "PAR4 antagonist" also includes a compound that inhibits both PAR1 and PAR4.

It is desirable to find compounds with advantageous and improved characteristics compared with known anti-platelet agents, in one or more of the following categories that are given as examples, and are not intended to be limiting: (a) pharmacokinetic properties, including oral bioavailability, half life, and clearance; (b) pharmaceutical properties; (c) dosage requirements; (d) factors that decrease blood concentration peak-to-trough characteristics; (e) factors that increase the concentration of active drug at the receptor; (f) factors that decrease the liability for clinical drug-drug interactions; (g) factors that decrease the potential for adverse side-effects, including selectivity versus other biological targets; (h) improved therapeutic index with less propensity for bleeding; and (h) factors that improve manufacturing costs or feasibility.

The term "compound", as used herein, means a chemical, be it naturally-occurring or artificially-derived. Compounds may include, for example, peptides, polypeptides, synthetic organic molecules, naturally occurring organic molecules, nucleic acid molecules, peptide nucleic acid molecules, and components and derivatives thereof.

As used herein, the term "patient" encompasses all mammalian species.

As used herein, the term "subject" refers to any human or nonhuman organism that could potentially benefit from treatment with a PAR4 antagonist. Exemplary subjects include human beings of any age with risk factors for cardiovascular disease, or patients that have already experienced one episode of cardiovascular disease. Common risk factors include, but are not limited to, age, male sex, hypertension, smoking or smoking history, elevation of triglycerides, elevation of total cholesterol or LDL cholesterol.

In some embodiments, the subject is a species having a dual PAR1/PAR4 platelet receptor repertoire. As used herein, the term "dual PAR1/PAR4 platelet receptor repertoire" means that a subject expresses PAR1 and PAR4 in platelets or their precursors. Exemplary subjects having a dual PAR1/PAR4 platelet receptor repertoire include human beings, non-human primates, and guinea pigs.

In other embodiments, the subject is a species having a dual PAR3/PAR4 platelet receptor repertoire. As used herein, the term "dual PAR3/PAR4 platelet receptor repertoire" means that a subject expresses PAR3 and PAR4 in platelets or their precursors. Exemplary subjects having a dual PAR3/PAR4 platelet receptor repertoire include rodents and rabbits.

As used herein, "treating" or "treatment" cover the treatment of a disease-state in a mammal, particularly in a human, and include: (a) inhibiting the disease-state, i.e., arresting its development; and/or (b) relieving the disease-state. i.e., causing regression of the disease state.

As used herein, "prophylaxis" or "prevention" cover the preventive treatment of a subclinical disease-state in a mammal, particularly in a human, aimed at reducing the probability of the occurrence of a clinical disease-state. Patients are selected for preventative therapy based on factors that are known to increase risk of suffering a clinical disease state compared to the general population. "Prophylaxis" therapies can be divided into (a) primary prevention and (b) secondary prevention. Primary prevention is defined as treatment in a subject that has not yet presented with a clinical disease state, whereas secondary prevention is defined as preventing a second occurrence of the same or similar clinical disease state.

As used herein, "risk reduction" covers therapies that lower the incidence of development of a clinical disease state. As such, primary and secondary prevention therapies are examples of risk reduction.

"Therapeutically effective amount" is intended to include an amount of a compound of the present invention that is effective when administered alone or in combination to inhibit and/or antagonize PAR4 and/or to prevent or treat the disorders listed herein. When applied to a combination, the term refers to combined amounts of the active ingredients that result in the preventive or therapeutic effect, whether administered in combination, serially, or simultaneously.

The term "thrombosis", as used herein, refers to formation or presence of a thrombus (pl. thrombi) within a blood vessel that may cause ischemia or infarction of tissues supplied by the vessel. The term "embolism", as used herein, refers to sudden blocking of an artery by a clot or foreign material that has been brought to its site of lodgment by the blood current. The term "thromboembolism", as used herein, refers to obstruction of a blood vessel with thrombotic material carried by the blood stream from the site of origin to plug another vessel. The term "thromboembolic disorders" entails both "thrombotic" and "embolic" disorders (defined above).

The term "thromboembolic disorders" as used herein includes arterial cardiovascular thromboembolic disorders, venous cardiovascular or cerebrovascular thromboembolic disorders, and thromboembolic disorders in the chambers of the heart or in the peripheral circulation. The term "thromboembolic disorders" as used herein also includes specific disorders selected from, but not limited to, unstable angina or other acute coronary syndromes, atrial fibrillation, first or recurrent myocardial infarction, ischemic sudden death, transient ischemic attack, stroke, atherosclerosis, peripheral occlusive arterial disease, venous thrombosis, deep vein thrombosis, thrombophlebitis, arterial embolism, coronary arterial thrombosis, cerebral arterial thrombosis, cerebral embolism, kidney embolism, pulmonary embolism, and thrombosis resulting from medical implants, devices, or procedures in which blood is exposed to an artificial surface that promotes thrombosis. The medical implants or devices include, but are not limited to: prosthetic valves, artificial valves, indwelling catheters, stents, blood oxygenators, shunts, vascular access ports, ventricular assist devices and artificial hearts or heart chambers, and vessel grafts. The procedures include, but are not limited to: cardiopulmonary bypass, percutaneous coronary intervention, and hemodialysis. In another embodiment, the term "thromboembolic disorders" includes acute coronary syndrome, stroke, deep vein thrombosis, and pulmonary embolism.

In another embodiment, the present invention provides a method for the treatment of a thromboembolic disorder, wherein the thromboembolic disorder is selected from unstable angina, an acute coronary syndrome, atrial fibrillation, myocardial infarction, transient ischemic attack, stroke, atherosclerosis, peripheral occlusive arterial disease, venous thrombosis, deep vein thrombosis, thrombophlebitis, arterial embolism, coronary arterial thrombosis, cerebral arterial thrombosis, cerebral embolism, kidney embolism, pulmonary embolism, and thrombosis resulting from medical implants, devices, or procedures in which blood is exposed to an artificial surface that promotes thrombosis. In another embodiment, the present invention provides a method for the treatment of a thromboembolic disorder, wherein the thromboembolic disorder is selected from acute coronary syndrome, stroke, venous thrombosis, atrial fibrillation, and thrombosis resulting from medical implants and devices.

In another embodiment, the present invention provides a method for the primary prophylaxis of a thromboembolic disorder, wherein the thromboembolic disorder is selected from unstable angina, an acute coronary syndrome, atrial fibrillation, myocardial infarction, ischemic sudden death, transient ischemic attack, stroke, atherosclerosis, peripheral occlusive arterial disease, venous thrombosis, deep vein thrombosis, thrombophlebitis, arterial embolism, coronary arterial thrombosis, cerebral arteial thrombosis, cerebral embolism, kidney embolism, pulmonary embolism, and thrombosis resulting from medical implants, devices, or procedures in which blood is exposed to an artificial surface that promotes thrombosis. In another embodiment, the present invention provides a method for the primary prophylaxis of a thromboembolic disorder, wherein the thromboembolic disorder is selected from acute coronary syndrome, stroke, venous thrombosis, and thrombosis resulting from medical implants and devices.

In another embodiment, the present invention provides a method for the secondary prophylaxis of a thromboembolic disorder, wherein the thromboembolic disorder is selected from unstable angina, an acute coronary syndrome, atrial fibrillation, recurrent myocardial infarction, transient ischemic attack, stroke, atherosclerosis, peripheral occlusive arterial disease, venous thrombosis, deep vein thrombosis, thrombophlebitis, arterial embolism, coronary arterial thrombosis, cerebral arterial thrombosis, cerebral embolism, kidney embolism, pulmonary embolism, and thrombosis resulting from medical implants, devices, or procedures in which blood is exposed to an artificial surface that promotes thrombosis. In another embodiment, the present invention provides a method for the secondary prophylaxis of a thromboembolic disorder, wherein the thromboembolic disorder is selected from acute coronary syndrome, stroke, atrial fibrillation and venous thrombosis.

The term "stroke", as used herein, refers to embolic stroke or atherothrombotic stroke arising from occlusive thrombosis in the carotid communis, carotid interna, or intracerebral arteries.

It is noted that thrombosis includes vessel occlusion (e.g., after a bypass) and reocclusion (e.g., during or after percutaneous transluminal coronary angioplasty). The thromboembolic disorders may result from conditions including but not limited to atherosclerosis, surgery or surgical complications, prolonged immobilization, arterial fibrillation, congenital thrombophilia, cancer, diabetes, effects of medications or hormones, and complications of pregnancy.

Thromboembolic disorders are frequently associated with patients with atherosclerosis. Risk factors for atherosclerosis include but are not limited to male gender, age, hypertension, lipid disorders, and diabetes mellitus. Risk factors for atherosclerosis are at the same time risk factors for complications of atherosclerosis, i.e., thromboembolic disorders.

Similarly, arterial fibrillation is frequently associated with thromboembolic disorders. Risk factors for arterial fibrillation and subsequent thromboembolic disorders include cardiovascular disease, rheumatic heart disease, nonrheumatic mitral valve disease, hypertensive cardiovascular disease, chronic lung disease, and a variety of miscellaneous cardiac abnormalities as well as thyrotoxicosis.

Diabetes mellitus is frequently associated with atherosclerosis and thromboembolic disorders. Risk factors for the more common type 2 include but are not limited to family history, obesity, physical inactivity, race/ethnicity, previously impaired fasting glucose or glucose tolerance test, history of gestational diabetes mellitus or delivery of a "big baby", hypertension, low HDL cholesterol, and polycystic ovary syndrome.

Thrombosis has been associated with a variety of tumor types, e.g., pancreatic cancer, breast cancer, brain tumors, lung cancer, ovarian cancer, prostate cancer, gastrointestinal malignancies, and Hodgkins or non-Hodgkins lymphoma. Recent studies suggest that the frequency of cancer in patients with thrombosis reflects the frequency of a particular cancer type in the general population. (Levitan, N. et al., *Medicine* (Baltimore), 78(5):285-291 (1999); Levine M. et al., *N. Engi. J. Med.*, 334(11):677-681 (1996); Blom, J. W. et al., *JAMA*, 293(6):715-722 (2005)). Hence, the most common cancers associated with thrombosis in men are prostate, colorectal, brain, and lung cancer, and in women are breast, ovary, and lung cancer. The observed rate of venous thromboembolism (VTE) in cancer patients is significant. The varying rates of VTE between different tumor types are most likely related to the selection of the patient population. Cancer patients at risk for thrombosis may possess any or all of the following risk factors: (i) the stage of the cancer (i.e., presence of metastases), (ii) the presence of central vein catheters, (iii) surgery and anticancer therapies including chemotherapy, and (iv) hormones and antiangiogenic drugs. Thus, it is common clinical practice to dose patients having advanced tumors with heparin or low molecular heparin to prevent thromboembolic disorders. A number of low molecular weight heparin preparations have been approved by the FDA for these indications.

The term "pharmaceutical composition," as used herein, means any composition, which contains at least one therapeutically or biologically active agent and is suitable for administration to the patient. Any of these formulations can be prepared by well-known and accepted methods of the art. See, for example, Gennaro. A. R., ed., *Remington: The Science and Practice of Pharmacy*, 20th Edition, Mack Publishing Co., Easton. Pa. (2000).

Pharmaceutically acceptable carriers include diluents, adjuvants and vehicles that may be used in the pharmaceutical compositions of this invention include, but are not limited to, ion exchangers, alumina, aluminum stearate, lecithin, self-emulsifying drug delivery systems (SEDDS) such as D-a-tocopherol polyethyleneglycol 1000 succinate, surfactants used in pharmaceutical dosage forms such as TWEEN surfactants (ICI Americas, Inc., Delaware) or other similar polymeric delivery matrices, serum proteins, such as human serum albumin, buffer substances such as phosphates, glycine, sorbic acid, potassium sorbate, partial glyceride mixtures of saturated vegetable fatty acids, water, salts or electrolytes, such as protamine sulfate, disodium hydrogen phosphate, potassium hydrogen phosphate, sodium chloride, zinc salts, colloidal silica, magnesium trisilicate, polyvinyl pyrrolidone, cellulose-based substances, polyethylene glycol, sodium carboxymethylcellulose, polyacrylates, waxes, polyethylene-polyoxvpropylene-block polymers, polyethylene glycol and wool fat. Cyclodextrins such as α-, β-, and γ-cyclodextrins, or chemically modified derivatives such as hydroxyalkylcyclodextrins, including 2- and 3-hydroxypropyl-cyclodextrins, or other solubilized derivatives may also be advantageously used to enhance delivery of compounds of the formulae described herein.

The invention includes administering to a subject a pharmaceutical composition that includes a compound that binds to PAR4 and inhibits PAR4 cleavage and/or signaling (referred to herein as a "PAR4 antagonist" or "therapeutic compound").

The pharmaceutical composition is administered using methods known in the art. Preferably, the compound is administered orally, rectally, nasally, by inhalation, topically or parenterally, e.g., subcutaneously, intraperitoneally, intramuscularly, and intravenously. The compound is optionally formulated as a component of a cocktail of therapeutic drugs to treat a thromboembolic disorder. In one embodiment, the pharmaceutical composition is administered orally.

The therapeutic compounds described herein are formulated into pharmaceutical compositions utilizing conventional methods. For example, a PAR4 antagonist is formulated in a capsule or a tablet for oral administration. Capsules may contain any standard pharmaceutically acceptable materials such as gelatin or cellulose. Tablets may be formulated in accordance with conventional procedures by compressing mixtures of a therapeutic compound with a solid carrier and a lubricant. Examples of solid carriers include starch and sugar bentonite. The compound is administered in the form of a hard shell tablet or a capsule containing a binder, e.g., lactose or mannitol, a conventional filler, and a tableting agent. Other formulations include an ointment, suppository, paste, spray, patch, cream, gel, resorbable sponge, or foam. Such formulations are produced using methods well known in the art. The compositions of the invention are also useful for parenteral administration, such as intravenous, subcutaneous, intramuscular, and intraperitoneal. Examples of formulations suitable for parenteral administration include aqueous solutions of the active agent in an isotonic saline solution, a 5% glucose solution, or another standard pharmaceutically acceptable excipient. Standard solubilizing agents such as PVP or cyclodextrins are also utilized as pharmaceutical excipients for delivery of the therapeutic compounds.

The preferred dose of the PAR4 antagonist is a biologically active dose. A biologically active dose is a dose that will inhibit cleavage and/or signaling of PAR4 and have an anti-thrombotic effect. Desirably, the PAR4 antagonist has the ability to reduce the activity of PAR4 by at least 5%, 10%, 20%, 30%, 40%, 50%, 60%, 70%, 80%, 90%, 100%, or more than 100% below untreated control levels. The levels of PAR4 in platelets is measured by any method known in the art, including, for example, receptor binding assay, platelet aggregation, platelet activation assays (e.g., p-selectin expression by FACS), Western blot or ELISA analysis using PAR4 cleavage sensitive antibodies. Alternatively, the biological activity of PAR4 is measured by assessing cellular signaling elicited by PAR4 (e.g., calcium mobilization or other second messenger assays).

In some embodiments, a therapeutically effective amount of a PAR4 compound is preferably from about less than 100 mg/kg, 50 mg/kg, 10 mg/kg, 5 mg/kg, 1 mg/kg, or less than 1 mg/kg. In a more preferred embodiment, the therapeutically effective amount of the PAR4 compound is less than 5 mg/kg. In a most preferred embodiment, the therapeutically effective amount of the PAR4 compound is less than 1 mg/kg. Effective doses vary, as recognized by those skilled in the art, depending on route of administration and excipient usage.

The activity of the PAR4 antagonists of the present invention can be measured in a variety of in vitro assays. Exemplary assays are shown below.

The FLIPR assay is an exemplary in vitro assay for measuring the activity of the PAR4 antagonists of the present invention. In this assay, intracellular calcium mobilization is induced in PAR4 expressing cells by a PAR4 agonist and calcium mobilization is monitored.

AYPGKF is a known PAR4 agonist. An alternative PAR4 agonist is H-Ala-Phe(4-F)-Pro-Gly-Trp-Leu-Val-Lys-Asn-Gly-NH$_2$. As shown in Example B below, H-Ala-Phe(4-F)-Pro-Gly-Trp-Leu-Val-Lys-Asn-Gly-NH$_2$ was validated as a PAR4 agonist in the FLIPR assay. A side-by-side comparison of the IC$_{50}$ values of ~180 compounds were performed using AYPGKF versus H-Ala-Phe(4-F)-Pro-Gly-Trp-Leu-Val-Lys-Asn-Gly-NH$_2$. The results demonstrated a strong correlation between the two assays. Additionally, H-Ala-Phe(4-F)-Pro-Gly-Trp-Leu-Val-Lys-Asn-Gly-NH$_2$ has improved agonist activity as compared to AYPGKF with an EC$_{50}$ that is 10 fold lower than the EC$_{50}$ for AYPGKF in the FLIPR assay. H-Ala-Phe(4-F)-Pro-Gly-Trp-Leu-Val-Lys-Asn-Gly-NH$_2$ can be synthesized using methods well known to those of skill in the art.

The FLIPR assay can also be used as a counterscreen to test agonist activity or PAR1 antagonist activity in a cell line that expresses both PAR1 and PAR4. The PAR1 antagonist activity can be tested by the ability of the compound to inhibit calcium mobilization induced by the PAR1 agonist peptide SFLLRN or other PAR1 agonist peptides.

The compounds of the current invention can be tested in vitro for their ability to inhibit platelet aggregation induced by gamma-thrombin as shown in Example C. Gamma-thrombin, a proteolytic product of alpha-thrombin which no longer interacts with PAR1, selectively cleaves and activates PAR4 (Soslau, G. et al., "Unique pathway of thrombin-induced platelet aggregation mediated by glycoprotein Ib", *J. Biol. Chem.*, 276:21173-21183 (2001)). Platelet aggregation can be monitored in a 96-well microplate aggregation assay format or using standard platelet aggregometer. The aggregation assay can also be employed to test the selectivity of the compound for inhibiting platelet aggregation induced by PAR4 agonist peptides, PAR1 agonist peptide, ADP, or thromboxane analogue U46619.

The activity of the PAR4 antagonists of the present invention can also be measured in a variety of in vivo assays. Exemplary mammals that can provide models of thrombosis and hemostasis to test the effectiveness of the PAR4 antagonists of the present invention as antithrombotic agents include, but are not limited to, guinea pigs and primates. Relevant efficacy models include, but are not limited to, electrically-induced carotid arterial thrombosis, FeCl$_3$-induced carotid artery thrombosis and arteriovenous-shunt thrombosis. Models of kidney bleeding time, renal bleeding time and other bleeding time measurements can be used to assess the bleeding risk of the antithrombotic agents described in the current invention.

In another embodiment, the present invention provides a method for the treatment of neoplasia or cancer caused by oncogenic, high-risk HPV. HPV-related cancers can be diagnosed by Pap smear testing or by using clinical HPV detection kits that measure the presence of the HPV DNA genome within cells. HPV-induced neoplasia include HPV-positive anogenital cancers affecting the cervix, vulva, vagina, penis, and anus. HPV is associated with nearly all cervical cancers, >70% of vaginal and anal cancers, 40% of vulvar cancers, and 49% of penile cancers) (Bruni L., Barrionuevo-Rosas L., Serran B., Brotons M., Cosano R., Munoz J., Bosch F. X., de Sanjose S., Castellsague X. ICO Information Centre on HPV and Cancer (HPV Information Centre). *Human Papillomavirus and Related Diseases in World*. Summary Report 2014-04-08. [Data Accessed 2014-05-27]). Anogenital neoplasia can be graded according to cytology, and include low-grade squamous intraepithelial lesions (LSIL), high grade squamous intraepithelial lesions (HSIL), carcinoma in situ (CIS) and invasive cancer, and are defined by cytological changes in size, shape, and number of abnormal cells. The present invention provides a method to treat HSIL, CIS, and invasive cancers related to HPV infection. Although most head and neck cancers are associated with high tobacco or alcohol use, an increasing percentage of head and neck cancers have also been associated with HPV. These head and neck cancers include tonsil cancer, base of tongue cancer, and other oropharyngeal cancers, and could also be treated using the method in this invention.

It is desirable to find compounds that will selectively kill or inhibit proliferation of cells transformed by HPV. The survival and proliferation of HPV-induced cancers are uniquely dependent on the action of two viral gene products, the HPV E6 and E7 proteins. Expression of these proteins from the integrated HPV genome correlates with HSIL and later stages of cancer progression, and protects the infected cell from apoptosis or senescence, processes that would normally prevent uncontrolled cellular proliferation. The identification of compounds that kill or inhibit proliferation of HPV-infected cells but do not adversely affect uninfected, non-cancerous cells, could provide a means to treat HPV-related cancers while minimizing the potential for unwanted side effects.

The HPV viruses referred to encompass all oncogenic or high-risk types of HPV, including HPV-16, -18, -26, -31, -33, -35, -39, -45, -51, -52, -53, -56, -58, -59, -66, -67, -68, -70, -73, and -82.

BIOLOGICAL ASSAYS

Materials
1) PAR1 and PAR4 Agonist Peptides

SFFLRR is a known high affinity PAR1 selective agonist peptide. (Reference: Seiler, S. M., "Thrombin receptor antagonists", *Seminars in Thrombosis and Hemosiasis*, 22(3):223-232 (1996).) The PAR4 agonist peptides AYPGKF and H-Ala-Phe(4-F)-Pro-Gly-Trp-Leu-Val-Lys-Asn-Gly-NH$_2$ were synthesized. H-Ala-Phe(4-F)-Pro-Gly-Trp-Leu-Val-Lys-Asn-Gly-NH$_2$ showed improved PAR4 agonist activity over AYPGKF in the FLIPR assay (EC$_{50}$ value of 8 µM for H-Ala-Phe(4-F)-Pro-Gly-Trp-Leu-Val-Lys-Asn-Gly-NH$_2$ and 60 µM for AYPGKF) and in washed platelet aggregation assay (EC$_{50}$ value of 0.9 LM for H-Ala-Phe(4-F)-Pro-Gly-Trp-Leu-Val-Lys-Asn-Gly-NH$_2$ and 12 µM for AYPGKF).

2) PAR4 Expressing Cells

HEK293 cells stably expressing PAR4 were generated by a standard method of transfection of human PAR4 (F2R23) cDNA expression vector and selected based on PAR4 protein expression or mRNA expression. Those cells demonstrated functional responses to PAR4 agonist peptide-induced intracellular calcium elevation using FLIPR® (Fluorometric Imaging Plate Reader: Molecular Devices Corp.). These cells also express endogenous PAR1 and can elicit calcium signal upon stimulation with PAR1 agonist peptide. Therefore, the same cells were also used to determine selectivity against PAR1 and agonist activity for both receptors. Cells from HEK293 PAR4 Clone 1.2A (BMS Arctic ID 383940) were propagated and used for calcium mobilization studies.

3) Preparation of Platelet Rich Plasma (PRP)

Human blood was collected in 3.8% sodium citrate at a ratio of 1 ml per 9 ml blood and centrifuged in a Sorvall® RT6000B centrifuge at 900 revolution per minute (rpm) at room temperature for 15 minutes. PRP was collected and used for aggregation assay. Refludan (Berlex Labs, Wayne, N.J.), a recombinant hirudin, at a final concentration of 1 unit/mL was added to the sample to selectively prevent PAR1 activation induced by residual alpha-thrombin contamination. The remaining blood sample was centrifuged at 2500 rpm at room temperature for 5 minutes to collect platelet-poor plasma (PPP).

4) Preparation of Washed Platelets (WP)

Human blood was collected in ACD (85 mM tri-sodium citrate, 78 mM citric acid, 110 mM D-glucose, pH 4.4) at a ratio of 1.4 ml per 10 ml blood. PRP was isolated by centrifugation at 170 g for 14 minutes and platelets were further pelleted by centrifugation at 1300 g for 6 minutes. Platelets were washed once with 10 ml ACD containing 1 mg/ml bovine serum albumin. Platelets were resuspended at ~2.5×10$^8$/ml in Tyrode's Buffer (137 mM NaCl, 2 mM KCl, 1.0 mM MgCl, 1 mM CaCl$_2$, 5 mM glucose, 20 mM HEPES pH 7.4).

FLIPR Assay in PAR4-Expressing HEK293 Cells

FLIPR-based calcium mobilization assay in HEK293 cells was used to measure PAR4 antagonism, agonism, and selectivity against PAR1. The activity of the PAR4 antagonists of the present invention were tested in PAR4 expressing cells by monitoring H-Ala-Phe(4-F)-Pro-Gly-Trp-Leu-Val-Lys-Asn-Gly-NH$_2$-induced intracellular calcium mobilization. Counter screens for agonist activity and PAR1 antagonist activity were also performed. Briefly, PAR1/PAR4-expressing HEK293 cells were grown in DMEM (Life Technology, Grand Island, N.Y.) containing 10% heat-inactivated FBS, 1% Penicillin-Streptomycin, 10 µg/mL blasticidin, and 100 µg/mL Zeocin at 37° C. with 5% CO$_2$. Cells were plated overnight prior to the experiment in a black 384-well Purecoat Amine clear bottom plate (Becton Dickinson Biosciences, San Jose, Calif.) at 10,000 cells/well in 30 µL growth medium and incubated in a humidified chamber at 37° C. with 5% CO$_2$ overnight. Prior to compound addition, the cell medium was replaced with 40 µL of IX calcium and magnesium-containing Hank's Balanced Saline Solution (HBSS) (with 20 mM HEPES) and 1:1000 diluted fluorescent calcium indicator (Codex Biosolutions, Gaithersburg, Md.). After a 30 minute incubation period at 37° C., and a further 30 minute incubation and equilibration period at room temperature, 20 µL test compound (diluted in 1×HBSS buffer) was added at various concentrations at 0.17% dimethyl sulfoxide (DMSO) final concentration. Changes in fluorescence intensity were measured using a Functional Drug Screening System (FDSS, Hamamatsu, Japan) to determine agonist activities. The cells were then incubated for 30 minutes at room temperature followed by addition of 20 µL of agonist peptide for antagonist activity measurement. The PAR4 agonist peptide (H-Ala-Phe(4-F)-Pro-Gly-Trp-Leu-Val-Lys-Asn-Gly-NH$_2$) and the PAR1 agonist peptide (SFFLRR) were routinely tested to ensure a proper response at the EC$_{50}$ value in the assay (~5 µM for PAR4 agonist peptide and ~2 µM for PAR1 agonist peptide). Compound potency was derived from 11-point concentration-response curves.

Gamma Thrombin Induced Platelet Aggregation Assays

The ability of the compounds of the current invention to inhibit platelet aggregation induced by gamma-thrombin was tested in a 96-well microplate aggregation assay format. Briefly, 90 µL of PRP or washed platelets were pre-incubated for 5 minutes at 37° C. with 3-fold serially diluted test compound, which was prepared as a 100-fold stock solution in dimethyl sulfoxide (DMSO). Aggregation was initiated by addition of 10 µL of gamma-thrombin (Haematologic Technologies, Inc. Essex Junction, Vt.) at 50-100 nM final concentration, which was titrated daily to achieve 80% platelet aggregation. The plate was then placed into a SpectraMax® Plus Plate Reader (Molecular Devices) at 37° C. Platelet aggregation was monitored at a wavelength of 405 nm using a kinetic analysis mode. Prior to the first data collection time point, the plate was shaken for 10 seconds to allow thorough mixing. Data was subsequently collected every 10 seconds for up to 7 minutes total. Data was collected using SoftMax® 5.4.1 software and exported to Microsoft Excel for analysis. The optical density (OD)

values at the time point that achieved 75% platelet activation by agonist alone were used for analysis. The OD value from a PRP sample without any treatment served as ODmaximum, and the OD value from a PPP sample containing no platelets served as the ODminimum. Inhibition of platelet aggregation (IPA) was calculated based on the formula: % IPA=(100−100*[ODcompound−ODminimum]/[ODmaximum−ODminimum]). The $IC_{50}$ value of the test compound was calculated by fitting the % IPA values to the one-site concentration response equation: Y=A+(B−A)/{1+(C/X)^D] }, using XLfit for 32 bit Excel® Version 2 Build 30 (ID Business Solutions Limited).

The aggregation assays were also employed to test the selectivity of the compound against other platelet receptors by using SFFLRR for PAR1, collagen (Chrono-Log, Havertown, Pa.) for collagen receptors, ADP for P2Y1 and P2Y12 and U46619 (Cayman Chemical, Ann Arbor, Mich.) for thromboxane receptors.

Alpha-Thrombin Induced Platelet Aggregation Assays

The ability of PAR4 antagonists to inhibit platelet aggregation induced by alpha-thrombin can be tested using human washed platelets. The antagonists are pre-incubated with washed platelets for 20 min. Aggregation is initiated by addition of 1.5 nM alpha-thrombin (Haematologic Technologies, Essex Junction, Vt.) to 300 μl of washed platelets at stirring speed of 1000 rpm. Platelet aggregation is monitored using an Optical Aggregometer (Chrono-Log. Havertown, Pa.) and the area under the curve (AUC) at 6 min was measured. $IC_{50}$ values are calculated using vehicle control as 0% inhibition.

Tissue Factor-Induced Platelet Aggregation Assay

The ability of PAR1 or PAR4 antagonists to inhibit platelet aggregation induced by endogenous thrombin can be tested in a tissue factor driven aggregation assay. Aggregation is initiated by addition of $CaCl_2$ and recombinant human tissue factor, which results in the generation of thrombin through activation of the coagulation pathway in the plasma. Anticoagulant agents such as corn trypsin inhibitor (Haematologic Technologies, Essex Junction, Vt.) at 50 μg/ml and PEFABLOC® FG (Centerchem, Norwalk, Conn.) are also added to the sample to prevent fibrin clot formation during the time of the study. Platelet aggregation is monitored using standard instrumentation including optical aggregometer or impedance aggregometer.

The following table sets out the results obtained employing various compounds of the invention tested in the PAR4 FLIPR assay.

TABLE A

| Ex | PAR4 FLIPR assay ($IC_{50}$, nM) |
|---|---|
| 1 | 1900 |
| 2 | 2100 |
| 3 | 690 |
| 4 | 1000 |
| 5 | 250 |
| 6 | 2400 |
| 8 | 1500 |
| 18 | 1400 |
| 19 | 800 |
| 20 | 1200 |
| 21 | 2200 |
| 22 | 1000 |

TABLE A-continued

| Ex | PAR4 FLIPR assay ($IC_{50}$, nM) |
|---|---|
| 23 | 12 |
| 24 | 3300 |
| 26 | 400 |
| 27 | 2600 |

The following table sets out the result obtained employing Example 6 tested in the PRP gamma thrombin assay.

TABLE B

| Ex. | PRP assay (Gamma Thrombin, $IC_{50}$, nM) |
|---|---|
| 6 | >30000 |

HPV Assays

Cell Culture

Caski (catalog number CRL-1550), SiHa (catalog number HTB-35), C33A (catalog number HTB-31), Saos-2 (ATCC HTB-85), and Hela (catalog number CCL-2) cells were obtained from the American Type Culture Collection (ATCC). The human cervical carcinoma cell lines Caski. SiHa, Hela and C33A, and the human osteosarcoma cell line Saos-2, and the human keratinocyte cell line HaCaT were cultured in Dulbecco's Modified Eagle Medium (DMEM, Invitrogen catalog number 11965-092) supplemented with 10% fetal bovine serum. The colorectal carcinoma cell line HCT-116 was cultured in Roswell Park Memorial Institute-1640 Medium (Invitrogen catalog number 11875-093) supplemented with 10% FBS. All cells were incubated at 37° C. in a humidified atmosphere with 5% $CO_2$ in air. To establish the SCHPV-18 cell line, one million primary neonatal human foreskin keratinocytes (Invitrogen, catalog no. C-001-5C), cultured in KBM Gold-keratinocvte cell basal medium (Lonza, catalog no. 192060), were electroporated with 5 μg HPV-18 plasmid DNA (ATCC catalog no. 45152D) using the Amaxa Nucleofector II on setting T-007. Cells were co-transfected with 2 μg plasmid pZSGreen1-N1 (Clontech catalog no. 632448) encoding G418 resistance, and cells were selected for four days in 100 μg/ml G418, after which selection was removed. Cells were maintained in culture six months prior to compound testing. Integration of the HPV 18 genome was confirmed by Southern blot. Control cells transfected in parallel with pZSGreen1-N1 alone became senescent four days after selection and the culture could not be expanded. SCHPV-18 cells were maintained in E medium (Fehrmann F, Laimins L A. Human papillomavirus type 31 life cycle: methods for study using tissue culture models. *Methods Mol Biol* 2005; 292:317-330).

Cell Viability Testing

For proliferation assays, cells were plated in white polystyrene 96-well plates (Costar catalog number 3917) for CellTiter Glo viability assays or 96-well special optics plates (Costar cat #3614) for CellTiter Blue viability assays. Cells were plated in the appropriate growth medium without antibiotics. Two hours after cell plating, a 200× compound stock diluted in DMSO was added to a final concentration of 0.5%. Plates were incubated at 37° C., for 4 days and then cell viability was assessed using either CellTiter Blue (Promega catalog number G8081) or CellTiter Glo (Promega catalog number G7572) according to the manufacturer's instructions. For the CellTiter Blue viability assay, data was collected using the SpectraMax Gemini EM (Molecular Devices) with an excitation wavelength of 530 nm and emission wavelength of 590 nm. For the CellTiter Glo viability assay, data was collected using the Envision Mulitlabel Reader (Perkin Elmer catalog number 2104-0010). To calculate $IC_{50}$ and $EC_{50}$ values, percent inhibition curves were fit using a four-parameter logistic formula [y=A+((B−A)/(+((C/x)^D)))], where A and B denote minimal and maximal % inhibition, respectively, C is the $IC_{50}$ value, D is the Hill slope, and x represents compound concentration.

The ability of compounds to selectively inhibit the proliferation of HPV-transformed cells can be tested using cell lines established in vitro. Table C, below, sets out the results obtained employing various compounds of the invention tested for their effects on proliferation of such cells. Caski or SiHa cells, transformed by HPV 16, Hela cells, transformed by HPV 18, or HPV-negative control cell lines (Saos-2 or C33a) were treated with various compounds. The $IC_{50}$ values indicate calculated concentrations at which a 50% reduction in cell proliferation was observed. Unlike the HPV-negative Saos-2 or C33a cell lines, the HPV-transformed cell lines rely on the presence of HPV for their continued proliferation. Therefore, a comparison of IC50 values from HPV-transformed cell lines with $IC_{50}$ values obtained from HPV-negative cell lines can be used to test for compound selectivity.

TABLE C

Selective Antiproliferative Activity For Cells Expressing Human Papillomavirus (HPV+) Types 18 and 16.

| Ex. No. | Caski (HPV16+) Proliferation $IC_{50}$ (µM) | HeLa (HPV18+) Proliferation $IC_{50}$ (µM) | SiHa (HPV16+) Proliferation $IC_{50}$ (µM) | Saos-2 (HPV−) Proliferation $IC_{50}$ (µM) | C33A (HPV−) Proliferation $IC_{50}$ (µM) |
|---|---|---|---|---|---|
| 1 | 2.3 | 1.5 | 1.7 | 7.7 | 6.9 |
| 2 | 10.0 | 9.3 | 8.0 | >100 | 54.0 |
| 3 | 61.9 | NA | NA | >100 | >100 |
| 4 | 12.6 | NA | NA | >100 | 53.4 |
| 5 | 3.4 | 3.3 | 4.5 | 53.1 | 42.3 |
| 6 | 7.1 | 10.6 | 10.1 | 48.0 | 44.8 |
| 7 | 5.0 | 4.4 | 4.3 | 92.1 | >100 |
| 8 | 2.5 | 2.3 | 4.3 | 58.3 | >99.5 |
| 9 | 3.3 | 1.5 | 1.7 | 76.2 | 78.7 |
| 10 | 3.9 | 4.4 | 5.1 | 55.0 | >99.5 |
| 11 | 2.9 | 2.1 | 2.7 | 45.9 | >99.5 |
| 12 | 3.2 | 1.1 | 1.3 | 14.3 | >99.5 |
| 13 | 15.6 | 37.0 | 24.0 | 40.3 | 40.5 |
| 14 | 2.8 | 2.6 | 2.9 | 57.7 | 49.9 |
| 15 | 16.5 | 18.2 | 12.9 | >99.5 | >99.5 |
| 16 | 7.0 | 9.1 | 9.4 | >99.5 | >99.5 |
| 17 | 17.9 | 23.7 | 17.8 | 96.5 | 58.3 |
| 18 | 13.9 | 13.2 | 11.6 | >100 | >100 |
| 19 | 14.6 | 29.9 | 20.5 | >100 | >100 |
| 20 | 16.4 | 45.1 | 22.1 | >100 | 83.5 |
| 21 | 13.3 | 14.7 | 11.7 | >100 | >100 |
| 22 | 15.9 | 16.9 | 12.6 | 70.6 | 94.4 |
| 23 | 12.9 | 10.9 | 9.3 | >100 | 79.7 |
| 24 | 12.8 | 12.7 | 8.9 | >100 | 89.4 |
| 25 | 14.5 | 15.2 | 11.7 | >100 | >100 |
| 26 | 6.0 | 4.6 | 3.8 | >100 | >100 |

Apoptosis Assay

Apoptosis is a cellular process in which a cascade of events, controlled by proteolytic cleavage events, results in chromatin condensation, blebbing of the cell membrane, fragmentation of cellular DNA, and cell death. Caspases 3 and 7 are enzymes which control initiation of the later stages of apoptosis. Caspase-3/-7 activity can therefore be used as a measure of induction of apoptosis in response to compound treatment. For caspase-3/7 activity assays, cells were plated in 96-well plates (Costar catalog no. 3917) in DMEM with 10% FBS two hours before compound treatment. Cells were treated with compounds in a final concentration of 0.5% DMSO, then the Caspase-Glo 3/7 Assay (Promega catalog no. G8090) was performed according to manufacturer's instructions. The assay measures luciferase activation upon release of aminoluciferin substrate from the DEVD amino acid sequence targeted by the caspases (McStay, G. Pl et al, *Cell Death Differ* 15:322-331 (2008)). Luminescence was measured using the EnVision Multilabel Reader (Perkin Elmer catalog no. 2104-0010) with aperture diameter 6 mm, height 4.2 mm, and measurement time of 0.1 second per well.

Example 15 was tested in an apoptosis assay using three HPV-transformed cell lines (Caski, SiHa, and SCHPV-18) and four HPV-negative cell lines (HCT-116, HaCat, C33a, and Saos-2). The cell lines were treated with a range of concentrations of the compound and induction of Caspase-3/-7 activity was measured relative to vehicle (DMSO)-treated controls. The results in FIG. 1 show that treatment with Example 15 selectively induced apoptosis in HPV-positive cell lines, as evidenced by a greater than 10-fold increase in Caspase-3/-7 activity.

Methods of Preparation

The compounds of the present invention can be prepared in a number of ways known to one skilled in the art of organic synthesis. The compounds of the present invention can be synthesized using the methods described below, together with synthetic methods known in the art of synthetic organic chemistry, or by variations thereon as appreciated by those skilled in the art. Preferred methods include, but are not limited to, those described below. The reactions are performed in a solvent or solvent mixture appropriate to the reagents and materials employed and suitable for the transformations being effected. It will be understood by those skilled in the art of organic synthesis that the functionality present on the molecule should be consistent with the transformations proposed. This will sometimes require a judgment to modify the order of the synthetic steps or to select one particular process scheme over another in order to obtain a desired compound of the invention.

It will also be recognized that another major consideration in the planning of any synthetic route in this field is the judicious choice of the protecting group used for protection of the reactive functional groups present in the compounds described in this invention. An authoritative account describing the many alternatives to the trained practitioner is Wuts et al. (*Greene's Protective Groups In Organic Synthesis*, 4th Edition. Wiley-Interscience (2006).

Compounds of Formula (I) can be obtained by palladium catalyzed cross coupling of aryl halides of Formula Ia with organometallic species $R_3$-M as shown in Scheme 1.

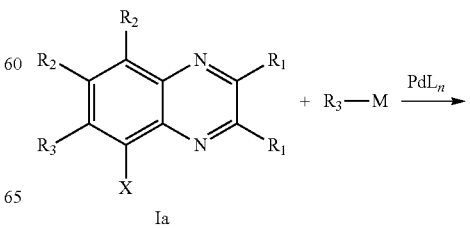

Scheme 1

-continued

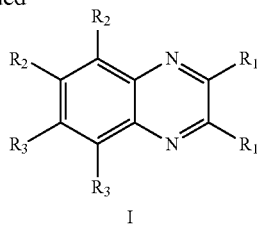

I

X = Cl, Br
M = B(OH)$_2$, SnBu$_3$

Alternatively, compounds of Formula I can also be prepared from palladium catalyzed cross coupling of arylboronic acids of Formula Ib with halides R$_3$—X shown in Scheme 2.

Scheme 2

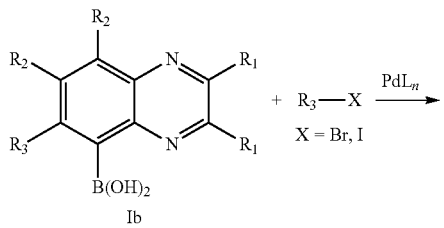

Ib

One way to prepare the quinoxalines of Formula Ia and Ib is through the condensation reaction of the diamine Ic with ketoaldehyde Id, as shown in Scheme 3. In general, the condensation will give two regioisomers that may be separated by chromatography. Structures of Formula Ia can be converted to boronic acid Ib via Suzuki-Miyaura reaction.

Scheme 3

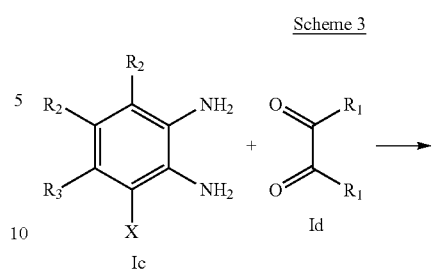

Ic    Id

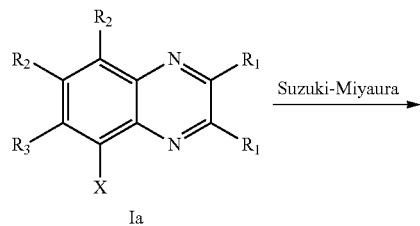

Ia

X = Cl, Br

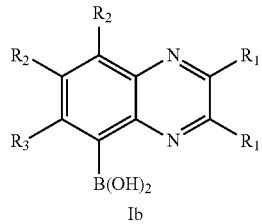

Ib

A regio specific synthesis of quinoxalines of Formula Ia and Ib is shown in Scheme 4. A properly protected ortho-nitro aniline Ie is alkylated with methyl bromoacetate to yield compound If. Deprotection of compound If and reduction of compound Ig should initiate cyclization to give rise to compound Ih. Compound Ih can be oxidized to quinoxaline-2-one of Formula Ii, which can be converted to the intermediate Ij with oxophosphorus halides. The halides in compound Ij can be displaced with a nucleophile containing an R$_1$ group to compound Ia, and compounds of Formula Ia can be converted to corresponding boronic acids of Formula Ib via Suzuki-Miyaura reaction. Intermediate Ii could also be converted to Ik by condensation reaction with sodium chlorodifluoroacetate in the presence of a base such as K$_2$CO$_3$. The difluoroalkoxy may be displaced with a nucleophile containing an R$_1$ group to compound Ia.

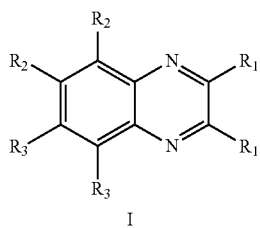

I

Scheme 4

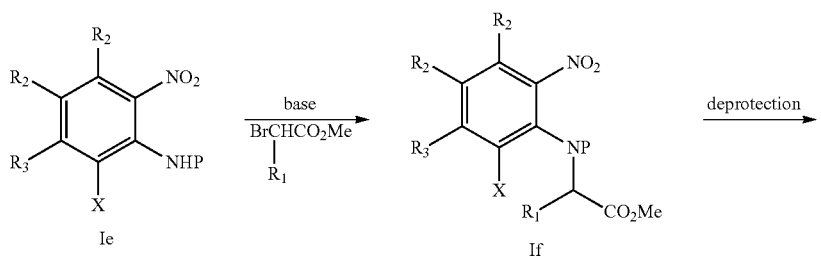

Ie    If

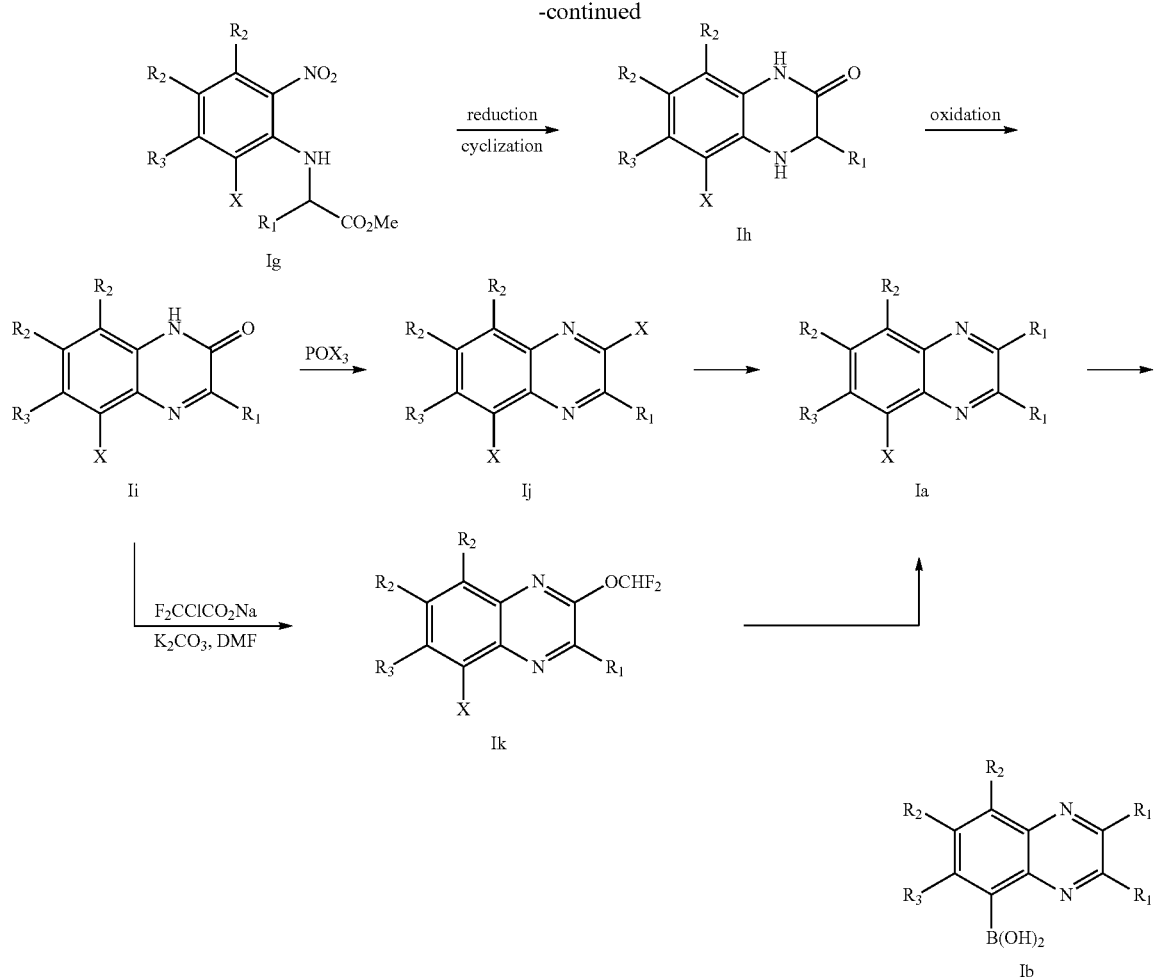

X = Cl, Br

General Methods

The following methods were used in the exemplified Examples, except where noted otherwise.

Products were analyzed by reverse phase analytical HPLC carried out on a Shimadzu Analytical HPLC system running Discovery VP software using one of the following methods:
Method A: PHENOMENEX® Luna C18 column (4.6×50 mm or 4.6×75 mm) eluted at 4 mL/min with a 2, 4 or 8 min gradient from 100% A to 100% B (A: 10% methanol, 89.9% water, 0.1% TFA; B: 10% water, 89.9% methanol, 0.1% TFA, UV 220 nm).
Method B: PHENOMENEX® Luna C18 column (4.6×50 mm) eluted at 4 mL/min with a 4 min gradient from 100% A to 100% B (A: 10% acetonitrile, 89.9% water, 0.1% TFA; B: 10% water, 89.9% acetonitrile, 0.1% TFA, UV 220 nm).

Reverse phase preparative HPLC was carried out using a Shimadzu Preparative HPLC system running Discovery VP software using one of the following methods.
Method A: PHENOMENEX® Axia Luna 5 μm C18 30×75 mm column with a 10 min gradient at 40 mL/min from 100% A to 100% B (A: 10% acetonitrile, 89.9% water, 0.1% TFA; B: 10% water, 89.9% acetonitrile, 0.1% TFA, UV 220 nm).
Method B: YMC Sunfire 5 μm C18 30×100 mm column with a 10 min gradient at 40 mL/min from 100% A to 100% B (A: 10% methanol, 89.9% water, 0.1% TFA; B: 10% water, 89.9% methanol, 0.1% TFA, UV 220 nm).

LCMS chromatograms were obtained on a Shimadzu HPLC system running Discovery VP software, coupled with a Waters ZQ mass spectrometer running MassLynx version 3.5 software using:
Method A: A linear gradient using solvent A (10% acetonitrile, 90% water, 0.1% of TFA) and solvent B (90% acetonitrile, 10% water, 0.1% of TFA); 0-100% of solvent B over 2 min and then 100% of solvent B over 1 min. Column: PHENOMENEX® Luna 3u C18(2) (2.0×30 mm). Flow rate was 5 ml/min, and UV detection was set to 220 nm. The LC column was maintained at room temperature.
Method B: A linear gradient using solvent A (10% methanol, 90% water, 0.1% of TFA) and solvent B (90% methanol, 10% water, 0.1% of TFA); 0-100% of solvent B over 4 min and then 100% of solvent B over 1 min. Column: PHENOMENEX® Luna 5u C18 (4.5×30 mm). Flow rate was 4 ml/min, and UV detection was set to 220 nm. The LC column was maintained at room temperature.

In addition, the following orthogonal HPLC conditions were used to check the purity of the compounds:
Two analytical LC/MS injections were used to determine the final purity. Injection1 condition: A linear gradient using solvent A (5% acetonitrile, 95% water, 0.05% TFA) and solvent B (95% acetonitrile, 5% water, 0.05% TFA); 10-100% of solvent B over 10 min and then 100% of solvent B over 5 min. Column: Sunfire C18 3.5 um (4.6×150 mm). Flow rate was 2 ml/min, and UV detection was set to 220 nm. The LC column was maintained at room temperature. Injection 2 conditions: A linear gradient using solvent A (5% acetonitrile, 95% water, 0.05% TFA) and solvent B (95% acetonitrile, 5% water, 0.05% TFA); 10-100% of solvent B over 10 min and then 100% of solvent B over 5 min. Column: Xbridge Phenyl 3.5 um (4.6×150 mm). Flow rate was 2 ml/min, and UV detection was set to 220 nm. The LC column was maintained at room temperature.

EXAMPLES

The invention is further defined in the following Examples. It should be understood that the Examples are given by the way of illustration only. From the above discussion and the Examples, one skilled in the art can ascertain the essential characteristics of the invention, and without departing from the spirit and scope thereof, can make various changes and modifications to adapt the invention to various uses and conditions. As a result, the invention is not limited by the illustrative examples set forth herein below, but rather is defined by the claims appended hereto.

ABBREVIATIONS

Boc tert-butoxycarbonyl
BOC$_2$O di(tert-butoxycarbonyl) ether
DMA dimethylacetamide
DCM dichloromethane
DMF dimethylformamide
DMAP dimethylaminopyridine
DMSO dimethyl sulfoxide
dppp bis(diphenylphosphino)propane
EtOAc ethyl acetate
EtOH ethanol
MeCN acetonitrile
MeOH methanol
PdCl$_2$(dppf)-CH$_2$Cl$_2$ [1,1'-bis(diphenylphosphino)ferrocene]dichloropalladium(II), dichloromethane adduct
TEA triethylamine
TFA trifluoroacetate
THF tetrahydrofuran
TLC thin layer chromatography
HPLC high pressure liquid chromatography
MS mass spectrometry
g gram(s)
h or hr hour(s)
min, minute(s)
mL milliliter(s)
mmol millimole(s)
RT retention time Intermediate I-1

2-(difluoromethoxy)-7-methyl-5-(4,4,5,5-tetramethyl-1,3,2-dioxaborolan-2-yl) quinoxaline

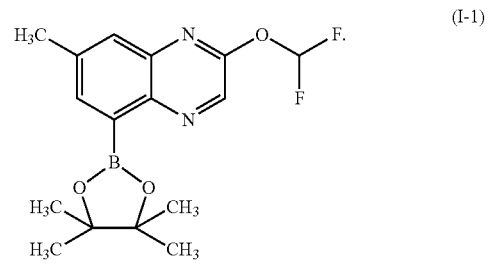 [SMILES: Cc1cc(B2OC(C)(C)C(C)(C)O2)c2ncc(OC(F)F)nc2c1]

Intermediate I-1A: tert-butyl N-(2-bromo-4-methyl-6-nitrophenyl)-N-[(tert-butoxy) carbonyl]carbamate

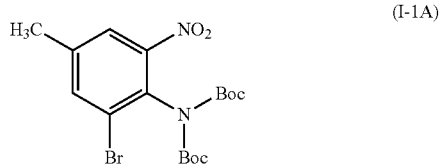 [SMILES: Cc1cc(Br)c(N(C(=O)OC(C)(C)C)C(=O)OC(C)(C)C)c([N+](=O)[O-])c1]

To a solution of 2-bromo-4-methyl-6-nitroaniline (9.6 g, 41.6 mmol) in THF (60 mL) was added DMAP (0.508 g, 4.16 mmol), followed by BOC$_2$O (22.67 g, 104 mmol) as a solid. The mixture was stirred at room temperature overnight. Solvent was removed by vacuum. The crude product was dissolved in a small amount of chloroform and charged to a 120 g silica gel cartridge (2 separate columns) which was eluted with 5% EtOAc in hexanes for 4 min., then a 12 min gradient from 5% to 30% EtOAc in hexanes. The desired fractions were combined and concentrated to give Intermediate I-1A (17.12 g, 39.7 mmol, 96% yield) as a white solid. $^1$H NMR (500 MHz, chloroform-d) δ 7.80-7.79 (m, 1H), 7.73 (dd, J=1.9, 0.8 Hz, 1H), 2.48 (s, 3H), 1.42 (s, 18H); LC-MS: method A, RT=1.90 min, MS (ESI) m/z: 230.0 and 232.0 (M−2 Boc)$^+$.

Intermediate I-1B: tert-butyl (2-bromo-4-methyl-6-nitrophenyl)carbamate

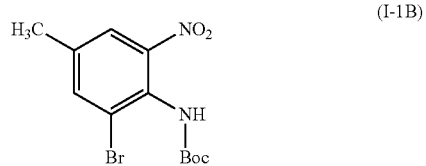 [SMILES: Cc1cc(Br)c(NC(=O)OC(C)(C)C)c([N+](=O)[O-])c1]

To a solution of Intermediate I-1A (17.1 g, 39.6 mmol) in dichloromethane (60 mL) was added TFA (6.11 mL, 79 mmol) and the mixture was stirred at room temperature for 1.0 h. The reaction was quenched by addition of saturated sodium bicarbonate, extracted with dichloromethane (3×), dried over sodium sulfate. After evaporation of solvent, Intermediate I-1B was obtained as a yellow solid (12.88 g, 88% yield): $^1$H NMR (500 MHz, chloroform-d) δ 7.71 (d, J=1.1 Hz, 1H), 7.68 (dd, J=1.9, 0.8 Hz, 1H), 2.42 (s, 3H), 1.51 (s, 9H); LC-MS: method A, RT=1.53 min. MS (ESI) m/z: 231.0 and 233.0 (M-Boc)$^+$.

Intermediate I-1C: methyl 2-((2-bromo-4-methyl-6-nitrophenyl)(tert-butoxycarbonyl) amino)acetate

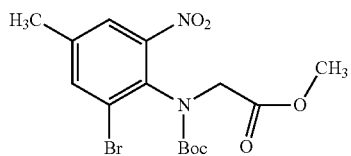

(I-1C)

Intermediate I-1B (12 g, 26.3 mmol) was dissolved in DMF (80 mL), cooled with a water bath. $C_{s2}CO_3$ (25.8 g, 79 mmol) was added. The dark brown solution was stirred at room temperature for 10 min, then methyl 2-bromoacetate (4.37 mL, 47.6 mmol) was added dropwise. After addition of methyl bromoacetate, the brown color faded to yellow. The mixture was stirred at room temperature for 1.0 h, diluted with EtOAc, and quenched with water. The organic layer was collected, washed with brine, dried over sodium sulfate. After evaporation of solvent, the crude product was dissolved in a small amount of chloroform and charged to a 330 g silica gel cartridge which was eluted with 5% EtOAc in hexanes for 5 min., then a 12 min gradient from 5% to 50% EtOAc in hexanes. The desired fractions were combined and concentrated to give Intermediate I-1C (15.2 g, 37.7 mmol, 95% yield) as an yellow oil. $^1$H NMR (500 MHz, chloroform-d) indicated a mixture of rotamers: δ 7.75-7.67 (m, 2H), 4.61-3.97 (m, 2H), 3.76 and 3.69 (s, 3H), 2.48 and 2.43 (s, 3H), 1.55 and 1.37 (s, 9H); LC-MS: method A, RT=1.70 min, MS (ESI) m/z: 303.0 and 305.0 (M-Boc)$^+$.

Intermediate I-1D: methyl 2-((2-bromo-4-methyl-6-nitrophenyl)amino)acetate

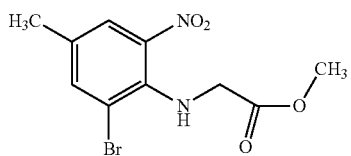

(I-1D)

To Intermediate I-1C (15.2 g, 37.7 mmol) was added 4.0 N HCl in dioxane (47.1 ml, 188 mmol) and the mixture was stirred at room temperature overnight. Solvent was removed under vacuum, chased with EtOAc (2×) to give Intermediate I-1D (13.6 g, 40.1 mmol, 106% yield) as a yellow solid. $^1$H NMR (500 MHz, methanol-d$_4$) δ 7.88 (dd, J=1.9, 0.6 Hz, 1H), 7.80 (dd, J=1.9, 0.6 Hz, 1H), 4.47 (d, J=17.3 Hz, 1H), 4.08 (d, J=17.1 Hz, 1H), 3.69 (s, 3H), 2.46 (s, 3H); LC-MS: Method A, RT=1.94 min. MS (ESI) m/z: 303.1 and 305.1 (M+H)$^+$.

Intermediate I-1E: 5-bromo-7-methyl-3,4-dihydroquinoxalin-2(1H)-one

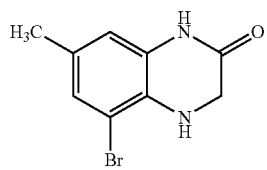

(I-1E)

To a solution of Intermediate I-1D (13.6 g, 40.1 mmol) in MeOH (100 mL) in a IL flask cooled with water bath was added concentrated HCl (13.35 mL, 160 mmol), followed by tin(II) chloride dihydrate (36.1 g, 160 mmol). The mixture was stirred at 68° C., for 2.5 h. MeOH was removed by vacuum. The crude was partitioned in water (100 mL)/EtOAc (200 mL), and the pH was adjusted to neutral with 4.0 N NaOH (ca 90 mL). The white precipitate formed was very fine particle that was very hard to remove by filtration. The mixture was transferred to a separatory funnel. The organic layer was collected. The aqueous was further extracted (2×200 mL) with EtOAc. The combined organic layer was washed with water (2×) and brine (2×), dried over sodium sulfate. After evaporation of solvent, Intermediate I-1E (8.36 g, 34.7 mmol, 87% yield) was obtained as a pale yellow solid. $^1$H NMR (500 MHz, DMSO-d$_6$) δ 10.37 (s, 1H), 6.87 (dd, J=1.8, 0.7 Hz, 1H), 6.56 (dd, J=1.1, 0.6 Hz, 1H), 5.46 (s, 1H), 3.76 (d, J=2.2 Hz, 2H), 2.14 (s, 3H); LC-MS: Method A, RT=1.66 min, MS (ESI) m/z: 241.0 and 243.0 (M+H)$^-$.

Intermediate I-1F: 5-bromo-7-methylquinoxalin-2-ol

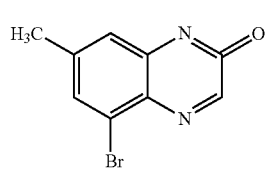

(I-1F)

To a suspension of Intermediate 1-1E (6.7 g, 27.8 mmol) in MeOH (50 mL) in a IL flask was added 30% hydrogen peroxide (28.4 mL, 278 mmol), followed by 4.0 N NaOH (20.84 mL, 83 mmol). The mixture was stirred at room temperature for 5 min, then gently heated at 60° C. After 15 min heating, the reaction turned strongly exothermic, suggesting an initiation of the reaction. The heating bath was removed and stirring continued for 30 min until the mixture turned completely clear. After cooling to room temperature with a water bath, MeOH was removed by vacuum. The mixture was then neutralized with 2.0 N HCl (to pH 2-3) and ice cooling. The precipitate formed was collected by filtration, washed with water, dried under vacuum in the air for 1.0 h and then at vacuum at 60° C., for 2.0 h, and under high vacuum to give Intermediate I-1F (6.55 g, 27.4 mmol, 99% yield) as an off-white solid. $^1$H NMR (500 MHz, DMSO-d$_6$) δ 12.52 (br. s., 1H), 8.17 (s, 1H), 7.49 (d, J=1.1 Hz, 1H), 7.08 (s, 1H), 2.40 (s, 3H; LC-MS: method A, RT=1.62 min, MS (ESI) m/z: 239.0 and 241.0 (M+H)$^+$.

Intermediate I-1G:
5-bromo-2-(difluoromethoxy)-7-methylquinoxaline

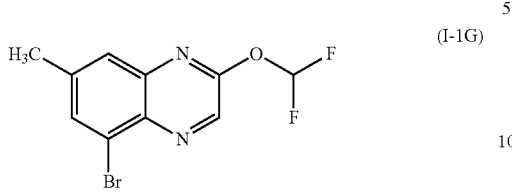

(I-1G)

A mixture of Intermediate I-1F (7.4 g, 26.9 mmol) and potassium carbonate (18.56 g, 134 mmol) in DMF (120 mL) was heated at 100° C., for 5 min. Sodium 2-chloro-2,2-difluoroacetate (16.40 g, 107.6 mmol) was added in one portion, and the mixture was stirred at 100° C., for 10 min. The mixture turned from yellow slurry to brown. The mixture was cooled to room temperature, diluted with EtOAc and water, extracted with EtOAc (3×). The combined organic layer was washed with brine, dried over sodium sulfate. After evaporation of solvent, the crude product was dissolved in a small amount of chloroform/toluene and purified with a 330 g ISCO column eluted with 5% dichloromethane in hexanes for 3 min, then 5-70% DCM/hexanes for 40 min (12 min gradient time). The desired fractions were combined, concentrated to give Intermediate I-1G (6.0 g, 20.76 mmol, 77% yield) as a slightly yellow solid. $^1$H NMR (500 MHz, chloroform-d) δ 8.64 (s, 1H), 7.89 (d, J=1.7 Hz, 1H), 7.68 (dd, J=1.8, 1.0 Hz, 1H), 7.63 (t, $J_{HF}$=71.80 Hz, 1H), 2.59 (s, 3H); $^{19}$F NMR (471 MHz, chloroform-d) δ −89.82 (s, 2F); LC-MS: method A, RT=2.09 min, MS (ESI) m/z: 289.0 and 291.0 (M+H)$^+$.

Intermediate I-1

A mixture of Intermediate I-1G (1.04 g, 3.60 mmol), 4,4,4',4',5,5,5',5'-octamethyl-2,2'-bi(1,3,2-dioxaborolane) (1.370 g, 5.40 mmol), potassium acetate (0.883 g, 8.99 mmol) and PdCl$_2$(dppf)-CH$_2$Cl$_2$ adduct (0.147 g, 0.180 mmol) in dioxane (14 mL) was degassed by bubbling argon for 10 min. The reaction vial was sealed and heated in microwave reactor at 135° C., for 30 min. The mixture was diluted with EtOAc/water, insoluble material was removed by filtration. The filtrate was extracted with EtOAc, washed with brine and dried over sodium sulfate. After evaporation of solvent, the crude product was dissolved in a small amount of toluene and charged to a 40 g silica gel cartridge which was eluted with 5% EtOAc in hexanes for 2 min., then a 18 min gradient from 5% to 75% EtOAc in hexanes. The desired fractions were concentrated and lyophilized to give Intermediate 1-1 (0.93 g, 72% yield) as a pale solid. $^1$HNMR was complicated by the presence of two sets of signals. $^{19}$FNMR indicated a single compound. $^{19}$F NMR (471 MHz, chloroform-d) δ −89.64 (s., 2F). LC-MS: method A, RT=2.01 min, MS (ESI) m/z: 225.0 (boronic acid)$^+$.

Example 1

3-(difluoromethoxy)-8-(4-methoxyphenyl)quinoxaline-6-carbonitrile

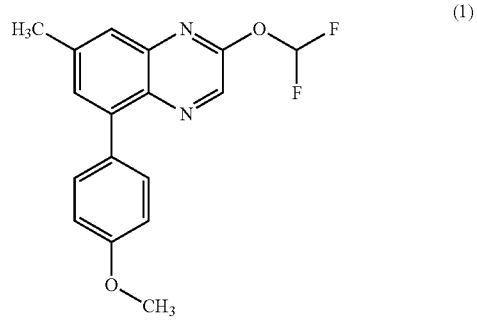 [SMILES: COc1ccc(-c2cc(C)cc3nc(OC(F)F)cnc23)cc1]

(1)

Intermediate 1A: 4-bromo-2-iodo-6-nitroaniline

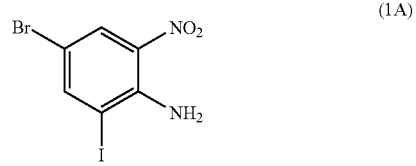 [SMILES: Nc1c(I)cc(Br)cc1[N+](=O)[O-]]

(1A)

4-Bromo-2-nitroaniline (1.4 g, 6.45 mmol) was added to iodine (1.801 g, 7.10 mmol) in EtOH (30 mL), followed by silver sulfate (2.213 g, 7.10 mmol). The reaction mixture was stirred at room temperature overnight and filtered. The solid was washed with EtOAc. The filtrate was concentrated. The crude product was dissolved in a small amount of chloroform and charged to a 120 g silica gel cartridge which was eluted with 5% for 3 min., then an 18 min gradient from 5% to 40%. The desired fractions were combined and concentrated to give Intermediate 1A (1.8 g, 5.25 mmol, 81% yield) as a brown solid. $^1$H NMR (500 MHz, methanol-d$_4$) δ 8.25 (d, J=2.2 Hz, 1H), 8.04 (d, J=2.2 Hz, 1H), LC-MS: method A, RT=2.08 min, No MS (ESI) was observed.

Intermediate 1B:
5-bromo-3-iodobenzene-1,2-diamine

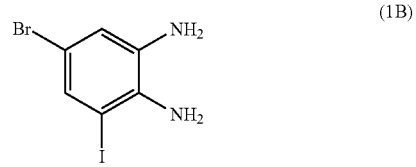

(1B)

To a solution of Intermediate 1A (4.5 g, 13.12 mmol) in EtOH (80 mL) was added concentrated HCl (5.47 mL, 65.6 mmol), followed by tin(II) chloride dihydrate (11.84 g, 52.5 mmol). The reaction mixture was stirred at 60° C. overnight. After cooled to room temperature, it was treated with an ice-cold 4.0 N NaOH (18 mL) and EtOAc/water. After stirring for 10 min, the white solid was removed by filtration.

The filtrate was separated, the organic layer was collected, washed with brine and dried over sodium sulfate. After evaporation of solvent, the crude product was dissolved in a small amount of chloroform and charged to an 80 g silica gel cartridge which was eluted with 5% for 3 min., then a 12 min gradient from 5% to 50%. The desired fractions were combined and concentrated to give Intermediate 1B (3.3 g, 10.55 mmol, 80% yield) as a pale brown solid. 1H NMR (500 MHz, chloroform-d) δ 7.33 (d, J=2.2 Hz, 1H), 6.83 (d, J=1.9 Hz, 1H), 3.81 (br. s., 2H), 3.54 (br. s., 2H); LC-MS: method A, RT=1.82 min, MS (ESI) m/z: 312.8 and 313.8 (M+H)+.

Intermediate 1C:
7-bromo-2-(difluoromethoxy)-5-iodoquinoxaline

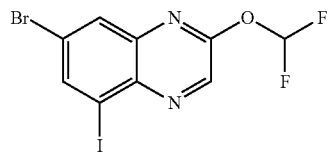

To a solution of Intermediate 1B (3.3 g, 10.55 mmol) in ethanol (40 mL) was added ethyl 2-oxoacetate (50% in PhMe) (2.58 mL, 12.65 mmol). The mixture was heated at 45° C., for 2.0 h. After cooled to room temperature, the precipitate was collected by filtration, washed with EtOH to give a mixture of 7-bromo-5-iodoquinoxalin-2-ol and 6-bromo-8-iodoquinoxalin-2-ol (2.83 g, 8.06 mmol, 76% yield). $^1$H NMR indicated a mixture of two isomers. LC-MS: method A, RT=1.80 and 1.88 min, MS (ESI) m/z: 351.0 and 353.0 (M+H)+. The mixture of isomers was used for the next step.

A mixture of 7-bromo-5-iodoquinoxalin-2-ol and 6-bromo-8-iodoquinoxalin-2-ol (2.82 g, 8.04 mmol) and potassium carbonate (22.21 g, 161 mmol) in DMF (50 mL) and water (2.5 mL) was heated at 90° C., for 4 min, then sodium 2-chloro-2,2-difluoroacetate (4.90 g, 32.1 mmol) was added. After 15 min at 90° C., another portion of sodium 2-chloro-2,2-difluoroacetate (4.90 g, 32.1 mmol) was added. After 15 min at 90° C., a third portion of sodium 2-chloro-2,2-difluoroacetate (4.90 g, 32.1 mmol) was added. A fourth portion of sodium 2-chloro-2,2-difluoroacetate (4.90 g, 32.1 mmol) was added after 15 min at 90° C. After completion of the reaction, it was cooled to room temperature, diluted with dichloromethane/water. The reaction mixture was stirred at room temperature for 15 min, the insoluble material was removed by filtration. The filtrate was collected and extracted with dichloromethane. The organic layer was washed with brine, dried over sodium sulfate. After evaporation of solvent, the crude product was dissolved in a small amount of toluene and charged to a 120 g silica gel cartridge which was eluted with 5% for 5 min. then an 18 min gradient from 5% to 40%. The desired fractions were combined and concentrated to give Intermediate 1C (0.625 g, 1.559 mmol, 19.40% yield): as a white solid: $^1$H NMR (500 MHz, dichloromethane-d$_2$) δ 8.66 (s, 1H), 8.46 (d, J=2.2 Hz, 1H), 8.14 (d, J=1.9 Hz, 1H), 7.65 (t, J$_{HF}$=71.25 Hz, 1H); $^{19}$F NMR (471 MHz, dichloromethane-d$_2$) δ −90.28 (s, 1F); LC-MS: method A. RT=2.29 min, MS (ESI) m/z: MS not detected.

Intermediate 1D: 7-bromo-2-(difluoromethoxy)-5-(4-methoxyphenyl)quinoxaline

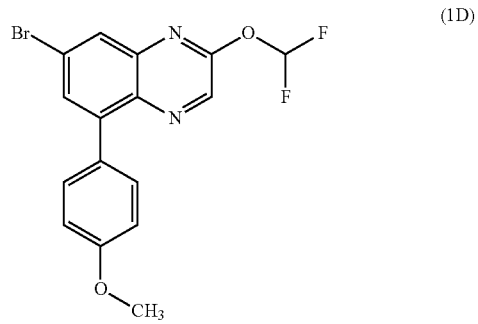 [SMILES: COc1ccc(-c2cc(Br)cc3nc(OC(F)F)cnc23)cc1]

A mixture of Intermediate 1C (725 mg, 1.808 mmol), (4-methoxyphenyl)boronic acid (302 mg, 1.989 mmol) and PdCl$_2$(dppf)-CH$_2$Cl$_2$ adduct (89 mg, 0.108 mmol) in toluene (12 mL) and EtOH (4.00 mL) was degassed with argon. To this solution was added sodium carbonate (2M, 1.582 mL, 3.16 mmol). The mixture was heated in a pressure flask at 75° C. overnight. HPLC indicated a completion of the reaction. It was diluted with EtOAc/water. The organic layer was collected, washed with brine, dried over sodium sulfate. After evaporation of solvent, the crude product was dissolved in a small amount of toluene and charged to a 40 g silica gel cartridge which was eluted with 5% for 3 min., then a 15 min gradient from 5% to 60%. The desired fractions were combined and concentrated to give Intermediate 1D (540 mg, 1.417 mmol, 78% yield) as yellow solid. $^1$H NMR (500 MHz, acetonitrile-d$_3$) δ 8.69 (s, 1H), 8.29 (d, J=2.2 Hz, 1H), 8.00 (d, J=2.2 Hz, 1H), 7.71-7.67 (m, 2H), 7.48 (t, J$_{HF}$=71.53 Hz, 1H), 7.12-7.07 (m, 2H), 3.90 (s, 3H); $^{19}$F NMR (471 MHz, acetonitrile-d$_3$) δ −90.44 (s, 2F); LC-MS: method A, RT=2.40 min, MS (ESI) m/z: 381.0 and 383.0 (M+H)+.

Example 1

A mixture of Intermediate 1D (37 mg, 0.097 mmol), zinc cyanide (6.84 mg, 0.058 mmol), palladium (II) trifluoroacetate (2.58 mg, 7.77 μmol) and zinc dust (1.269 mg, 0.019 mmol) in DMA (1.0 mL) was degassed by bubbling argon for 5 min. Then racemic-2-(di-tert-butylphosphino)-1,1'-binaphthyl (6.19 mg, 0.016 mmol) was added. The reaction vessel was sealed, stirred at room temperature for 10 min and heated at 90° C. overnight. The reaction mixture was diluted with EtOAc/saturated sodium bicarbonate. The insoluble was removed by filtration. The filtrate was collected, organic layer was washed with brine, dried over sodium sulfate. After evaporation of solvent, the crude residue was purified using a preparative HPLC (method A, 40-100% B in 10 min; with a flow rate of 40 mL/min). The desired fractions were concentrated and lyophilized to give Example 1 (16 mg, 0.047 mmol, 48.9% yield). $^1$H NMR (400 MHz, acetonitrile-d$_3$) δ 8.72 (s, 1H), 8.25 (d, J=1.6 Hz, 1H), 7.98 (d, J=1.6 Hz, 1H), 7.67 (t, J$_{HF}$=71.46 Hz, 1H) 7.62-7.58 (m, 2H), 7.09-7.05 (m, 2H), 3.87 (s, 3H); $^{19}$F NMR (376 MHz, acetonitrile-d$_3$) δ −90.24 (d, J$_{HF}$=68.36 Hz 2F); LC-MS: method A, RT=2.13 min, MS (ESI) m/z: 328.0 (M+H)+. Analytical HPLC purity: 96%.

Example 2

7-Chloro-2-(difluoromethoxy)-5-(4-methoxyphenyl)quinoxaline

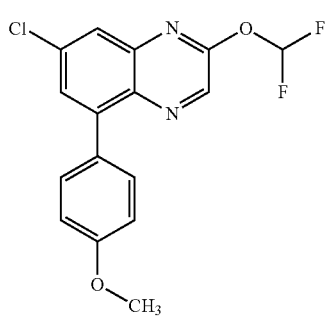

(2)

Intermediate 2A: 2-(difluoromethoxy)-5-(4-methoxyphenyl)-7-(4,4,5,5-tetramethyl-1,3,2-dioxaborolan-2-yl)quinoxaline

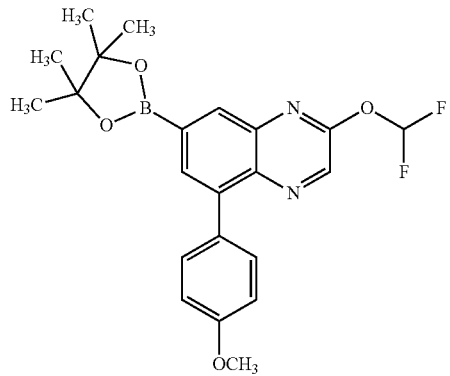

(2A)

A mixture of Intermediate 1D (140 mg, 0.367 mmol), 4,4,4',4',5,5,5',5'-octamethyl-2,2'-bi(1,3,2-dioxaborolane) (107 mg, 0.422 mmol), potassium acetate (90 mg, 0.918 mmol) and $PdCl_2(dppf)\text{-}CH_2Cl_2$ adduct (24.00 mg, 0.029 mmol) in dioxane (3 mL) was degassed by bubbling argon for 5 min. It was heated at 90° C., for 2.5 h and at 80° C. overnight. The mixture was diluted with EtOAc/water and insoluble material was removed by filtration. The filtrate was extracted with EtOAc, washed with brine and dried over sodium sulfate. After evaporation of solvent, the crude product was dissolved in a small amount of toluene and charged to a 12 g silica gel cartridge which was eluted with 5% for 3 min., then a 12 min gradient from 5% to 40%. The desired fractions were combined and concentrated to give Intermediate 2A (142 mg, 0.332 mmol, 90% yield) as a slightly yellow solid. $^1$H NMR (500 MHz, chloroform-d) δ 8.66 (s, 1H), 8.38 (d, J=1.4 Hz, 1H), 8.10 (d, J=1.1 Hz, 1H), 7.67 (t, $J_{HF}$=72.08 Hz, 1H), 7.64-7.60 (m, 2H), 7.08-7.04 (m, 2H), 3.91 (s, 3H), 1.42 (s, 12H); $^{19}$F NMR (471 MHz, chloroform-d) δ −89.84 (s, 2F); LC-MS: method A, RT=2.36 min, MS (ESI) m/z: 429.1 (M+H)$^-$.

To Intermediate 2A (15.5 mg, 0.036 mmol) dissolved in MeOH (1.0 mL) in a microwave vial was added copper (II) chloride (16 mg, 0.12 mmol) dissolved in water (0.6 mL). The cloudy solution was heated at 90° C., for 3.0 h and then left stirring at room temperature overnight. The mixture was diluted with EtOAc/water, the organic layer was washed with brine, dried over sodium sulfate and concentrated. The crude residue was purified using a preparative HPLC (method A, 60-100% B in 10 min, flow rate of 40 mL/min). The desired fractions were placed in a SpeedVac overnight to remove solvent, then lyophilized to give Example 2 (9 mg, 0.026 mmol, 72.4% yield) as a white lyophilate. $^1$H NMR (500 MHz, acetonitrile-d$_3$) δ 8.64 (s, 1H), 7.90 (d, J=2.5 Hz, 1H), 7.69 (t, $J_{HF}$=71.80 Hz, 1H), 7.78 (d, J=2.5 Hz, 1H), 7.65-7.61 (m, 2H), 7.11-7.07 (m, 2H), 3.90 (s, 3H); $^{19}$F NMR (471 MHz, acetonitrile-d$_3$) δ −90.23 (s, 2F); LC-MS: Method A, RT=2.35 min, MS (ESI) m/z: 337.0 (M+H)$^+$. Analytical HPLC purity: 98%.

Example 3

2-(difluoromethoxy)-5-(4-methoxyphenyl)-7-vinylquinoxaline

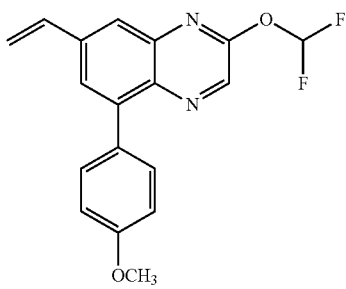

(3)

A solution of Intermediate 1D (50 mg, 0.131 mmol) and tetrakis (triphenylphosphine)palladium(0) (7.58 mg, 6.56 µmol) in toluene (1.5 mL) was degassed with argon for 3 min. Tributyl(vinyl)stannane (0.046 mL, 0.157 mmol) was added from a syringe. The mixture was sealed and heated in a microwave reactor at 110° C., for 30 min. Solvent was removed under vacuum. The crude residue was purified using a preparative HPLC (method A, 55-100% B in 10 min, flow rate of 40 mL/min). The desired fractions were placed in a SpeedVac overnight to remove solvent, then lyophilized to give Example 3 (37 mg, 0.112 mmol, 85% yield) as a white lyophilate. $^1$H NMR (500 MHz, acetonitrile-d$_3$) δ 8.57 (s, 1H), 7.92 (d, J=1.9 Hz, 1H), 7.85-7.83 (m, 1H), 7.69 (t, $J_{HF}$=71.80 Hz, 1H); 7.65-7.61 (m, 2H), 7.10-7.06 (m, 2H), 7.02 (dd, J=17.7, 10.9 Hz, 1H), 6.14 (d, J=17.6 Hz, 1H), 5.55 (d, J=11.0 Hz, 1H), 3.90 (s, 3H); $^{19}$F NMR (471 MHz, acetonitrile-d$_3$) δ −90.00 (s, 2F); LC-MS: method A, RT=2.33 min, MS (ESI) m/z: 329.0 (M+H)$^+$. Analytical HPLC purity: 99%.

Example 4

Methyl 3-(difluoromethoxy)-8-(4-methoxyphenyl) quinoxaline-6-carboxylate

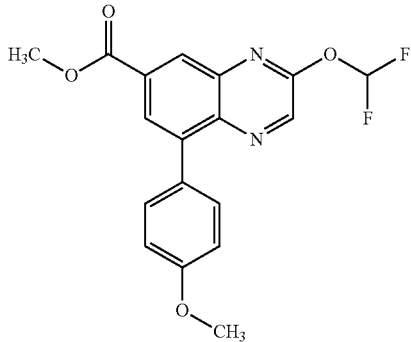
(4)

To a solution of Intermediate 1D (115 mg, 0.302 mmol) in DMSO (4.0 mL)/MeOH (2.000 mL) was added palladium (II) acetate (10.84 mg, 0.048 mmol), dppp (19.91 mg, 0.048 mmol) and TEA (0.126 mL, 0.905 mmol). The resulting mixture was purged (3×), charged with carbon monoxide at 40 psi in a pressured bottle and stirred at 70° C. overnight. The reaction was quenched with brine/EtOAc. The organic layer was washed with brine (3×), dried over sodium sulfate. After evaporation of solvent, the crude product was dissolved in a small amount of chloroform/toluene and charged to a 4 g silica gel cartridge which was eluted with 5% for 2 min., then a 10 min gradient from 5% to 60%. The desired fractions were combined and concentrated to give Example 4 (108 mg, 0.288 mmol, 95% yield) as a slightly yellow solid. $^1$H NMR (500 MHz, chloroform-d) δ 8.71 (s, 1H), 8.58 (d, J=1.9 Hz, 1H), 8.34 (d, J=1.9 Hz, 1H), 7.69 (t, J, = 71.53 Hz, 1H), 7.65-7.61 (m, 2H), 7.10-7.06 (m, 2H), 4.05 (s, 3H), 3.92 (s, 3H); $^{19}$F NMR (471 MHz, chloroform-d) δ −89.90 (s, 2F); LC-MS: Method A, RT=2.04 min, MS (ESI) m/z: 361.0 (M+H)$^+$. Analytical HPLC purity: 96%.

Example 5

2-(difluoromethoxy)-7-ethynyl-5-(4-methoxyphenyl) quinoxaline

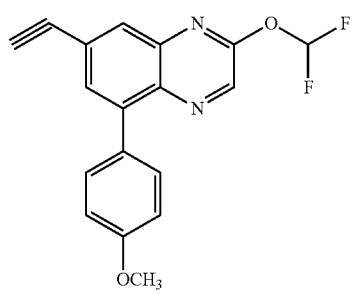
(5)

Intermediate 5A: 2-(difluoromethoxy)-5-(4-methoxyphenyl)-7-(((trimethylsilyl)ethynyl) quinoxaline

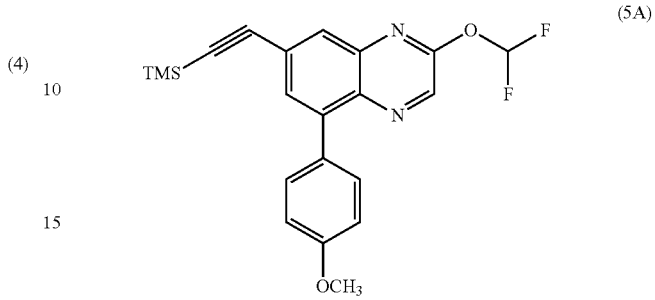
(5A)

To Intermediate 1D (47.5 mg, 0.125 mmol), bis(triphenylphosphine)palladium(II) dichloride (8.75 mg, 0.012 mmol) and copper(I) iodide (2.373 mg, 0.012 mmol) in TEA (1.042 mL, 7.48 mmol) and THF (0.5 mL) was added ethynyltrimethylsilane (0.031 mL, 0.218 mmol). The mixture was degassed with argon for 2 min, and then sealed and heated at 70° C. overnight. The reaction mixture was diluted with EtOAc (3.0 mL), filtered to remove the solid material. The filtrate was concentrated, dissolved in a small amount of chloroform and charged to a 4 g silica gel cartridge which was eluted with 5% for 2 min., then a 10 min gradient from 5% to 50%. The desired fractions were combined and concentrated to give Intermediate 5A (50 mg, 0.125 mmol, 101% yield) as a white solid. $^1$H NMR (500 MHz, methanol-d$_4$) δ 8.53 (d, J=1.9 Hz, 1H), 7.93 (s, 1H), 7.71 (s, 1H), 7.61 (t, J$_{HF}$=71.80 Hz, 1H), 7.56-7.51 (m, 2H), 7.01 (d, J=7.4 Hz, 2H), 3.86 (d, J=1.1 Hz, 3H), 0.26 (d, J=1.4 Hz, 8H); $^{19}$F NMR (471 MHz, methanol-d$_4$) δ −90.09 (s, 1F); LC-MS: method A, RT=2.99 min, MS (ESI) m/z: 399.1 (M+H)$^+$.

Example 5

To Intermediate 5A (50 mg, 0.125 mmol) in THF (0.7 mL) and MeOH (2.1 mL) was added potassium carbonate (52.0 mg, 0.376 mmol). The reaction mixture was stirred at room temperature for 1.0 h. Solvent was removed. The crude product was partitioned between EtOAc/0.2 N HCl. The organic layer was washed with brine, dried over sodium sulfate. After evaporation of solvent, the crude product was dissolved in a small amount of chloroform and charged to a 4 g silica gel cartridge which was eluted with 5% for 2 min., then a 10 min gradient from 5% to 50%. The desired fractions were combined and concentrated to give Example 5 (10 mg, 0.030 mmol, 23.69% yield). $^1$H NMR (500 MHz, acetonitrile-d$_3$) δ 8.63 (s, 1H), 7.98 (d, J=1.9 Hz, 1H), 7.69 (t, J$_{HF}$=71.80 Hz, 1H), 7.81 (d, J=1.9 Hz, 1H), 7.63-7.59 (m, 2H), 7.10-7.06 (m, 2H), 3.89 (s, 3H), 3.69 (s, 1H); $^{19}$F NMR (471 MHz, acetonitrile-d$_3$) δ −90.15 (s, 2F); LC-MS: method A, RT=2.10 min, MS (ESI) m/z: 327.0 (M+H)$^+$. Analytical HPLC purity: 99%.

Example 6

2-(difluoromethoxy)-5-(4-methoxyphenyl)-7-methylquinoxaline

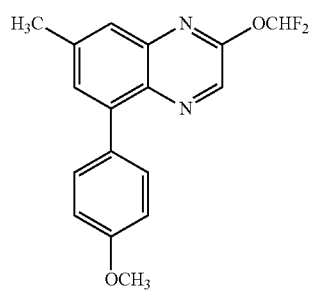

(6)

To Intermediate I-1G (20 mg, 0.069 mmol) and (4-methoxyphenyl)boronic acid (15.77 mg, 0.104 mmol) was added toluene (0.75 mL) and EtOH (0.25 mL). The reaction mixture was stirred at room temperature until solids are dissolved, then PdCl$_2$(dppf)-CH$_2$Cl$_2$ adduct (3.39 mg, 4.15 µmol) was added. The flask was degassed and flushed with argon. Finally sodium carbonate (0.042 mL, 2M, 0.083 mmol) was added dropwise. The reaction vessel was sealed and bubbled with argon for 5 min, then placed in microwave reactor at 120° C., for 30 min. LCMS indicated completion of the reaction. The reaction mixture was cooled to room temperature and was diluted with EtOAc and water, extracted with EtOAc (3×). The combined organic layer was washed with brine, dried with MgSO$_4$ and concentrated. The crude sample was purified using a preparative HPLC (method A, 50-100% B in 10 min. then 100% B for 2 min.). The desired fractions were placed in a SpeedVac overnight to remove solvent, then lyophilized to give Example 6 (12 mg, 0.037 mmol, 53.7% yield). $^1$H NMR (400 MHz, acetonitrile-d$_3$) δ 8.55 (s, 1H), 7.87-7.49 (m, 5H), 7.10-7.02 (m, 2H), 3.88 (s, 3H), 2.61 (s, 3H); $^{19}$F NMR (376 MHz, acetonitrile-d$_3$) δ −90.43 (s, 2F). LC-MS: method B, RT=4.31 min, MS (ESI) m/z: 317.0 (M+H)$^+$. Analytical HPLC purity: 99%.

Two analytical LC/MS injection conditions were used to determine the final purity of products unless indicated otherwise. Condition 1: Column:Waters BEH C18, 2.0×50 mm, 1.7-µm particles; Mobile Phase A: 5:95 acetonitrile: water with 10 mM ammonium acetate; Mobile Phase B: 95:5 acetonitrile:water with 10 mM ammonium acetate: Temperature: 40° C.; Gradient: 0.5 min hold at 0% B, 0-100% B over 4 minutes, then a 0.5-minute hold at 100% B: Flow: 1 mL/min. Condition 2: Column:Waters BEH C18, 2.0×50 mm, 1.7-µm particles; Mobile Phase A: 5:95 ethanol: water with 10 mM ammonium acetate; Mobile Phase B: 95:5 methanol:water with 10 mM ammonium acetate; Temperature: 40° C.; Gradient: 0.5 min hold at 0% B, 0-100% B over 4 minutes, then a 0.5-minute hold at 100% B; Flow: 0.5 mL/min.

Example 7

2-(difluoromethoxy)-6-(4-methoxyphenyl)-7-(trifluoromethyl)quinoxaline

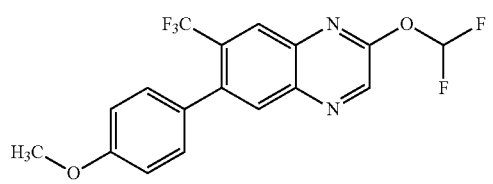

(7)

Intermediate 7A: 6-bromo-7-(trifluoromethyl)quinoxalin-2(1H)-one

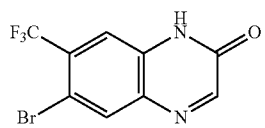

(7A)

4-bromo-5-(trifluoromethyl)benzene-1,2-diamine (J. Med. Chem., 2006, 49(12), 3719-3742) (4 g, 15.68 mmol) ethanol (40 mL) and ethyl 2-oxoacetate (3.84 g, 18.82 mmol) were combined in a microwave vial. The reaction mixture was heated to 80° C., for 2 hr in a microwave. This procedure was repeated three times and the combined crude material was filtered. The white solid was washed with ethanol to give 10.5 g. The material was stirred in 50 mL DMF at 80° C., for 10 minutes and immediately filtered. The white solid was washed again with ethanol to give 5.1 g of 7-bromo-6-(trifluoromethyl)quinoxalin-2(1H)-one. The filtrates were combined, concentrated and purified on silica gel with 25% ethyl acetate in hexanes to give a mixture of isomers. 6-bromo-7-(trifluoromethyl)quinoxalin-2(1H)-one (2 g) was isolate by supercritical fluid chromatography. $^1$H NMR (300 MHz, DMSO-d$_6$) δ 8.33 (s, 1H), 8.24 (3, 1H), 7.70 (s, 1H). LC/MS (condition 1) 1.8 min., M-1:293.0 and 291.0. Exact Mass: 293.9 and 291.9.

Intermediate 7B: 6-(4-methoxyphenyl)-7-(trifluoromethyl)quinoxalin-2-ol

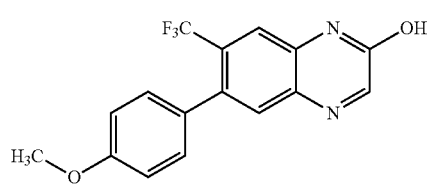

(7B)

A mixture of 6-bromo-7-(trifluoromethyl)quinoxalin-2-ol (117 mg, 0.399 mmol), (4-methoxyphenyl)boronic acid (91 mg, 0.599 mmol) and [1,1'-bis(diphenylphosphino) ferrocene]dichloropalladium (II) complex with dichloromethane (1:1) (19.56 mg, 0.024 mmol) in toluene (2994 μl) and ethanol (998 μl) was placed under argon. To this solution was added aqueous sodium carbonate, 2M (399 μl, 0.799 mmol). The mixture was then heated in a microwave at 120° C., for 30 min. The reaction mixture was cooled and diluted with 20 mL ethyl acetate and 5 mL water. The organic portion was concentrated by rotatory evaporation. The crude product was dissolved in a minimum amount of dichloromethane and charged to a 12 g silica gel cartridge and eluted with 20-80% ethyl acetate in hexane. Isolated a mixture of starting material and desired product. Used without further purification. LC/MS (condition 1) 2.7 min., M-1:319.5. Exact Mass: 320.3.

Example 7

Sodium 2-chloro-2,2-difluoroacetate (122 mg, 0.800 mmol), 6-(4-methoxyphenyl)-7-(trifluoromethyl)quinoxalin-2-ol (64.1 mg, 0.2 mmol) and cesium carbonate (163 mg, 0.500 mmol) in DMF (2000 μl) were combined and heated in the microwave at 95° C., for 20 minutes. The crude material was purified via preparative LC/MS with the following conditions: Column:Waters XBridge C18, 19×200 mm, 5-μm particles: Guard Column:Waters XBridge C18, 19×10 mm, 5-μm particles; Mobile Phase A: water; Mobile Phase B: methanol; Buffer: 0.1% TFA; Gradient: 40-95% B over 19.5 minutes, then a 14.0 minute hold at 95% B: Flow: 20 mL/min. Fractions containing the desired product were combined and dried via centrifugal evaporation. The yield of the product was 15.4 mg, and its estimated purity by LCMS analysis was 98%. LCMS (Condition 2) 4.5 min., M+1=371.5, EM=370.1. $^1$H NMR (500 MHz, DMSO-$d_6$) δ 9.07-9.02 (m, 1H), 8.38-8.34 (m, 1H), 8.09-8.08 (m, 1H), 7.92 (t, J=71.0 Hz, 1H), 7.42-7.35 (m, 2H), 7.12-7.03 (m, 2H), 3.85 (s, 3H).

Example 8

2-(difluoromethoxy)-5-(4-methoxyphenyl)-7-(trifluoromethyl)quinoxaline

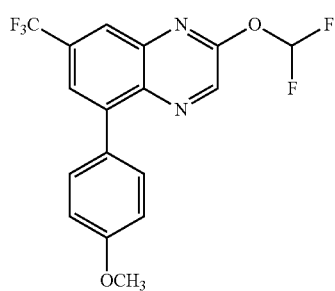

(8)

Intermediate 8A:
5-bromo-7-(trifluoromethyl)quinoxalin-2-ol

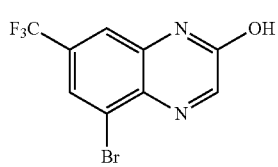

(8A)

To a solution of 3-bromo-5-(trifluoromethyl)benzene-1,2-diamine (3400 mg, 12.93 mmol) in ethanol (40 ml) was added ethyl 2-oxoacetate (2904 mg, 14.22 mmol). The reaction mixture was stirred at room temperature for two nights. The mixture was filtered and washed with DMF. The filtrate was purified by prep-HPLC, MeOH-TFA-H$_2$O, Phenomenex-Luna Column 30×100 mm (20% B-100% B, 15 min) to collect the desired product as white solid. $^1$H NMR (400 MHz, chloroform-d) δ 8.55 (s, 1H), 7.91 (d, J=1.5 Hz, 1H), 7.55 (d, J=1.0 Hz, 1H) containing approximately 20% of the undesired 8-bromo-6-(trifluoromethyl)quinoxalin-2-ol. $^1$H NMR (400 MHz, chloroform-d) δ 8.37 (s, 1H), 8.19-8.13 (m, 1H), 8.05-7.99 (m, 1H).

Intermediate 8B: 5-(4-methoxyphenyl)-7-(trifluoromethyl)quinoxalin-2-ol

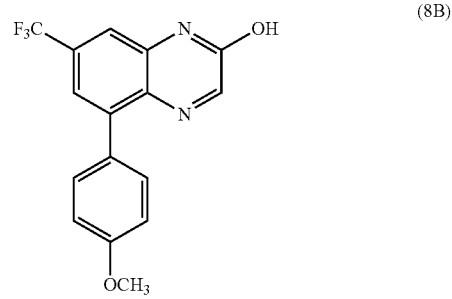 [SMILES: COc1ccc(-c2cc(C(F)(F)F)cc3nc(O)cnc23)cc1]

(8B)

A DMF (20 mL) solution of 5-bromo-7-(trifluoromethyl)quinoxalin-2-ol (g, 3.41 mmol), (4-methoxyphenyl)boronic acid (0.570 g, 3.75 mmol), and aqueous potassium phosphate (2N, 5.12 mL, 10.24 mmol) was filled placed under argon. Tetrakistriphenylphosphine palladium (0.079 g, 0.068 mmol) was added and the mixture heated at 70° C., for 2 hr. After cooling, the mixture was diluted with ethyl acetate, washed with brine and dried over sodium sulfate. The residue was purified with 5:1 hexane:ethyl acetate on a 50 g silica gel column. Collected fractions to obtain 630 mg (55%) of the desired product as yellow solid. LCMS: (Condition 2) 2.1 min., M+1=321.1, EM=320.1. $^1$H NMR (500 MHz, DMSO-$d_6$) δ 11.48 (br. s., 1H), 8.32 (s, 1H), 8.11 (d, J=1.4 Hz, 1H), 7.66 (d, J=1.9 Hz, 1H), 7.46-7.41 (m, 2H), 7.12-7.08 (m, 2H), 3.32 (s, 3H); $^{19}$F NMR (471 MHz, DMSO-$d_6$) δ −60.28 (s, 3F).

Example 8

2-(difluoromethoxy)-5-(4-methoxyphenyl)-7-(trifluoromethyl)quinoxaline was prepared from 5-(4-methoxyphenyl)-7-(trifluoromethyl)quinoxalin-2-ol according to Example 8 in 16% yield as a white lyophilate: $^1$H NMR (500 MHz, Acetonitrile-$d_3$) δ 8.76 (s, 1H), 8.20 (dd, J=1.9, 0.8 Hz, 1H), 7.98 (d, J=1.9 Hz, 1H), 7.72 (t, J$_{HF}$=71.5 Hz, 1H), 7.67-7.63 (m, 2H), 7.12-7.08 (m, 2H); $^{19}$F NMR (471 MHz, Acetonitrile-d) δ −63.18 (s, 3F), −90.36 (s, 2F); LCMS: (Phenom. Luna C18 30×4.6 mm 5 m; A: 10% MeCN-90% H2O-0.1% TFA; B: 90% MeCN-10% H$_2$O-0.1% TFA; wavelength 220 nm; flow rate 5 mL/min; gradient time 2 min; 0 to 100% B. RT=2.39 min.) M+1=371.0, EM=370.1 (M+H)$^+$.

Example 9

2-(difluoromethoxy)-5-(4-methoxy-3-(trifluoromethyl)phenyl)-7-(trifluoromethyl)quinoxaline

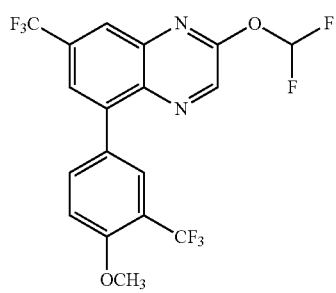

(9)

The title compound was prepared was prepared from 5-bromo-7-(trifluoromethyl) quinoxalin-2-ol and the appropriate boronic acid using Procedures 5 and 3. $^1$H NMR (500 MHz, DMSO-$d_6$) δ 9.03 (s, 1H), 8.30 (s, 1H), 8.14 (d, J=1.8 Hz, 1H), 8.01-7.97 (m, 1H), 7.96 (d, J=2.1 Hz, 11), 7.93 (t, J=71.3 Hz, 1H), 7.45 (d, J=8.9 Hz, 1H), 4.00 (s, 3H). LCMS: (Condition 2) 4.6 min., M+1=439.2, EM=438.1.

Example 10

2-(difluoromethoxy)-5-(3-methoxyphenyl)-7-(trifluoromethyl)quinoxaline

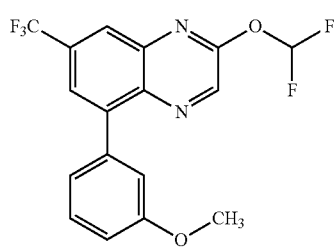

(10)

The title compound was prepared from 5-bromo-7-(trifluoromethyl)quinoxalin-2-ol and the appropriate boronic acid using Procedures 5 and 3. $^1$H NMR (500 MHz, DMSO-$d_6$) δ 9.01 (s, 1-), 8.31 (s, 1H), 8.06 (d, J=1.8 Hz, 1H), 7.93 (t, J=71.3 Hz, 1H), 7.50-7.41 (m, 1H), 7.27-7.22 (m, 2H), 7.10 (s, 1H), 3.84 (s, 3H). LCMS: (Condition 2) 4.6 min., M+1=371.1, EM=370.1.

Example 11

2-(difluoromethoxy)-5-(6-methoxynaphthalen-2-yl)-7-(trifluoromethyl)quinoxaline

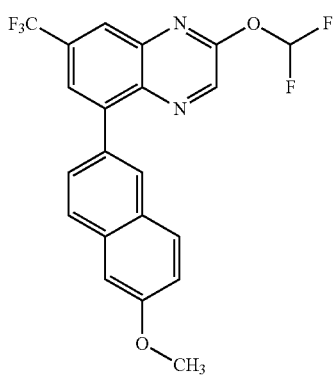

(11)

The title compound was prepared from 5-bromo-7-(trifluoromethyl)quinoxalin-2-ol and the appropriate boronic acid using Procedures 5 and 3. $^1$H NMR (400 MHz, chloroform-d) δ 8.74 (s, 1H), 8.21-8.17 (m, 1H), 7.91 (d, J=2.0 Hz, 1H), 7.68 (t, J=71.3 Hz, 1H), 7.64-7.59 (m, 21-), 7.11-7.06 (m, 2H), 3.92 (s, 3H). LCMS: (Condition 2) 4.7 min., M+1=421.1, EM=420.1.

Example 12

2-(difluoromethoxy)-5-(3-fluoro-4-methoxyphenyl)-7-trifluoromethyl)quinoxaline

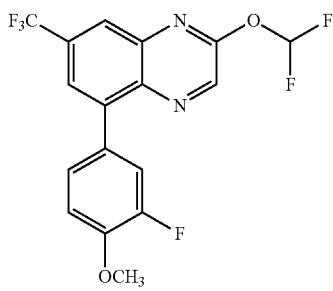

(12)

The title compound was prepared was prepared from 5-bromo-7-(trifluoromethyl) quinoxalin-2-ol and the appropriate boronic acid using Procedures 5 and 3. $^1$H NMR (500 MHz, DMSO-$d_6$) δ 9.03 (s, 1H), 8.30-8.25 (m, 1H), 8.07 (d, J=2.1 Hz, 1H), 7.93 (t, J=71.3 Hz, 1H), 7.64 (dd, J=12.5, 2.0 Hz, 1H), 7.67-7.60 (m, 1-), 7.54 (d, J=9.0 Hz, 1H), 7.34 (t, J=8.0 Hz, 1H), 3.94 (s, 3H). LCMS: (Condition 2) 4.5 min., M+1=389.1, EM=388.1.

Example 13

2-(difluoromethoxy)-5-(3-methoxy-5-(trifluoromethyl)phenyl)-7-(trifluoromethyl)quinoxaline

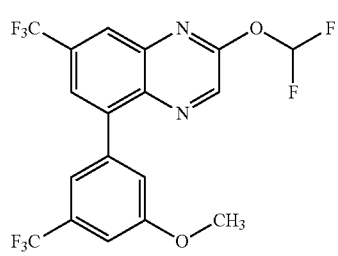

(13)

The title compound was prepared from 5-bromo-7-(trifluoromethyl)quinoxalin-2-ol and the appropriate boronic acid using Procedures 5 and 3. $^1$H NMR (500 MHz, DMSO-$d_6$) δ 9.03 (s, 1H), 8.38-8.34 (m, 1H), 8.22-8.15 (m, 1H), 7.94 (t, J=71.3 Hz, 1H), 7.60 (s, 1H), 7.57-7.53 (m, 1H), 7.41-7.34 (m, 1H), 3.93 (s, 3H). LCMS: (Condition 2) 4.7 min., M+1=439.2, EM=438.1.

Example 14

2-(difluoromethoxy)-8-(4-methoxyphenyl)-6-(trifluoromethyl)quinoxaline

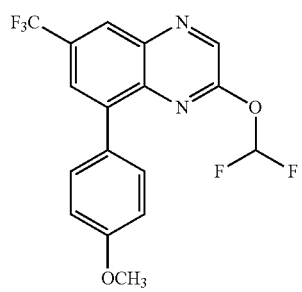

(14)

The title compound was prepared from 8-bromo-6-(trifluoromethyl)quinoxalin-2-ol and the appropriate boronic acid using Procedures 5 and 3. $^1$H NMR (500 MHz, chloroform-d) δ 8.73 (s, 1H), 8.38 (d, J=1.1 Hz, 1H), 8.00 (d, J=2.2 Hz, 1H), 7.65-7.61 (m, 2H), 7.46 (t, $J_{HF}$=71.5 Hz, 1H), 7.10-7.06 (m, 2H), 3.93 (s, 3H); $^{19}$F NMR (471 MHz, chloroform-d) δ −62.54 (s, 3F), −90.65 (s, 2F); LCMS: (Phenom. Luna C18 30×4.6 mm 5 m; A: 10% MeCN-90% H$_2$O-10 mM NH$_4$Ac; B: 90% MeCN-10% H$_2$O-10 mM NH$_4$Ac; wavelength 220 nm; flow rate 5 mL/min; gradient time 2 min; 40 to 100% B. RT=2.15 min.) 2.2 min., M+1=371.2, EM=370.1.

Example 15

5-(3-bromo-4-methoxyphenyl)-2-(difluoromethoxy)-7-(trifluoromethyl)quinoxaline

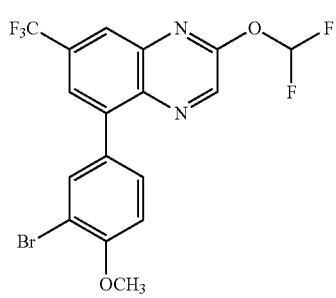

(15)

To a solution of potassium bromide (32.1 mg, 0.270 mmol) and dibromine (17.26 mg, 0.108 mmol) in water (1 ml) was added 2-(difluoromethoxy)-5-(4-methoxyphenyl)-7-(trifluoromethyl)quinoxaline (Example 9, 20 mg, 0.054 mmol) at 0° C. The mixture was stirred at 0° C., for 1 hr and stirred at room temperature overnight. LC/MS showed ~80% conversion. The crude material was purified via preparative LC/MS with the following conditions: Column: Waters XBridge C18, 19×200 mm, 5-µm particles; Guard Column:Waters XBridge C18, 19×10 mm, 5-µm particles; Mobile Phase A: water with 20-mM ammonium acetate; Mobile Phase B: 95:5 acetonitrile:water with 20-mM ammonium acetate: Gradient: 60-100% B over 13 minutes, then a 4-minute hold at 100% B; Flow: 20 mL/min. Fractions containing the desired product were combined and dried via centrifugal evaporation. The yield of the product was 4.7 mg, and its estimated purity by LCMS analysis was 100%. $^1$H NMR (500 MHz, DMSO-$d_6$) δ 9.03 (s, 1H), 8.28 (s, 1H), 8.08 (d, J=2.1 Hz, 1H), 7.96 (d, J=2.1 Hz, 1H), 7.93 (t, J=71.3 Hz, 1H), 7.74-7.71 (m, 1H), 7.29 (d, J=8.5 Hz, 1H), 3.96 (s, 3H). LC/MS(Condition 2) 4.6 min., M+1=449.1, EM=447.9.

Example 16

2-(difluoromethoxy)-5-(4-methoxy-3-(trifluoromethyl)phenyl)-7-methylquinoxaline

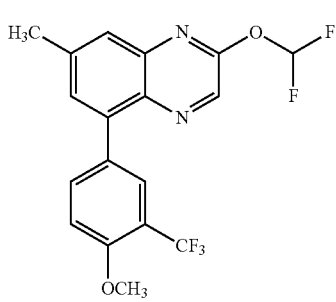

(16)

Intermediate 16A: 5-bromo-7-methylquinoxalin-2-ol

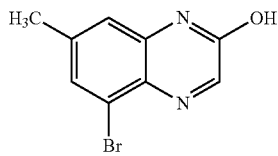
(16A)

Intermediate 16A was prepared from 3-bromo-5-methylbenzene-1,2-diamine using the general procedure of Intermediate 9A. $^1$H NMR (400 MHz, chloroform-d) δ 9.18-8.96 (m, 1H), 8.28 (s, 1H), 7.67 (s, 1H), 7.62 (d, J=1.2 Hz, 1H), 2.48 (s, 3H). LC/MS(Condition 1) 2.0 min., M+1=239.0, EM=238.0.

Example 16

Example 16 was prepared from 5-bromo-7-methylquinoxalin-2-ol and the appropriate boronic acid using Procedures 5 and 3. $^1$H NMR (500 MHz, DMSO-d$_6$) δ 8.78 (s, 1H), 7.96-7.92 (m, 1H), 7.89 (s, 1H), 7.89 (t, J=71.3 Hz, 1H), 7.77 (s, 1H), 7.76-7.74 (m, 1H), 7.42 (d, J=8.5 Hz, 1H), 3.99 (s, 3H), 2.61 (s, 3H). LCMS: (Condition 2) 4.6 min., M+1=385.1, EM=384.1.

Example 17

2-(difluoromethoxy)-5-(4-fluor-3-(trifluoromethyl)phenyl)-7-methylquinoxaline

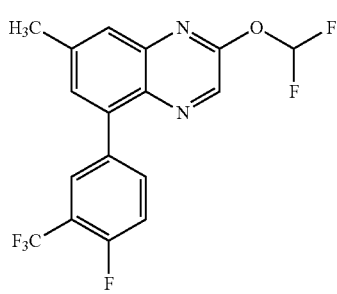
(17)

The title compound was prepared from 5-bromo-7-methylquinoxalin-2-ol and the appropriate boronic acid using Procedures 5 and 3. $^1$H NMR (500 MHz, DMSO-d$_6$) δ 8.80 (s, 1H), 8.06-8.00 (m, 2H), 7.90 (t, J=71.3 Hz, 1H), 7.84-7.79 (m, 2H), 7.71-7.64 (m, 1H), 2.62 (s, 3H). LCMS: (Condition 2) 4.6 min., M+1 not observed.

Example 18

5-(3-chlorophenyl)-2-(difluoromethoxy)-7-methylquinoxaline

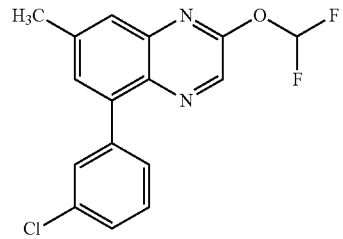
(18)

The title compound was prepared from 5-bromo-7-methylquinoxalin-2-ol and the appropriate boronic acid using Procedures 5 and 3. $^1$H NMR (500 MHz, methanol-d$_4$) δ 8.53 (s, 1H), 7.75-7.72 (m, 1H), 7.69 (t, J=71.3 Hz, 1H), 7.61 (br. s., 1H), 7.58 (d, J=1.5 Hz, 1H), 7.53-7.49 (m, 1H), 7.46-7.39 (m, 2H), 2.63 (s, 3H).

Example 19

2-(difluoromethoxy)-7-methyl-5-(4-trifluoromethyl)phenyl)quinoxaline

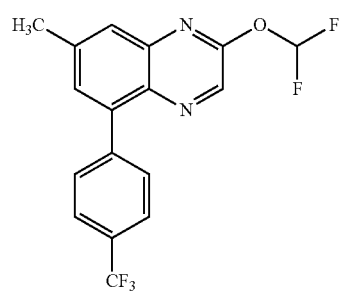
(19)

The title compound was prepared from 5-bromo-7-methylquinoxalin-2-ol and the appropriate boronic acid using Procedures 5 and 3. $^1$H NMR (500 MHz, methanol-d$_4$) δ 8.53 (s, 1H), 7.76 (d, J=4.5 Hz, 5H), 7.69 (t, J=71.3 Hz, 1H), 7.63-7.61 (m, 1H), 2.64 (s, 3H).

Example 20

2-(difluoromethoxy)-7-methyl-5-(4-(trifluoromethoxy)phenyl)quinoxaline

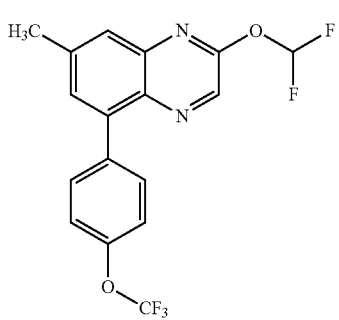
(20)

The title compound was prepared from 5-bromo-7-methylquinoxalin-2-ol and the appropriate boronic acid using Procedures 5 and 3. $^1$H NMR (500 MHz, methanol-d$_4$) δ 8.54 (s, 1H), 7.71 (d, J=1.5 Hz, 3H), 7.69 (t, J=71.3 Hz, 1H), 7.62-7.59 (m, 1H), 7.38-7.33 (m, 2H), 2.64 (s, 3H).

Example 21

2-(difluoromethoxy)-5-(3-fluoro-5-methoxyphenyl)-7-methylquinoxaline

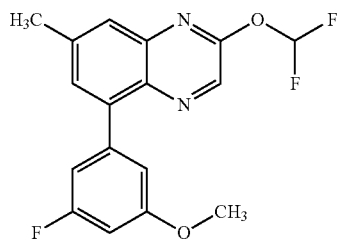

(21)

The title compound was prepared from 5-bromo-7-methylquinoxalin-2-ol and the appropriate boronic acid using Procedures 5 and 3. $^1$H NMR (500 MHz, methanol-d$_4$) δ 8.53 (s, 1H), 7.73 (s, 1H), 7.69 (t, J=71.3 Hz, 1H), 7.58 (d, J=2.0 Hz, 1H), 6.94 (d, J=1.5 Hz, 1H), 6.93-6.89 (m, 1H), 6.74-6.69 (m, 1H), 3.86 (s, 3H), 2.63 (s, 3H).

Example 22

2-(difluoromethoxy)-5-(3,4-difluorophenyl)-7-methylquinoxaline

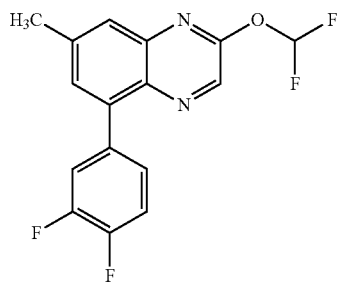

(22)

The title compound was prepared from 5-bromo-7-methylquinoxalin-2-ol and the appropriate boronic acid using Procedures 5 and 3. $^1$H NMR (500 MHz, methanol-d$_4$) δ 8.54 (s, 1H), 7.75-7.72 (m, 1H), 7.69 (t, J=71.3 Hz, 1H), 7.59-7.57 (m, 1H), 7.53-7.47 (m, 1H), 7.40-7.35 (m, 1H), 7.34-7.27 (m, 1H), 2.63 (s, 3H).

Example 23

5-(2,4-dichlorophenyl)-2-(difluoromethoxy)-7-methylquinoxaline

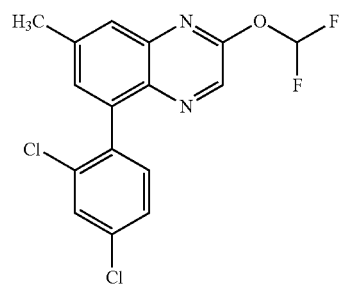

(23)

The title compound was prepared from 5-bromo-7-methylquinoxalin-2-ol and the appropriate boronic acid using Procedures 5 and 3. $^1$H NMR (500 MHz, methanol-d$_4$) δ 8.47 (s, 1H), 7.79-7.77 (m, 1H), 7.68 (t, J=71.3 Hz, 1H), 7.55 (d, J=2.0 Hz, 1H), 7.48 (d, J=2.0 Hz, 1H), 7.39 (dd, J=8.3, 2.0 Hz, 1H), 7.34 (d, J=8.3 Hz, 1H), 2.63 (s, 3H).

Example 24

5-(3,4-dichlorophenyl)-2-(difluoromethoxy)-7-methylquinoxaline

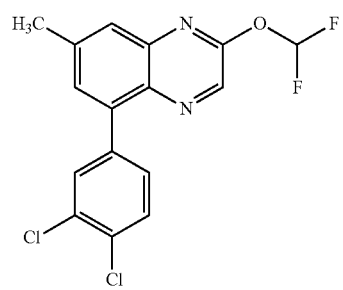

(24)

The title compound was prepared from 5-bromo-7-methylquinoxalin-2-ol and the appropriate boronic acid using Procedures 5 and 3. $^1$H NMR (500 MHz, methanol-d$_4$) δ 8.54 (s, 1H), 7.75 (d, J=2.5 Hz, 2H), 7.69 (t, J=71.3 Hz, 1H), 7.62-7.56 (m, 2H), 7.52-7.48 (m, 1H), 2.63 (s, 3H).

Example 25

2-(difluoromethoxy)-7-methyl-5-(3-(trifluoromethyl)phenyl)quinoxaline

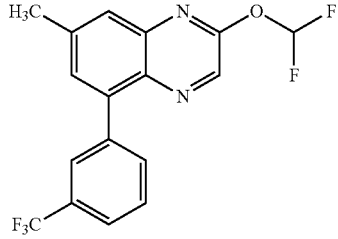

(25)

The title compound was prepared from 5-bromo-7-methylquinoxalin-2-ol and the appropriate boronic acid using Procedures 5 and 3. $^1$H NMR (500 MHz, DMSO-$d_6$) δ 8.79-8.75 (m, 1H), 7.99-7.94 (m, 2H), 7.89 (t, J=71.3 Hz, 1H), 7.84-7.80 (m, 2H), 7.79-7.72 (m, 2H), 2.6 s, 3H).

Example 26

2-(difluoromethoxy)-7-methyl-5-(4-(trifluoromethoxy)phenyl)quinoxaline

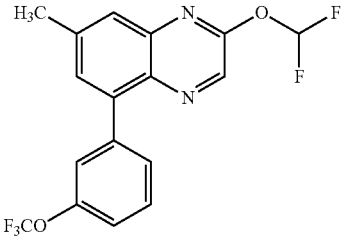

(26)

The title compound was prepared from 5-bromo-7-methylquinoxalin-2-ol and the appropriate boronic acid using Procedures 5 and 3. $^1$H NMR (500 MHz, methanol-$d_4$) δ 8.55 (s, 1H), 7.77-7.74 (m, 1H), 7.70 (t, J=71.3 Hz, 1H), 7.62-7.58 (m, 2H), 7.57-7.49 (m, 2H), 7.34-7.28 (m, 1H), 2.64 (s, 3H).

Example 27

7-bromo-2-(difluoromethoxy)-5-(4-methoxyphenyl)quinoxaline

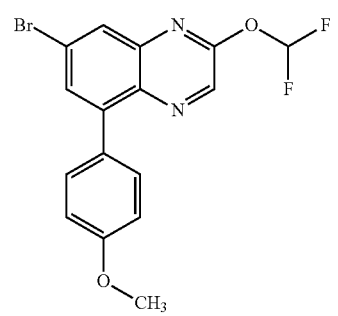

(27)

Intermediate 27A: 5-bromo-3-iodobenzene-1,2-diamine

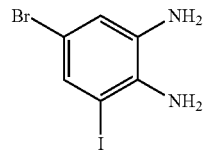

(27A)

To a solution of 4-bromo-2-iodo-6-nitroaniline (4.5 g, 13.12 mmol) in ethanol (80 mL) was added concentrated HCl (5.47 mL, 65.6 mmol), followed by tin(II) chloride dihydrate (11.84 g, 52.5 mmol). The mixture was stirred at 60° C. over night. The mixture was then cooled to room temperature and treated with ice-cold, aqueous, 4.0 N NaOH (18 mL) and ethyl acetate. After stirring for 10 min, the white solid material was removed by filtration. The filtrate was separated. The organic layer was collected, washed with brine and dried over sodium sulfate. After evaporation of solvent, the crude product was dissolved in a small amount of chloroform and charged to a 80 g silica gel cartridge which was eluted with 5% to 50% ethyl acetate in hexanes. The desired fractions were combined and concentrated to give the product (3.3 g, 10.55 mmol, 80% yield) as a pale brown solid. $^1$H NMR (500 MHz, chloroform-d) δ 7.33 (d, J=2.2 Hz, 1H), 6.83 (d, J=1.9 Hz, 1H), 3.81 (br. s., 2H), 3.54 (br. s., 2H); LCMS: (Phenom. Luna C18 30×4.6 mm 5 m; A: 10% MeCN-90% H$_2$O-0.1% TFA; B: 90% MeCN-10% H$_2$O-0.1% TFA; wavelength 220 nm; flow rate 5 mL/min; gradient time 2 min; 0 to 100% B.) 1.82 min, M+1=313.8, EM=312.8.

Intermediate 27B: 7-Bromo-5-iodoquinoxalin-2-ol

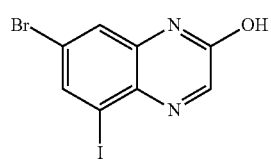

(27B)

To a solution of 5-bromo-3-iodobenzene-1,2-diamine (3.3 g, 10.55 mmol) in ethanol (40 mL) was added ethyl 2-oxoacetate (50% in toluene) (2.58 mL, 12.65 mmol). The mixture was heated at 45° C., for 2.0 h. HPLC and LCMS indicated completion of reaction. After cooling, the precipitate was collected by filtration, washed with ethanol to give Intermediate 27B (2.83 g, 8.06 mmol, 76% yield). $^1$H NMR shows a mixture of two isomers., MS (ESI) m/z: 351.0 and 353.0 (M+H)$^+$. LCMS: (Phenom. Luna C18 30×4.6 mm 5 m; A: 10% MeCN-90% H$_2$O-0.10/TFA; B: 90% MeCN-10% H$_2$O-0.1% TFA; wavelength 220 nm; flow rate 5 mL/min; gradient time 2 min; 0 to 100% B.) 1.80 and 1.88 min, M+1=351.0 and 353.0, EM=350.0.

Intermediate 27C:
7-bromo-2-(difluoromethoxy)-5-iodoquinoxaline

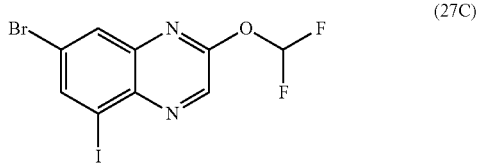 [SMILES: FC(F)Oc1cnc2c(I)cc(Br)cc2n1]
(27C)

A mixture of 6- and 7-bromo-5-iodoquinoxalin-2-ol (2.82 g, 8.04 mmol) and potassium carbonate (22.21 g, 161 mmol) in DMF (50 mL) and water (2.5 mL) was heated at 90° C., for 4 min, then sodium 2-chloro-2,2-difluoroacetate (4.90 g, 32.1 mmol) was added. After 15 min at 90° C., another portion of sodium 2-chloro-2,2-difluoroacetate (4.90 g, 32.1 mmol) was added. After 15 min at 90° C., a third portion of sodium 2-chloro-2,2-difluoroacetate (4.90 g, 32.1 mmol) was added. TLC (ethyl acetate/hexanes 6:9) was used to monitor the progress of the reaction. A fourth portion of sodium 2-chloro-2,2-difluoroacetate (4.90 g, 32.1 mmol) was added after 15 min at 90° C. The mixture was filtered and the solid was washed with 10 mL of DMF. The filtrate was resubjected to the above reaction with approximately 5.0 eq of potassium carbonate and 5.0 eq. of sodium chlorodifluoroacetate. The reaction mixture was cooled to room temperature and diluted with dichloromethane and water. The mixture was stirred for 15 min and the insoluble material was removed by filtration. The filtrate was collected and extracted with dichloromethane. The organic layer was washed with brine and dried over sodium sulfate. After evaporation of solvent, the crude product was dissolved in a small amount of toluene and charged to a 120 g silica gel cartridge which was eluted with 5% to 40% dichloromethane in hexanes. The desired fractions were combined and concentrated to give the product (0.625 g, 1.559 mmol, 19.40% yield): as a white solid: $^1$H NMR (500 MHz, dichloromethane-$d_2$) δ 8.66 (s, 1H), 8.46 (d, J=2.2 Hz, 1H), 8.14 (d, J=1.9 Hz, 1H), 7.65 (t, $J_{HF}$=71.25 Hz, 1H); $^{19}$F NMR (471 MHz, dichloromethane-$d_2$) δ −90.28 (s, 1F).

Example 27

A mixture of 7-bromo-2-(difluoromethoxy)-5-iodoquinoxaline (725 mg, 1.808 mmol), (4-methoxyphenyl)boronic acid (302 mg, 1.989 mmol) and [1,1'-bis (diphenylphosphino)ferrocene]dichloropalladium (II) complex with dichloromethane (1:1) (89 mg, 0.108 mmol) in toluene (12 mL) and ethanol (4.00 mL) was degassed with argon. To this solution was added sodium carbonate, 2M (1.582 mL, 3.16 mmol). The mixture was then heated in a pressure flask at 75° C. overnight. HPLC indicated a clean reaction. It was diluted with ethyl acetate and water. The organic layer was collected, washed with brine and dried over sodium sulfate. After evaporation of solvent, the crude product was dissolved in a small amount of toluene and charged to a 40 g silica gel cartridge which was eluted with 5% to 60% dichloromethane in hexanes. The desired fractions were combined and concentrated to give the product (540 mg, 1.417 mmol, 78% yield) as a yellow solid. $^1$H NMR (500 MHz, acetonitrile-$d_3$) δ 8.69 (s, 1H), 8.29 (d, J=2.2 Hz, 1H), 8.00 (d, J=2.2 Hz, 1H), 7.71-7.67 (m, 2H), 7.48 (t, $J_{HF}$=71.53 Hz, 1H), 7.12-7.07 (m, 2H), 3.90 (s, 3H); $^{19}$F NMR (471 MHz, acetonitrile-$d_3$) δ −90.44 (s, 2F); RT=2.40 min, MS (ESI) m/z: 381.0 and 383.0 (M+H)$^+$. LCMS: (Phenom. Luna C18 30×4.6 mm 5 m; A: 10% MeCN-90% H$_2$O-0.1% TFA; B: 90% MeCN-10% H2O-0.1% TFA; wavelength 220 nm; flow rate 5 mL/min; gradient time 2 min; 0 to 100% B.) 2.40 min, M+1=381.0 and 383.0, EM=380.0.

What is claimed is:

1. A method for the treatment of a thromboembolic disorder or the primary prophylaxis of a thromboembolic disorder, comprising the steps of administering to a patient in need thereof a therapeutically effective amount of a compound of Formula (II), (III), or (IV):

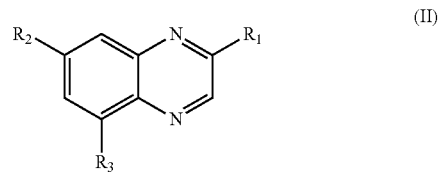
(II)

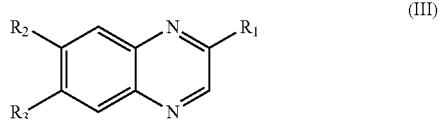
(III)

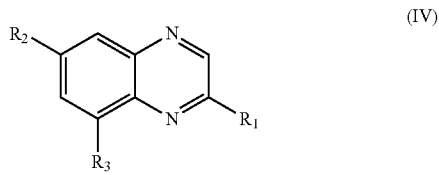
(IV)

or a pharmaceutically acceptable salt thereof, wherein:

$R_1$ is —OCH$_3$, —OCHF$_2$, or —CH$_2$OCH$_3$;

$R_2$ is H, F, Cl, Br, —OH, —CN, $C_{1-3}$ alkyl, $C_{1-3}$ fluoroalkyl, $C_{1-3}$ hydroxyalkyl, $C_{2-4}$ alkenyl, $C_{2-4}$ alkenyl, or —C(O)O ($C_{1-6}$ alkyl);

$R_3$ is phenyl or naphthalenyl substituted with zero to 2 $R_{3a}$; and $R_{3a}$, at each occurrence, is independently F, Cl, Br, $C_{1-3}$ alkyl, $C_{1-3}$ fluoroalkyl, $C_{1-3}$ alkoxy, or $C_{1-3}$ fluoroalkoxy;

wherein the thromboembolic disorder is selected from the group consisting of arterial cardiovascular thromboembolic disorders, venous cardiovascular thromboembolic disorders, and thromboembolic disorders in the chambers of the heart or in the peripheral circulation.

2. The method according to claim 1 wherein the thromboembolic disorder is selected from the group consisting of unstable angina, an acute coronary syndrome, atrial fibrillation, myocardial infarction, transient ischemic attack, stroke, atherosclerosis, peripheral occlusive arterial disease, venous thrombosis, deep vein thrombosis, thrombophlebitis, arterial embolism, coronary arterial thrombosis, cerebral arterial thrombosis, cerebral embolism, kidney embolism, pulmonary embolism, and thrombosis resulting from medical implants, devices, and procedures in which blood is exposed to an artificial surface that promotes thrombosis.

3. A method of inhibiting or preventing platelet aggregation, comprising the step of administering to a subject in need thereof a therapeutically effective amount of a compound of Formula (II), (III), or (IV):

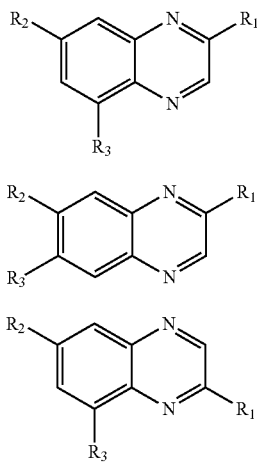

(II)

(III)

(IV)

or a pharmaceutically acceptable salt thereof, wherein:

$R_1$ is —OCH, —OCHF, or —CH$_2$OCH$_3$;

$R_2$ is H, F, Cl, Br, —OH, —CN, C$_{1-3}$ alkyl, C$_{1-3}$ fluoroalkyl, C$_{1-3}$ hydroxyalkyl, C$_{2-4}$ alkenyl, C$_{2-4}$ alkynyl, or —C(O)O (C$_{1-6}$ alkyl);

$R_3$ is phenyl or naphthalenyl substituted with zero to 2 $R_{3a}$; and $R_{3a}$, at each occurrence, is independently F, Cl, Br, C$_{1-3}$ alkyl, C$_{1-3}$ fluoroalkyl, C$_{1-3}$ alkoxy, or C$_{1-3}$ fluoroalkoxy.

4. A method for the treatment of human papillomavirus, comprising the steps of administering to a patient in need thereof a therapeutically effective amount of a compound of Formula (II), (III), or (IV):

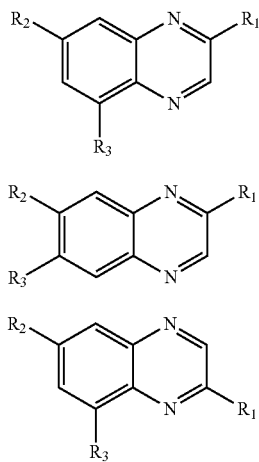

(II)

(III)

(IV)

or a pharmaceutically acceptable salt thereof, wherein:

$R_1$ is —OCH, —OCHF, or —CH$_2$OCH$_3$;

$R_2$ is H, F, Cl, Br, —OH, —CN, C$_{1-3}$ alkyl, C$_{1-3}$ fluoroalkyl, C$_{1-3}$ hydroxyalkyl, C$_{2-4}$ alkenyl, C$_{2-4}$ alkynyl, or —C(O)O (C$_{1-6}$ alkyl);

$R_3$ is phenyl or naphthalenyl substituted with zero to 2 $R_{3a}$; and $R_{3a}$, at each occurrence, is independently F, Cl, Br, C$_{1-3}$ alkyl, C$_{1-3}$ fluoroalkyl, C$_{1-3}$ alkoxy, or C$_{1-3}$ fluoroalkoxy.

\* \* \* \* \*

UNITED STATES PATENT AND TRADEMARK OFFICE
CERTIFICATE OF CORRECTION

PATENT NO. : 10,517,870 B2
APPLICATION NO. : 15/747218
DATED : December 31, 2019
INVENTOR(S) : Xiaojun Zhang et al.

It is certified that error appears in the above-identified patent and that said Letters Patent is hereby corrected as shown below:

On the Title Page

Item (54) (Title), Line 1 (Approx.) and in the Specification, Column 1, Line 1, delete "BICYCLE" and insert -- BICYCLIC --, therefor.

In the Claims

In Claim 3, Column 67, Line 22 (Approx.), delete "—OCH,—OCHF," and insert -- —OCH$_3$, —OCHF$_2$, --, therefor.

In Claim 4, Column 68, Line 24 (Approx.), delete "—OCH, —OCHF," and insert -- —OCH$_3$, —OCHF$_2$, --, therefor.

Signed and Sealed this
Fourteenth Day of July, 2020

Andrei Iancu
*Director of the United States Patent and Trademark Office*